US009632084B2

(12) United States Patent
Trouw et al.

(10) Patent No.: US 9,632,084 B2
(45) Date of Patent: Apr. 25, 2017

(54) ANTI-CARBAMYLATED PROTEIN ANTIBODIES AND THE RISK FOR ARTHRITIS

(76) Inventors: Leendert Adrianus Trouw, Leiden (NL); Reinaldus Everardus Maria Toes, Leiden (NL); Thomas Willem Johannes Huizinga, Leiden (NL); Petrus Antonius van Veelen, Leiden (NL); Anthony Cerami, Leiden (NL); Jing Shi, Leiden (NL)

( * ) Notice: Subject to any disclaimer, the term of this patent is extended or adjusted under 35 U.S.C. 154(b) by 134 days.

(21) Appl. No.: 13/983,374

(22) PCT Filed: Feb. 1, 2012

(86) PCT No.: PCT/NL2012/050056
§ 371 (c)(1),
(2), (4) Date: Feb. 27, 2014

(87) PCT Pub. No.: WO2012/105838
PCT Pub. Date: Aug. 9, 2012

(65) Prior Publication Data
US 2014/0162297 A1    Jun. 12, 2014

(30) Foreign Application Priority Data

Feb. 2, 2011   (EP) ..................... 11153046
Sep. 22, 2011  (EP) ..................... 11182399

(51) Int. Cl.
*G01N 33/53*      (2006.01)
*G01N 33/564*     (2006.01)
*G01N 33/68*      (2006.01)

(52) U.S. Cl.
CPC ....... *G01N 33/564* (2013.01); *G01N 33/6854* (2013.01); *G01N 2800/101* (2013.01); *G01N 2800/102* (2013.01); *G01N 2800/104* (2013.01); *G01N 2800/105* (2013.01); *G01N 2800/107* (2013.01)

(58) Field of Classification Search
CPC ............. G01N 33/564; G01N 33/6854; G01N 2800/101; G01N 2800/102; G01N 2800/104; G01N 2800/105; G01N 2800/28; G01N 2800/107; Y10S 435/808
See application file for complete search history.

(56) References Cited

U.S. PATENT DOCUMENTS 5,420,016 A * 5/1995 Boguslaski ............ C12Q 1/04
                                               106/2
2007/0087380 A1   4/2007  Van Venrooij et al.
2007/0141625 A1 * 6/2007  Santos ................. G01N 33/564
                                               435/7.1
2008/0305990 A1  12/2008  Brines et al.
2011/0014632 A1 * 1/2011  Holzman ............. G01N 33/564
                                               435/7.9
2011/0104818 A1 * 5/2011  Hazen ................. G01N 33/6812
                                               436/501
2011/0165606 A1   7/2011  Tutturen et al.
2011/0195861 A1   8/2011  Van Venrooij et al.

FOREIGN PATENT DOCUMENTS

| WO | WO 03-050542     | 6/2003 |
| WO | WO 2006-014349 A2 | 2/2006 |
| WO | WO 2009-007846 A2 | 1/2009 |
| WO | WO 2009-032722 A1 | 3/2009 |
| WO | WO 2012-105838 A1 | 8/2012 |

OTHER PUBLICATIONS

Nechansky, HAHA—nothing to laught about. Measuring the immunogenicity (human anti-human antibody response) induced by humanized monoclonal antibodies applying ELISA and SPR technology, Journal of Pharmaceutical and Biomedical Analysis 51, 2010, pp. 252-254.*
Steinbrecher et al., Immunogenicity of homologous low density lipoprotein after methylation, ethylation, aetylation, or carbamylation: generation of antibodies specific for derivatized lysine, Journal of Lipid Research, vol. 25, 1984, pp. 1109-1116.*
Mydel et al., Carbamylation-Dependent Activation of T Cells: A Novel Mechanism in the Pathogenesis of Autoimmune Arthritis, Journal of Immunology, Jun. 2010, pp. 6882-6890, vol. 184, No. 12.
Klareskog et al., Immunity to Citrullinated Proteins in Rheumatoid Arthritis, Annual Review of Immunology, Jan. 1, 2008, pp. 651-675, Annual Reviews, Inc. US.
PCT International Search Report, PCT/NL2012/050056, dated Jul. 24, 2012.
PCT International Preliminary Report on Patentability, PCT/NL2012/050056 dated Apr. 22, 2013.
Shaykh et al., Carbamylated proteins activate glomerular mesangial cells and stimulate collagen deposition, J. Lab Clin Med., Mar. 1999, pp. 302-308, vol. 133, No. 3.
Angel et al., Quantitative carbamylation as a stable isotopic labeling method for comparative proteomics, Rapid Communications in Mass Spectrometry, 2007, pp. 1623-1634, vol. 21, Wiley InterScience, John Wiley & Sons, Ltd.

* cited by examiner

*Primary Examiner* — Gary W Counts
(74) *Attorney, Agent, or Firm* — TraskBritt P.C.

(57) ABSTRACT

Antibodies against citrullinated protein antigens (ACPA) have shown their relevance for the diagnosis and possibly pathogenesis in arthritis. Described are means and methods for determining antibodies against homocitrulline-containing proteins or carbamylated proteins/peptides (anti-CarP) for the classification of individuals suffering from, or at risk of suffering from, arthritis.

9 Claims, 18 Drawing Sheets

```
Aminoacid sequence of Fibrinogen alpha
         10         20         30         40         50         60
MFSMRIVCLV LSVVGTAWTA DSGEGDFLAE GGGVRGPRVV ERHQSACKDS DWPFCSDEDW
         70         80         90        100        110        120
NYKCPSGCRM KGLIDEVNQD FTNRINKLKN SLFEYQKNNK DSHSLTTNIM EILRGDFSSA
        130        140        150        160        170        180
NNRDNTYNRV SEDLRSRIEV LKRKVIEKVQ HIQLLQKNVR AQLVDMKRLE VDIDIKIRSC
        190        200        210        220        230        240
RGSCSRALAR EVDLKDYEDQ QKQLEQVIAK DLLPSRDRQH LPLIKMKPVP DLVPGNFKSQ
        250        260        270        280        290        300
LQKVPPEWKA LTDMPQMRME LERPGGNEIT RGGSTSYGTG SETESPRNPS SAGSWNSGSS
        310        320        330        340        350        360
GPGSTGNRNP GSSGTGGTAT WKPGSSGPGS TGSWNSGSSG TGSTGNQNPG SPRPGSTGTW
        370        380        390        400        410        420
NPGSSERGSA GHWTSESSVS GSTGQWHSES GSFRPDSPGS GNARPNNPDW GTFEEVSGNV
        430        440        450        460        470        480
SPGTRREYHT EKLVTSKGDK ELRTGKEKVT SGSTTTTRRS CSKTVTKTVI GPDGHKEVTK
        490        500        510        520        530        540
EVVTSEDGSD CPEAMDLGTL SGIGTLDGFR HRHPDEAAFF DTASTGKTFP GFFSPMLGEF
        550        560        570        580        590        600
VSETESRGSE SGIFTNTKES SSHHPGIAEF PSRGKSSSYS KQFTSSTSYN RGDSTFESKS
        610        620        630        640        650        660
YKMADEAGSE ADHEGTHSTK RGHAKSRPVR DCDDVLQTHP SGTQSGIFNI KLPGSSKIFS
        670        680        690        700        710        720
VYCDQETSLG GWLLIQQRMD GSLNFNRTWQ DYKRGFGSLN DEGEGEFWLG NDYLHLLTQR
        730        740        750        760        770        780
GSVLRVELED WAGNEAYAEY HFRVGSEAEG YALQVSSYEG TAGDALIEGS VEEGAEYTSH
        790        800        810        820        830        840
NNMQFSTFDR DADQWEENCA EVYGGGWWYN NCQAANLNGI YYPGGSYDPR NNSPYEIENG
        850        860
VVWVSFRGAD YSLRAVRMKI RPLVTQ
```

Fig. 14

```
Aminoacid sequence of Fibrinogen beta
         10         20         30         40         50         60
MKRMVSWSFH KLKTMKHLLL LLLCVFLVKS QGVNDNEEGF FSARGHRPLD KKREEAPSLR
         70         80         90        100        110        120
PAPPPISGGG YRARPAKAAA TQKKVERKAP DAGGCLHADP DLGVLCPTGC QLQEALLQQE
        130        140        150        160        170        180
RPIRNSVDEL NNNVEAVSQT SSSSFQYMYL LKDLWQKRQK QVKDNENVVN EYSSELEKHQ
        190        200        210        220        230        240
LYIDETVNSN IPTNLRVLRS ILENLRSKIQ KLESDVSAQM EYCRTPCTVS CNIPVVS
        250        260        270        280        290        300
CEEIIRKGGE TSEMYLIQPD SSVKPYRVYC DMNTENGGWT VIQNRQDGSV DFGRKWDPYK
        310        320        330        340        350        360
QGFGNVATNT DGKNYCGLPG EYWLGNDKIS QLTRMGPTEL LIEMEDWKGD KVKAHYGGFT
        370        380        390        400        410        420
VQNEANKYQI SVNKYRGTAG NALMDGASQL MGENRTMTIH NGMFFSTYDR DNDGWLTSDP
        430        440        450        460        470        480
RKQCSKEDGG GWWYNRCHAA NPNGRYYWGG QYTWDMAKHG TDDGVVWMNW KGSWYSMRKM
        490
SMKIRPFFPQ Q
```

Fig. 15

```
Aminoacid sequence of Fibrinogen gamma
         10         20         30         40         50         60
MSWSLHPRNL ILYFYALLFL SSTCVAYVAT RDNCCILDER FGSYCPTTCG IADFLSTYQT
         70         80         90        100        110        120
KVDKDLQSLE DILHQVENKT SEVKQLIKAI QLTYNPDESS KPNMIDAATL KSRKMLEEIM
        130        140        150        160        170        180
KYEASILTHD SSIRYLQEIY NSNNQKIVNL KEKVAQLEAQ CQEPCKDTVQ IHDITGKDCQ
        190        200        210        220        230        240
DIANKGAKQS GLYFIKPLKA NQQFLVYCEI DGSGNGWTVF QKRLDGSVDF KKNWIQYKEG
        250        260        270        280        290        300
FGHLSPTGTT EFWLGNEKIH LISTQSAIPY ALRVELEDWN GRTSTADYAM FKVGPEADKY
        310        320        330        340        350        360
RLTYAYFAGG DAGDAFDGFD FGDDPSDKFF TSHNGMQFST WDNDNDKFEG NCAEQDGSGW
        370        380        390        400        410        420
WMNKCHAGHL NGVYYQGGTY SKASTPNGYD NGIIWATWKT RWYSMKKTTM KIIPFNRLTI
        430        440        450
GEGQQHHLGG AKQVRPEHPA ETEYDSLYPE DDL
```

Fig. 16

SEQUENCE LISTING

<160> NUMBER OF SEQ ID NOS: 215

<210> SEQ ID NO 1
<211> LENGTH: 866
<212> TYPE: PRT
<213> ORGANISM: Homo sapiens

<400> SEQUENCE: 1

Met Phe Ser Met Arg Ile Val Cys Leu Val Leu Ser Val Val Gly Thr
1               5                   10                  15

```
Ala Trp Thr Ala Asp Ser Gly Glu Gly Asp Phe Leu Ala Glu Gly Gly
            20                  25                  30

Gly Val Arg Gly Pro Arg Val Val Glu Arg His Gln Ser Ala Cys Lys
        35                  40                  45

Asp Ser Asp Trp Pro Phe Cys Ser Asp Glu Asp Trp Asn Tyr Lys Cys
50                  55                  60

Pro Ser Gly Cys Arg Met Lys Gly Leu Ile Asp Glu Val Asn Gln Asp
65                  70                  75                  80

Phe Thr Asn Arg Ile Asn Lys Leu Lys Asn Ser Leu Phe Glu Tyr Gln
                85                  90                  95

Lys Asn Asn Lys Asp Ser His Ser Leu Thr Thr Asn Ile Met Glu Ile
            100                 105                 110

Leu Arg Gly Asp Phe Ser Ser Ala Asn Asn Arg Asp Asn Thr Tyr Asn
        115                 120                 125

Arg Val Ser Glu Asp Leu Arg Ser Arg Ile Glu Val Leu Lys Arg Lys
    130                 135                 140

Val Ile Glu Lys Val Gln His Ile Gln Leu Leu Gln Lys Asn Val Arg
145                 150                 155                 160

Ala Gln Leu Val Asp Met Lys Arg Leu Glu Val Asp Ile Asp Ile Lys
                165                 170                 175

Ile Arg Ser Cys Arg Gly Ser Cys Ser Arg Ala Leu Ala Arg Glu Val
            180                 185                 190

Asp Leu Lys Asp Tyr Glu Asp Gln Gln Lys Gln Leu Glu Gln Val Ile
        195                 200                 205

Ala Lys Asp Leu Leu Pro Ser Arg Asp Arg Gln His Leu Pro Leu Ile
    210                 215                 220

Lys Met Lys Pro Val Pro Asp Leu Val Pro Gly Asn Phe Lys Ser Gln
225                 230                 235                 240

Leu Gln Lys Val Pro Pro Glu Trp Lys Ala Leu Thr Asp Met Pro Gln
                245                 250                 255

Met Arg Met Glu Leu Glu Arg Pro Gly Gly Asn Glu Ile Thr Arg Gly
            260                 265                 270

Gly Ser Thr Ser Tyr Gly Thr Gly Ser Glu Thr Glu Ser Pro Arg Asn
        275                 280                 285

Pro Ser Ser Ala Gly Ser Trp Asn Ser Gly Ser Ser Gly Pro Gly Ser
    290                 295                 300

Thr Gly Asn Arg Asn Pro Gly Ser Ser Gly Thr Gly Gly Thr Ala Thr
305                 310                 315                 320

Trp Lys Pro Gly Ser Ser Gly Pro Gly Ser Thr Gly Ser Trp Asn Ser
                325                 330                 335

Gly Ser Ser Gly Thr Gly Ser Thr Gly Asn Gln Asn Pro Gly Ser Pro
            340                 345                 350

Arg Pro Gly Ser Thr Gly Thr Trp Asn Pro Gly Ser Ser Glu Arg Gly
        355                 360                 365

Ser Ala Gly His Trp Thr Ser Glu Ser Ser Val Ser Gly Ser Thr Gly
    370                 375                 380

Gln Trp His Ser Glu Ser Gly Ser Phe Arg Pro Asp Ser Pro Gly Ser
385                 390                 395                 400

Gly Asn Ala Arg Pro Asn Asn Pro Asp Trp Gly Thr Phe Glu Glu Val
                405                 410                 415

Ser Gly Asn Val Ser Pro Gly Thr Arg Arg Glu Tyr His Thr Glu Lys
            420                 425                 430
```

-continued

Leu Val Thr Ser Lys Gly Asp Lys Glu Leu Arg Thr Gly Lys Glu Lys
            435                 440                 445

Val Thr Ser Gly Ser Thr Thr Thr Thr Arg Arg Ser Cys Ser Lys Thr
450                 455                 460

Val Thr Lys Thr Val Ile Gly Pro Asp Gly His Lys Glu Val Thr Lys
465                 470                 475                 480

Glu Val Val Thr Ser Glu Asp Gly Ser Asp Cys Pro Glu Ala Met Asp
                485                 490                 495

Leu Gly Thr Leu Ser Gly Ile Gly Thr Leu Asp Gly Phe Arg His Arg
            500                 505                 510

His Pro Asp Glu Ala Ala Phe Phe Asp Thr Ala Ser Thr Gly Lys Thr
            515                 520                 525

Phe Pro Gly Phe Phe Ser Pro Met Leu Gly Glu Phe Val Ser Glu Thr
530                 535                 540

Glu Ser Arg Gly Ser Glu Ser Gly Ile Phe Thr Asn Thr Lys Glu Ser
545                 550                 555                 560

Ser Ser His His Pro Gly Ile Ala Glu Phe Pro Ser Arg Gly Lys Ser
                565                 570                 575

Ser Ser Tyr Ser Lys Gln Phe Thr Ser Ser Thr Ser Tyr Asn Arg Gly
            580                 585                 590

Asp Ser Thr Phe Glu Ser Lys Ser Tyr Lys Met Ala Asp Glu Ala Gly
            595                 600                 605

Ser Glu Ala Asp His Glu Gly Thr His Ser Thr Lys Arg Gly His Ala
            610                 615                 620

Lys Ser Arg Pro Val Arg Asp Cys Asp Val Leu Gln Thr His Pro
625                 630                 635                 640

Ser Gly Thr Gln Ser Gly Ile Phe Asn Ile Lys Leu Pro Gly Ser Ser
            645                 650                 655

Lys Ile Phe Ser Val Tyr Cys Asp Gln Glu Thr Ser Leu Gly Gly Trp
            660                 665                 670

Leu Leu Ile Gln Gln Arg Met Asp Gly Ser Leu Asn Phe Asn Arg Thr
            675                 680                 685

Trp Gln Asp Tyr Lys Arg Gly Phe Gly Ser Leu Asn Asp Glu Gly Glu
690                 695                 700

Gly Glu Phe Trp Leu Gly Asn Asp Tyr Leu His Leu Thr Gln Arg
705                 710                 715                 720

Gly Ser Val Leu Arg Val Glu Leu Glu Asp Trp Ala Gly Asn Glu Ala
                725                 730                 735

Tyr Ala Glu Tyr His Phe Arg Val Gly Ser Glu Ala Glu Gly Tyr Ala
            740                 745                 750

Leu Gln Val Ser Ser Tyr Glu Gly Thr Ala Gly Asp Ala Leu Ile Glu
            755                 760                 765

Gly Ser Val Glu Glu Gly Ala Glu Tyr Thr Ser His Asn Asn Met Gln
770                 775                 780

Phe Ser Thr Phe Asp Arg Asp Ala Asp Gln Trp Glu Glu Asn Cys Ala
785                 790                 795                 800

Glu Val Tyr Gly Gly Gly Trp Trp Tyr Asn Asn Cys Gln Ala Ala Asn
                805                 810                 815

Leu Asn Gly Ile Tyr Tyr Pro Gly Gly Ser Tyr Asp Pro Arg Asn Asn
            820                 825                 830

Ser Pro Tyr Glu Ile Glu Asn Gly Val Val Trp Val Ser Phe Arg Gly
            835                 840                 845

Ala Asp Tyr Ser Leu Arg Ala Val Arg Met Lys Ile Arg Pro Leu Val 850                 855                 860

Thr Gln
865

<210> SEQ ID NO 2
<211> LENGTH: 488
<212> TYPE: PRT
<213> ORGANISM: Homo sapiens

<400> SEQUENCE: 2

Met Lys Arg Met Val Ser Trp Ser Phe His Lys Leu Lys Thr Met Lys
1               5                   10                  15

His Leu Leu Leu Leu Leu Leu Cys Val Phe Leu Val Lys Ser Gln Gly
            20                  25                  30

Val Asn Asp Asn Glu Glu Gly Phe Phe Ser Ala Arg Gly His Arg Pro
        35                  40                  45

Leu Asp Lys Lys Arg Glu Glu Ala Pro Ser Leu Arg Pro Ala Pro Pro
    50                  55                  60

Pro Ile Ser Gly Gly Gly Tyr Arg Ala Arg Pro Ala Lys Ala Ala Ala
65                  70                  75                  80

Thr Gln Lys Lys Val Glu Arg Lys Ala Pro Asp Ala Gly Gly Cys Leu
                85                  90                  95

His Ala Asp Pro Asp Leu Gly Val Leu Cys Pro Thr Gly Cys Gln Leu
            100                 105                 110

Gln Glu Ala Leu Leu Gln Gln Glu Arg Pro Ile Arg Asn Ser Val Asp
        115                 120                 125

Glu Leu Asn Asn Asn Val Glu Ala Val Ser Gln Thr Ser Ser Ser Ser
    130                 135                 140

Phe Gln Tyr Met Tyr Leu Leu Lys Asp Leu Trp Gln Lys Arg Gln Lys
145                 150                 155                 160

Gln Val Lys Asp Asn Glu Asn Val Val Asn Glu Tyr Ser Ser Glu Leu
                165                 170                 175

Glu Lys His Gln Leu Tyr Ile Asp Glu Thr Val Asn Ser Asn Ile Pro
            180                 185                 190

Thr Asn Leu Arg Val Leu Arg Ser Ile Leu Glu Asn Leu Arg Ser Lys
        195                 200                 205

Ile Gln Lys Leu Glu Ser Asp Val Ser Ala Gln Met Glu Tyr Cys Arg
    210                 215                 220

Thr Pro Cys Thr Val Ser Cys Asn Ile Pro Val Val Ser Cys Glu Glu
225                 230                 235                 240

Ile Ile Arg Lys Gly Gly Glu Thr Ser Glu Met Tyr Leu Ile Gln Pro
                245                 250                 255

Asp Ser Ser Val Lys Pro Tyr Arg Val Tyr Cys Asp Met Asn Thr Glu
            260                 265                 270

Asn Gly Gly Trp Thr Val Ile Gln Asn Arg Gln Asp Gly Ser Val Asp
        275                 280                 285

Phe Gly Arg Lys Trp Asp Pro Tyr Lys Gln Gly Phe Gly Asn Val Ala
    290                 295                 300

Thr Asn Thr Asp Gly Lys Asn Tyr Cys Gly Leu Pro Gly Glu Tyr Trp
305                 310                 315                 320

Leu Gly Asn Asp Lys Ile Ser Gln Leu Thr Arg Met Gly Pro Thr Glu
                325                 330                 335

Leu Leu Ile Glu Met Glu Asp Trp Lys Gly Asp Lys Val Lys Ala His
            340                 345                 350

```
Tyr Gly Gly Phe Thr Val Gln Asn Glu Ala Asn Lys Tyr Gln Ile Ser
            355                 360                 365

Val Asn Lys Tyr Arg Gly Thr Ala Gly Asn Ala Leu Met Asp Gly Ala
    370                 375                 380

Ser Gln Leu Met Gly Glu Asn Arg Thr Met Thr Ile His Asn Gly Met
385                 390                 395                 400

Phe Phe Ser Thr Tyr Asp Arg Asp Asn Asp Gly Trp Leu Thr Ser Asp
                405                 410                 415

Pro Arg Lys Gln Cys Ser Lys Glu Asp Gly Gly Trp Trp Tyr Asn
            420                 425                 430

Arg Cys His Ala Ala Asn Pro Asn Gly Arg Tyr Tyr Trp Gly Gly Gln
        435                 440                 445

Tyr Thr Trp Asp Met Ala Lys His Gly Thr Asp Asp Gly Val Val Trp
    450                 455                 460

Met Asn Trp Lys Gly Ser Trp Tyr Ser Met Arg Lys Met Ser Met Lys
465                 470                 475                 480

Ile Arg Pro Phe Phe Pro Gln Gln
                485

<210> SEQ ID NO 3
<211> LENGTH: 453
<212> TYPE: PRT
<213> ORGANISM: Homo sapiens

<400> SEQUENCE: 3

Met Ser Trp Ser Leu His Pro Arg Asn Leu Ile Leu Tyr Phe Tyr Ala
1               5                   10                  15

Leu Leu Phe Leu Ser Ser Thr Cys Val Ala Tyr Val Ala Thr Arg Asp
                20                  25                  30

Asn Cys Cys Ile Leu Asp Glu Arg Phe Gly Ser Tyr Cys Pro Thr Thr
            35                  40                  45

Cys Gly Ile Ala Asp Phe Leu Ser Thr Tyr Gln Thr Lys Val Asp Lys
        50                  55                  60

Asp Leu Gln Ser Leu Glu Asp Ile Leu His Gln Val Glu Asn Lys Thr
65                  70                  75                  80

Ser Glu Val Lys Gln Leu Ile Lys Ala Ile Gln Leu Thr Tyr Asn Pro
                85                  90                  95

Asp Glu Ser Ser Lys Pro Asn Met Ile Asp Ala Ala Thr Leu Lys Ser
            100                 105                 110

Arg Lys Met Leu Glu Glu Ile Met Lys Tyr Glu Ala Ser Ile Leu Thr
        115                 120                 125

His Asp Ser Ser Ile Arg Tyr Leu Gln Glu Ile Tyr Asn Ser Asn Asn
130                 135                 140

Gln Lys Ile Val Asn Leu Lys Glu Lys Val Ala Gln Leu Glu Ala Gln
145                 150                 155                 160

Cys Gln Glu Pro Cys Lys Asp Thr Val Gln Ile His Asp Ile Thr Gly
                165                 170                 175

Lys Asp Cys Gln Asp Ile Ala Asn Lys Gly Ala Lys Gln Ser Gly Leu
            180                 185                 190

Tyr Phe Ile Lys Pro Leu Lys Ala Asn Gln Gln Phe Leu Val Tyr Cys
        195                 200                 205

Glu Ile Asp Gly Ser Gly Asn Gly Trp Thr Val Phe Gln Lys Arg Leu
210                 215                 220

Asp Gly Ser Val Asp Phe Lys Lys Asn Trp Ile Gln Tyr Lys Glu Gly
225                 230                 235                 240
```

```
Phe Gly His Leu Ser Pro Thr Gly Thr Thr Glu Phe Trp Leu Gly Asn
                245                 250                 255

Glu Lys Ile His Leu Ile Ser Thr Gln Ser Ala Ile Pro Tyr Ala Leu
            260                 265                 270

Arg Val Glu Leu Glu Asp Trp Asn Gly Arg Thr Ser Thr Ala Asp Tyr
        275                 280                 285

Ala Met Phe Lys Val Gly Pro Glu Ala Asp Lys Tyr Arg Leu Thr Tyr
    290                 295                 300

Ala Tyr Phe Ala Gly Gly Asp Ala Gly Asp Ala Phe Asp Gly Phe Asp
305                 310                 315                 320

Phe Gly Asp Asp Pro Ser Asp Lys Phe Phe Thr Ser His Asn Gly Met
                325                 330                 335

Gln Phe Ser Thr Trp Asp Asn Asp Asn Asp Lys Phe Glu Gly Asn Cys
            340                 345                 350

Ala Glu Gln Asp Gly Ser Gly Trp Trp Met Asn Lys Cys His Ala Gly
        355                 360                 365

His Leu Asn Gly Val Tyr Tyr Gln Gly Gly Thr Tyr Ser Lys Ala Ser
    370                 375                 380

Thr Pro Asn Gly Tyr Asp Asn Gly Ile Ile Trp Ala Thr Trp Lys Thr
385                 390                 395                 400

Arg Trp Tyr Ser Met Lys Lys Thr Thr Met Lys Ile Ile Pro Phe Asn
                405                 410                 415

Arg Leu Thr Ile Gly Glu Gly Gln Gln His Leu Gly Gly Ala Lys
            420                 425                 430

Gln Val Arg Pro Glu His Pro Ala Glu Thr Glu Tyr Asp Ser Leu Tyr
        435                 440                 445

Pro Glu Asp Asp Leu
    450

<210> SEQ ID NO 4
<211> LENGTH: 21
<212> TYPE: PRT
<213> ORGANISM: Homo sapiens

<400> SEQUENCE: 4

Arg Val Val Glu Arg His Gln Ser Ala Cys Lys Asp Ser Asp Trp Pro
1               5                   10                  15

Phe Cys Ser Asp Glu
            20

<210> SEQ ID NO 5
<211> LENGTH: 21
<212> TYPE: PRT
<213> ORGANISM: artificial
<220> FEATURE:
<223> OTHER INFORMATION: homocitrulline containing Fibrinogen alpha
      counterpart
<220> FEATURE:
<221> NAME/KEY: MISC_FEATURE
<222> LOCATION: (11)..(11)
<223> OTHER INFORMATION: homocitrulline

<400> SEQUENCE: 5

Arg Val Val Glu Arg His Gln Ser Ala Cys Xaa Asp Ser Asp Trp Pro
1               5                   10                  15

Phe Cys Ser Asp Glu
            20
```

```
<210> SEQ ID NO 6
<211> LENGTH: 21
<212> TYPE: PRT
<213> ORGANISM: Homo sapiens

<400> SEQUENCE: 6

Pro Phe Cys Ser Asp Glu Asp Trp Asn Tyr Lys Cys Pro Ser Gly Cys
1               5                   10                  15

Arg Met Lys Gly Leu
            20

<210> SEQ ID NO 7
<211> LENGTH: 21
<212> TYPE: PRT
<213> ORGANISM: artificial
<220> FEATURE:
<223> OTHER INFORMATION: homocitrulline containing Fibrinogen alpha
      counterpart
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: misc_feature
<222> LOCATION: (19)..(19)
<223> OTHER INFORMATION: Xaa can be any naturally occurring amino acid

<400> SEQUENCE: 7

Pro Phe Cys Ser Asp Glu Asp Trp Asn Tyr Xaa Cys Pro Ser Gly Cys
1               5                   10                  15

Arg Met Xaa Gly Leu
            20

<210> SEQ ID NO 8
<211> LENGTH: 21
<212> TYPE: PRT
<213> ORGANISM: homo sapiens

<400> SEQUENCE: 8

Asn Tyr Lys Cys Pro Ser Gly Cys Arg Met Lys Gly Leu Ile Asp Glu
1               5                   10                  15

Val Asn Gln Asp Phe
            20

<210> SEQ ID NO 9
<211> LENGTH: 21
<212> TYPE: PRT
<213> ORGANISM: artificial
<220> FEATURE:
<223> OTHER INFORMATION: homocitrulline containing Fibrinogen alpha
      counterpart
<220> FEATURE:
<221> NAME/KEY: MISC_FEATURE
<222> LOCATION: (3)..(3)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline

<400> SEQUENCE: 9

Asn Tyr Xaa Cys Pro Ser Gly Cys Arg Met Xaa Gly Leu Ile Asp Glu
1               5                   10                  15

Val Asn Gln Asp Phe
            20

<210> SEQ ID NO 10
```

```
<211> LENGTH: 21
<212> TYPE: PRT
<213> ORGANISM: homo sapiens

<400> SEQUENCE: 10

Val Asn Gln Asp Phe Thr Asn Arg Ile Asn Lys Leu Lys Asn Ser Leu
1               5                   10                  15

Phe Glu Tyr Gln Lys
            20

<210> SEQ ID NO 11
<211> LENGTH: 21
<212> TYPE: PRT
<213> ORGANISM: artificial
<220> FEATURE:
<223> OTHER INFORMATION: homocitrulline containing Fibrinogen alpha
      counterpart
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (13)..(13)
<223> OTHER INFORMATION: homocitrulline
<220> FEATURE:
<221> NAME/KEY: MISC_FEATURE
<222> LOCATION: (21)..(21)
<223> OTHER INFORMATION: homocitrulline

<400> SEQUENCE: 11

Val Asn Gln Asp Phe Thr Asn Arg Ile Asn Xaa Leu Xaa Asn Ser Leu
1               5                   10                  15

Phe Glu Tyr Gln Xaa
            20

<210> SEQ ID NO 12
<211> LENGTH: 21
<212> TYPE: PRT
<213> ORGANISM: homo sapiens

<400> SEQUENCE: 12

Gln Asp Phe Thr Asn Arg Ile Asn Lys Leu Lys Asn Ser Leu Phe Glu
1               5                   10                  15

Tyr Gln Lys Asn Asn
            20

<210> SEQ ID NO 13
<211> LENGTH: 21
<212> TYPE: PRT
<213> ORGANISM: Artificial
<220> FEATURE:
<223> OTHER INFORMATION: homocitrulline containing Fibrinogen alpha
      counterpart
<220> FEATURE:
<221> NAME/KEY: MISC_FEATURE
<222> LOCATION: (9)..(9)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (19)..(19)
<223> OTHER INFORMATION: homocitrulline

<400> SEQUENCE: 13

Gln Asp Phe Thr Asn Arg Ile Asn Xaa Leu Xaa Asn Ser Leu Phe Glu
```

```
1               5                   10                  15

Tyr Gln Xaa Asn Asn
            20

<210> SEQ ID NO 14
<211> LENGTH: 21
<212> TYPE: PRT
<213> ORGANISM: homo sapiens

<400> SEQUENCE: 14

Lys Leu Lys Asn Ser Leu Phe Glu Tyr Gln Lys Asn Asn Lys Asp Ser
1               5                   10                  15

His Ser Leu Thr Thr
            20

<210> SEQ ID NO 15
<211> LENGTH: 21
<212> TYPE: PRT
<213> ORGANISM: artificial
<220> FEATURE:
<223> OTHER INFORMATION: homocitrulline containing Fibrinogen alpha
      counterpart
<220> FEATURE:
<221> NAME/KEY: MISC_FEATURE
<222> LOCATION: (1)..(1)
<223> OTHER INFORMATION: homocitrulline
<220> FEATURE:
<221> NAME/KEY: MISC_FEATURE
<222> LOCATION: (3)..(3)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (14)..(14)
<223> OTHER INFORMATION: homocitrulline

<400> SEQUENCE: 15

Xaa Leu Xaa Asn Ser Leu Phe Glu Tyr Gln Xaa Asn Asn Xaa Asp Ser
1               5                   10                  15

His Ser Leu Thr Thr
            20

<210> SEQ ID NO 16
<211> LENGTH: 21
<212> TYPE: PRT
<213> ORGANISM: homo sapiens

<400> SEQUENCE: 16

Asn Ser Leu Phe Glu Tyr Gln Lys Asn Asn Lys Asp Ser His Ser Leu
1               5                   10                  15

Thr Thr Asn Ile Met
            20

<210> SEQ ID NO 17
<211> LENGTH: 21
<212> TYPE: PRT
<213> ORGANISM: artificial
<220> FEATURE:
<223> OTHER INFORMATION: homocitrulline containing Fibrinogen alpha
      counterpart
<220> FEATURE:
<221> NAME/KEY: MISC_FEATURE
<222> LOCATION: (8)..(8)
<223> OTHER INFORMATION: homocitrulline
<220> FEATURE:
```

```
<221> NAME/KEY: MISC_FEATURE
<222> LOCATION: (11)..(11)
<223> OTHER INFORMATION: homocitrulline

<400> SEQUENCE: 17

Asn Ser Leu Phe Glu Tyr Gln Xaa Asn Asn Xaa Asp Ser His Ser Leu
1               5                   10                  15

Thr Thr Asn Ile Met
            20

<210> SEQ ID NO 18
<211> LENGTH: 21
<212> TYPE: PRT
<213> ORGANISM: homo sapiens

<400> SEQUENCE: 18

Glu Asp Leu Arg Ser Arg Ile Glu Val Leu Lys Arg Lys Val Ile Glu
1               5                   10                  15

Lys Val Gln His Ile
            20

<210> SEQ ID NO 19
<211> LENGTH: 21
<212> TYPE: PRT
<213> ORGANISM: artificial
<220> FEATURE:
<223> OTHER INFORMATION: homocitrulline containing Fibrinogen alpha
      counterpart
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (13)..(13)
<223> OTHER INFORMATION: homocitrulline
<220> FEATURE:
<221> NAME/KEY: MISC_FEATURE
<222> LOCATION: (17)..(17)
<223> OTHER INFORMATION: homocitrulline

<400> SEQUENCE: 19

Glu Asp Leu Arg Ser Arg Ile Glu Val Leu Xaa Arg Xaa Val Ile Glu
1               5                   10                  15

Xaa Val Gln His Ile
            20

<210> SEQ ID NO 20
<211> LENGTH: 21
<212> TYPE: PRT
<213> ORGANISM: homo sapiens

<400> SEQUENCE: 20

Leu Arg Ser Arg Ile Glu Val Leu Lys Arg Lys Val Ile Glu Lys Val
1               5                   10                  15

Gln His Ile Gln Leu
            20

<210> SEQ ID NO 21
<211> LENGTH: 21
<212> TYPE: PRT
<213> ORGANISM: artificial
<220> FEATURE:
<223> OTHER INFORMATION: homocitrulline containing Fibrinogen alpha
      counterpart
<220> FEATURE:
<221> NAME/KEY: MISC_FEATURE
```

```
<222> LOCATION: (9)..(9)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (15)..(15)
<223> OTHER INFORMATION: homocitrulline

<400> SEQUENCE: 21

Leu Arg Ser Arg Ile Glu Val Leu Xaa Arg Xaa Val Ile Glu Xaa Val
1               5                  10                  15

Gln His Ile Gln Leu
            20

<210> SEQ ID NO 22
<211> LENGTH: 21
<212> TYPE: PRT
<213> ORGANISM: homo sapiens

<400> SEQUENCE: 22

Ile Glu Val Leu Lys Arg Lys Val Ile Glu Lys Val Gln His Ile Gln
1               5                  10                  15

Leu Leu Gln Lys Asn
            20

<210> SEQ ID NO 23
<211> LENGTH: 21
<212> TYPE: PRT
<213> ORGANISM: artificial
<220> FEATURE:
<223> OTHER INFORMATION: homocitrulline containing Fibrinogen alpha
      counterpart
<220> FEATURE:
<221> NAME/KEY: MISC_FEATURE
<222> LOCATION: (5)..(5)
<223> OTHER INFORMATION: homocitrulline
<220> FEATURE:
<221> NAME/KEY: MISC_FEATURE
<222> LOCATION: (7)..(7)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (20)..(20)
<223> OTHER INFORMATION: homocitrulline

<400> SEQUENCE: 23

Ile Glu Val Leu Xaa Arg Xaa Val Ile Glu Xaa Val Gln His Ile Gln
1               5                  10                  15

Leu Leu Gln Xaa Asn
            20

<210> SEQ ID NO 24
<211> LENGTH: 21
<212> TYPE: PRT
<213> ORGANISM: homo sapiens

<400> SEQUENCE: 24

Glu Lys Val Gln His Ile Gln Leu Leu Gln Lys Asn Val Arg Ala Gln
1               5                  10                  15

Leu Val Asp Met Lys
            20
```

<210> SEQ ID NO 25
<211> LENGTH: 21
<212> TYPE: PRT
<213> ORGANISM: artificial
<220> FEATURE:
<223> OTHER INFORMATION: homocitrulline containing Fibrinogen alpha
      counterpart
<220> FEATURE:
<221> NAME/KEY: MISC_FEATURE
<222> LOCATION: (2)..(2)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (21)..(21)
<223> OTHER INFORMATION: homocitrulline

<400> SEQUENCE: 25

Glu Xaa Val Gln His Ile Gln Leu Leu Gln Xaa Asn Val Arg Ala Gln
1               5                   10                  15

Leu Val Asp Met Xaa
            20

<210> SEQ ID NO 26
<211> LENGTH: 21
<212> TYPE: PRT
<213> ORGANISM: homo sapiens

<400> SEQUENCE: 26

Lys Asn Val Arg Ala Gln Leu Val Asp Met Lys Arg Leu Glu Val Asp
1               5                   10                  15

Ile Asp Ile Lys Ile
            20

<210> SEQ ID NO 27
<211> LENGTH: 21
<212> TYPE: PRT
<213> ORGANISM: artificial
<220> FEATURE:
<223> OTHER INFORMATION: homocitrulline containing Fibrinogen alpha
      counterpart
<220> FEATURE:
<221> NAME/KEY: MISC_FEATURE
<222> LOCATION: (1)..(1)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (20)..(20)
<223> OTHER INFORMATION: homocitrulline

<400> SEQUENCE: 27

Xaa Asn Val Arg Ala Gln Leu Val Asp Met Xaa Arg Leu Glu Val Asp
1               5                   10                  15

Ile Asp Ile Xaa Ile
            20

<210> SEQ ID NO 28
<211> LENGTH: 21
<212> TYPE: PRT
<213> ORGANISM: homo sapiens

```
<400> SEQUENCE: 28

Met Lys Arg Leu Glu Val Asp Ile Asp Ile Lys Ile Arg Ser Cys Arg
1               5                   10                  15

Gly Ser Cys Ser Arg
            20

<210> SEQ ID NO 29
<211> LENGTH: 21
<212> TYPE: PRT
<213> ORGANISM: artificial
<220> FEATURE:
<223> OTHER INFORMATION: homocitrulline containing Fibrinogen alpha
      counterpart
<220> FEATURE:
<221> NAME/KEY: MISC_FEATURE
<222> LOCATION: (2)..(2)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline

<400> SEQUENCE: 29

Met Xaa Arg Leu Glu Val Asp Ile Asp Ile Xaa Ile Arg Ser Cys Arg
1               5                   10                  15

Gly Ser Cys Ser Arg
            20

<210> SEQ ID NO 30
<211> LENGTH: 21
<212> TYPE: PRT
<213> ORGANISM: homo sapiens

<400> SEQUENCE: 30

Ser Arg Ala Leu Ala Arg Glu Val Asp Leu Lys Asp Tyr Glu Asp Gln
1               5                   10                  15

Gln Lys Gln Leu Glu
            20

<210> SEQ ID NO 31
<211> LENGTH: 21
<212> TYPE: PRT
<213> ORGANISM: artificial
<220> FEATURE:
<223> OTHER INFORMATION: homocitrulline containing Fibrinogen alpha
      counterpart
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (18)..(18)
<223> OTHER INFORMATION: homocitrulline

<400> SEQUENCE: 31

Ser Arg Ala Leu Ala Arg Glu Val Asp Leu Xaa Asp Tyr Glu Asp Gln
1               5                   10                  15

Gln Xaa Gln Leu Glu
            20

<210> SEQ ID NO 32
<211> LENGTH: 21
<212> TYPE: PRT
<213> ORGANISM: homo sapiens

<400> SEQUENCE: 32
```

-continued

Val Asp Leu Lys Asp Tyr Glu Asp Gln Gln Lys Gln Leu Glu Gln Val
1               5                   10                  15

Ile Ala Lys Asp Leu
            20

<210> SEQ ID NO 33
<211> LENGTH: 21
<212> TYPE: PRT
<213> ORGANISM: artificial
<220> FEATURE:
<223> OTHER INFORMATION: homocitrulline containing Fibrinogen alpha
      counterpart
<220> FEATURE:
<221> NAME/KEY: MISC_FEATURE
<222> LOCATION: (4)..(4)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (19)..(19)
<223> OTHER INFORMATION: homocitrulline

<400> SEQUENCE: 33

Val Asp Leu Xaa Asp Tyr Glu Asp Gln Gln Xaa Gln Leu Glu Gln Val
1               5                   10                  15

Ile Ala Xaa Asp Leu
            20

<210> SEQ ID NO 34
<211> LENGTH: 21
<212> TYPE: PRT
<213> ORGANISM: homo sapiens

<400> SEQUENCE: 34

Gln Gln Lys Gln Leu Glu Gln Val Ile Ala Lys Asp Leu Leu Pro Ser
1               5                   10                  15

Arg Asp Arg Gln His
            20

<210> SEQ ID NO 35
<211> LENGTH: 21
<212> TYPE: PRT
<213> ORGANISM: artificial
<220> FEATURE:
<223> OTHER INFORMATION: homocitrulline containing Fibrinogen alpha
      counterpart
<220> FEATURE:
<221> NAME/KEY: MISC_FEATURE
<222> LOCATION: (3)..(3)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline

<400> SEQUENCE: 35

Gln Gln Xaa Gln Leu Glu Gln Val Ile Ala Xaa Asp Leu Leu Pro Ser
1               5                   10                  15

Arg Asp Arg Gln His
            20

<210> SEQ ID NO 36
<211> LENGTH: 21
<212> TYPE: PRT

<213> ORGANISM: homo sapiens

<400> SEQUENCE: 36

Ser Arg Asp Arg Gln His Leu Pro Leu Ile Lys Met Lys Pro Val Pro
1               5                   10                  15

Asp Leu Val Pro Gly
            20

<210> SEQ ID NO 37
<211> LENGTH: 21
<212> TYPE: PRT
<213> ORGANISM: artificial
<220> FEATURE:
<223> OTHER INFORMATION: homocitrulline containing Fibrinogen alpha
      counterpart
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (13)..(13)
<223> OTHER INFORMATION: homocitrulline

<400> SEQUENCE: 37

Ser Arg Asp Arg Gln His Leu Pro Leu Ile Xaa Met Xaa Pro Val Pro
1               5                   10                  15

Asp Leu Val Pro Gly
            20

<210> SEQ ID NO 38
<211> LENGTH: 21
<212> TYPE: PRT
<213> ORGANISM: homo sapiens

<400> SEQUENCE: 38

Asp Arg Gln His Leu Pro Leu Ile Lys Met Lys Pro Val Pro Asp Leu
1               5                   10                  15

Val Pro Gly Asn Phe
            20

<210> SEQ ID NO 39
<211> LENGTH: 21
<212> TYPE: PRT
<213> ORGANISM: artificial
<220> FEATURE:
<223> OTHER INFORMATION: homocitrulline containing Fibrinogen alpha
      counterpart
<220> FEATURE:
<221> NAME/KEY: MISC_FEATURE
<222> LOCATION: (8)..(8)
<223> OTHER INFORMATION: homocitrulline
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: MISC_FEATURE
<222> LOCATION: (11)..(11)
<223> OTHER INFORMATION: homocitrulline

<400> SEQUENCE: 39

Asp Arg Gln His Leu Pro Leu Ile Xaa Met Xaa Pro Val Pro Asp Leu
1               5                   10                  15

Val Pro Gly Asn Phe
            20

```
<210> SEQ ID NO 40
<211> LENGTH: 21
<212> TYPE: PRT
<213> ORGANISM: homo sapiens

<400> SEQUENCE: 40

Pro Val Pro Asp Leu Val Pro Gly Asn Phe Lys Ser Gln Leu Gln Lys
1               5                   10                  15

Val Pro Pro Glu Trp
            20

<210> SEQ ID NO 41
<211> LENGTH: 21
<212> TYPE: PRT
<213> ORGANISM: Artificial
<220> FEATURE:
<223> OTHER INFORMATION: homocitrulline containing Fibrinogen alpha
      counterpart
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (16)..(16)
<223> OTHER INFORMATION: homocitrulline

<400> SEQUENCE: 41

Pro Val Pro Asp Leu Val Pro Gly Asn Phe Xaa Ser Gln Leu Gln Xaa
1               5                   10                  15

Val Pro Pro Glu Trp
            20

<210> SEQ ID NO 42
<211> LENGTH: 21
<212> TYPE: PRT
<213> ORGANISM: homo sapiens

<400> SEQUENCE: 42

Val Pro Gly Asn Phe Lys Ser Gln Leu Gln Lys Val Pro Pro Glu Trp
1               5                   10                  15

Lys Ala Leu Thr Asp
            20

<210> SEQ ID NO 43
<211> LENGTH: 21
<212> TYPE: PRT
<213> ORGANISM: artificial
<220> FEATURE:
<223> OTHER INFORMATION: homocitrulline containing Fibrinogen alpha
      counterpart
<220> FEATURE:
<221> NAME/KEY: MISC_FEATURE
<222> LOCATION: (6)..(6)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (17)..(17)
<223> OTHER INFORMATION: homocitrulline

<400> SEQUENCE: 43

Val Pro Gly Asn Phe Xaa Ser Gln Leu Gln Xaa Val Pro Pro Glu Trp
1               5                   10                  15

Xaa Ala Leu Thr Asp
```

-continued

```
<210> SEQ ID NO 44
<211> LENGTH: 21
<212> TYPE: PRT
<213> ORGANISM: homo sapiens

<400> SEQUENCE: 44

Ser Gln Leu Gln Lys Val Pro Pro Glu Trp Lys Ala Leu Thr Asp Met
1               5                   10                  15

Pro Gln Met Arg Met
            20

<210> SEQ ID NO 45
<211> LENGTH: 21
<212> TYPE: PRT
<213> ORGANISM: artificial
<220> FEATURE:
<223> OTHER INFORMATION: homocitrulline containing Fibrinogen alpha
      counterpart
<220> FEATURE:
<221> NAME/KEY: MISC_FEATURE
<222> LOCATION: (5)..(5)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline

<400> SEQUENCE: 45

Ser Gln Leu Gln Xaa Val Pro Pro Glu Trp Xaa Ala Leu Thr Asp Met
1               5                   10                  15

Pro Gln Met Arg Met
            20

<210> SEQ ID NO 46
<211> LENGTH: 21
<212> TYPE: PRT
<213> ORGANISM: homo sapiens

<400> SEQUENCE: 46

Ser Ser Gly Thr Gly Gly Thr Ala Thr Trp Lys Pro Gly Ser Ser Gly
1               5                   10                  15

Pro Gly Ser Thr Gly
            20

<210> SEQ ID NO 47
<211> LENGTH: 21
<212> TYPE: PRT
<213> ORGANISM: artificial
<220> FEATURE:
<223> OTHER INFORMATION: homocitrulline containing Fibrinogen alpha
      counterpart
<220> FEATURE:
<221> NAME/KEY: MISC_FEATURE
<222> LOCATION: (11)..(11)
<223> OTHER INFORMATION: homocitrulline

<400> SEQUENCE: 47

Ser Ser Gly Thr Gly Gly Thr Ala Thr Trp Xaa Pro Gly Ser Ser Gly
1               5                   10                  15

Pro Gly Ser Thr Gly
            20

<210> SEQ ID NO 48
<211> LENGTH: 21
```

```
<212> TYPE: PRT
<213> ORGANISM: homo sapiens

<400> SEQUENCE: 48

Pro Gly Thr Arg Arg Glu Tyr His Thr Glu Lys Leu Val Thr Ser Lys
1               5                   10                  15

Gly Asp Lys Glu Leu
            20

<210> SEQ ID NO 49
<211> LENGTH: 21
<212> TYPE: PRT
<213> ORGANISM: artificial
<220> FEATURE:
<223> OTHER INFORMATION: homocitrulline containing Fibrinogen alpha
      counterpart
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (16)..(16)
<223> OTHER INFORMATION: homocitrulline
<220> FEATURE:
<221> NAME/KEY: MISC_FEATURE
<222> LOCATION: (19)..(19)
<223> OTHER INFORMATION: homocitrulline

<400> SEQUENCE: 49

Pro Gly Thr Arg Arg Glu Tyr His Thr Glu Xaa Leu Val Thr Ser Xaa
1               5                   10                  15

Gly Asp Xaa Glu Leu
            20

<210> SEQ ID NO 50
<211> LENGTH: 21
<212> TYPE: PRT
<213> ORGANISM: homo sapiens

<400> SEQUENCE: 50

Glu Tyr His Thr Glu Lys Leu Val Thr Ser Lys Gly Asp Lys Glu Leu
1               5                   10                  15

Arg Thr Gly Lys Glu
            20

<210> SEQ ID NO 51
<211> LENGTH: 21
<212> TYPE: PRT
<213> ORGANISM: artificial
<220> FEATURE:
<223> OTHER INFORMATION: homocitrulline containing Fibrinogen alpha
      counterpart
<220> FEATURE:
<221> NAME/KEY: MISC_FEATURE
<222> LOCATION: (6)..(6)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (14)..(14)
<223> OTHER INFORMATION: homocitrulline
<220> FEATURE:
<221> NAME/KEY: MISC_FEATURE
<222> LOCATION: (20)..(20)
<223> OTHER INFORMATION: homocitrulline
```

```
<400> SEQUENCE: 51

Glu Tyr His Thr Glu Xaa Leu Val Thr Ser Xaa Gly Asp Xaa Glu Leu
1               5                   10                  15

Arg Thr Gly Xaa Glu
            20

<210> SEQ ID NO 52
<211> LENGTH: 21
<212> TYPE: PRT
<213> ORGANISM: homo sapiens

<400> SEQUENCE: 52

Thr Glu Lys Leu Val Thr Ser Lys Gly Asp Lys Glu Leu Arg Thr Gly
1               5                   10                  15

Lys Glu Lys Val Thr
            20

<210> SEQ ID NO 53
<211> LENGTH: 21
<212> TYPE: PRT
<213> ORGANISM: artificial
<220> FEATURE:
<223> OTHER INFORMATION: homocitrulline containing Fibrinogen alpha
      counterpart
<220> FEATURE:
<221> NAME/KEY: MISC_FEATURE
<222> LOCATION: (3)..(3)
<223> OTHER INFORMATION: homocitrulline
<220> FEATURE:
<221> NAME/KEY: MISC_FEATURE
<222> LOCATION: (8)..(8)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (17)..(17)
<223> OTHER INFORMATION: homocitrulline
<220> FEATURE:
<221> NAME/KEY: MISC_FEATURE
<222> LOCATION: (19)..(19)
<223> OTHER INFORMATION: homocitrulline

<400> SEQUENCE: 53

Thr Glu Xaa Leu Val Thr Ser Xaa Gly Asp Xaa Glu Leu Arg Thr Gly
1               5                   10                  15

Xaa Glu Xaa Val Thr
            20

<210> SEQ ID NO 54
<211> LENGTH: 21
<212> TYPE: PRT
<213> ORGANISM: homo sapiens

<400> SEQUENCE: 54

Ser Lys Gly Asp Lys Glu Leu Arg Thr Gly Lys Glu Lys Val Thr Ser
1               5                   10                  15

Gly Ser Thr Thr Thr
            20

<210> SEQ ID NO 55
<211> LENGTH: 21
<212> TYPE: PRT
<213> ORGANISM: artificial
<220> FEATURE:
```

```
<223> OTHER INFORMATION: homocitrulline containing Fibrinogen alpha
      counterpart
<220> FEATURE:
<221> NAME/KEY: MISC_FEATURE
<222> LOCATION: (2)..(2)
<223> OTHER INFORMATION: homocitrulline
<220> FEATURE:
<221> NAME/KEY: MISC_FEATURE
<222> LOCATION: (5)..(5)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (13)..(13)
<223> OTHER INFORMATION: homocitrulline

<400> SEQUENCE: 55

Ser Xaa Gly Asp Xaa Glu Leu Arg Thr Gly Xaa Glu Xaa Val Thr Ser
1               5                   10                  15

Gly Ser Thr Thr Thr
            20

<210> SEQ ID NO 56
<211> LENGTH: 21
<212> TYPE: PRT
<213> ORGANISM: homo sapiens

<400> SEQUENCE: 56

Gly Asp Lys Glu Leu Arg Thr Gly Lys Glu Lys Val Thr Ser Gly Ser
1               5                   10                  15

Thr Thr Thr Thr Arg
            20

<210> SEQ ID NO 57
<211> LENGTH: 21
<212> TYPE: PRT
<213> ORGANISM: artificial
<220> FEATURE:
<223> OTHER INFORMATION: homocitrulline containing Fibrinogen alpha
      counterpart
<220> FEATURE:
<221> NAME/KEY: MISC_FEATURE
<222> LOCATION: (3)..(3)
<223> OTHER INFORMATION: homocitrulline
<220> FEATURE:
<221> NAME/KEY: MISC_FEATURE
<222> LOCATION: (9)..(9)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline

<400> SEQUENCE: 57

Gly Asp Xaa Glu Leu Arg Thr Gly Xaa Glu Xaa Val Thr Ser Gly Ser
1               5                   10                  15

Thr Thr Thr Thr Arg
            20

<210> SEQ ID NO 58
<211> LENGTH: 21
<212> TYPE: PRT
<213> ORGANISM: homo sapiens

<400> SEQUENCE: 58

Ser Thr Thr Thr Thr Arg Arg Ser Cys Ser Lys Thr Val Thr Lys Thr
```

```
1               5                  10                 15

Val Ile Gly Pro Asp
            20

<210> SEQ ID NO 59
<211> LENGTH: 21
<212> TYPE: PRT
<213> ORGANISM: artificial
<220> FEATURE:
<223> OTHER INFORMATION: homocitrulline containing Fibrinogen alpha
      counterpart
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (15)..(15)
<223> OTHER INFORMATION: homocitrulline

<400> SEQUENCE: 59

Ser Thr Thr Thr Thr Arg Arg Ser Cys Ser Xaa Thr Val Thr Xaa Thr
1               5                  10                 15

Val Ile Gly Pro Asp
            20

<210> SEQ ID NO 60
<211> LENGTH: 21
<212> TYPE: PRT
<213> ORGANISM: homo sapiens

<400> SEQUENCE: 60

Thr Arg Arg Ser Cys Ser Lys Thr Val Thr Lys Thr Val Ile Gly Pro
1               5                  10                 15

Asp Gly His Lys Glu
            20

<210> SEQ ID NO 61
<211> LENGTH: 21
<212> TYPE: PRT
<213> ORGANISM: artificial
<220> FEATURE:
<223> OTHER INFORMATION: homocitrulline containing Fibrinogen alpha
      counterpart
<220> FEATURE:
<221> NAME/KEY: MISC_FEATURE
<222> LOCATION: (7)..(7)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (20)..(20)
<223> OTHER INFORMATION: homocitrulline

<400> SEQUENCE: 61

Thr Arg Arg Ser Cys Ser Xaa Thr Val Thr Xaa Thr Val Ile Gly Pro
1               5                  10                 15

Asp Gly His Xaa Glu
            20

<210> SEQ ID NO 62
<211> LENGTH: 21
<212> TYPE: PRT
<213> ORGANISM: homo sapiens
```

```
<400> SEQUENCE: 62

Thr Lys Thr Val Ile Gly Pro Asp Gly His Lys Glu Val Thr Lys Glu
1               5                   10                  15

Val Val Thr Ser Glu
            20

<210> SEQ ID NO 63
<211> LENGTH: 21
<212> TYPE: PRT
<213> ORGANISM: artificial
<220> FEATURE:
<223> OTHER INFORMATION: homocitrulline containing Fibrinogen alpha
      counterpart
<220> FEATURE:
<221> NAME/KEY: MISC_FEATURE
<222> LOCATION: (2)..(2)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (15)..(15)
<223> OTHER INFORMATION: homocitrulline

<400> SEQUENCE: 63

Thr Xaa Thr Val Ile Gly Pro Asp Gly His Xaa Glu Val Thr Xaa Glu
1               5                   10                  15

Val Val Thr Ser Glu
            20

<210> SEQ ID NO 64
<211> LENGTH: 21
<212> TYPE: PRT
<213> ORGANISM: homo sapiens

<400> SEQUENCE: 64

Ile Gly Pro Asp Gly His Lys Glu Val Thr Lys Glu Val Val Thr Ser
1               5                   10                  15

Glu Asp Gly Ser Asp
            20

<210> SEQ ID NO 65
<211> LENGTH: 21
<212> TYPE: PRT
<213> ORGANISM: artificial
<220> FEATURE:
<223> OTHER INFORMATION: homocitrulline containing Fibrinogen alpha
      counterpart
<220> FEATURE:
<221> NAME/KEY: MISC_FEATURE
<222> LOCATION: (6)..(6)
<223> OTHER INFORMATION: homocitrulline
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: MISC_FEATURE
<222> LOCATION: (11)..(11)
<223> OTHER INFORMATION: homocitrulline

<400> SEQUENCE: 65

Ile Gly Pro Asp Gly Xaa Xaa Glu Val Thr Xaa Glu Val Val Thr Ser
1               5                   10                  15

Glu Asp Gly Ser Asp
            20
```

```
<210> SEQ ID NO 66
<211> LENGTH: 21
<212> TYPE: PRT
<213> ORGANISM: homo sapiens

<400> SEQUENCE: 66

Ala Ala Phe Phe Asp Thr Ala Ser Thr Gly Lys Thr Phe Pro Gly Phe
1               5                   10                  15

Phe Ser Pro Met Leu
            20

<210> SEQ ID NO 67
<211> LENGTH: 21
<212> TYPE: PRT
<213> ORGANISM: artificial
<220> FEATURE:
<223> OTHER INFORMATION: homocitrulline containing Fibrinogen alpha
      counterpart
<220> FEATURE:
<221> NAME/KEY: MISC_FEATURE
<222> LOCATION: (11)..(11)
<223> OTHER INFORMATION: homocitrulline

<400> SEQUENCE: 67

Ala Ala Phe Phe Asp Thr Ala Ser Thr Gly Xaa Thr Phe Pro Gly Phe
1               5                   10                  15

Phe Ser Pro Met Leu
            20

<210> SEQ ID NO 68
<211> LENGTH: 21
<212> TYPE: PRT
<213> ORGANISM: homo sapiens

<400> SEQUENCE: 68

Gly Ser Glu Ser Gly Ile Phe Thr Asn Thr Lys Glu Ser Ser Ser His
1               5                   10                  15

His Pro Gly Ile Ala
            20

<210> SEQ ID NO 69
<211> LENGTH: 21
<212> TYPE: PRT
<213> ORGANISM: artificial
<220> FEATURE:
<223> OTHER INFORMATION: homocitrulline containing Fibrinogen alpha
      counterpart
<220> FEATURE:
<221> NAME/KEY: MISC_FEATURE
<222> LOCATION: (11)..(11)
<223> OTHER INFORMATION: homocitrulline

<400> SEQUENCE: 69

Gly Ser Glu Ser Gly Ile Phe Thr Asn Thr Xaa Glu Ser Ser Ser His
1               5                   10                  15

His Pro Gly Ile Ala
            20

<210> SEQ ID NO 70
<211> LENGTH: 21
<212> TYPE: PRT
<213> ORGANISM: homo sapiens

<400> SEQUENCE: 70
```

```
Pro Gly Ile Ala Glu Phe Pro Ser Arg Gly Lys Ser Ser Ser Tyr Ser
1               5                   10                  15

Lys Gln Phe Thr Ser
            20

<210> SEQ ID NO 71
<211> LENGTH: 21
<212> TYPE: PRT
<213> ORGANISM: artificial
<220> FEATURE:
<223> OTHER INFORMATION: homocitrulline containing Fibrinogen alpha
      counterpart
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (17)..(17)
<223> OTHER INFORMATION: homocitrulline

<400> SEQUENCE: 71

Pro Gly Ile Ala Glu Phe Pro Ser Arg Gly Xaa Ser Ser Ser Tyr Ser
1               5                   10                  15

Xaa Gln Phe Thr Ser
            20

<210> SEQ ID NO 72
<211> LENGTH: 21
<212> TYPE: PRT
<213> ORGANISM: homo sapiens

<400> SEQUENCE: 72

Pro Ser Arg Gly Lys Ser Ser Ser Tyr Ser Lys Gln Phe Thr Ser Ser
1               5                   10                  15

Thr Ser Tyr Asn Arg
            20

<210> SEQ ID NO 73
<211> LENGTH: 21
<212> TYPE: PRT
<213> ORGANISM: artificial
<220> FEATURE:
<223> OTHER INFORMATION: homocitrulline containing Fibrinogen alpha
      counterpart
<220> FEATURE:
<221> NAME/KEY: MISC_FEATURE
<222> LOCATION: (5)..(5)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline

<400> SEQUENCE: 73

Pro Ser Arg Gly Xaa Ser Ser Ser Tyr Ser Xaa Gln Phe Thr Ser Ser
1               5                   10                  15

Thr Ser Tyr Asn Arg
            20

<210> SEQ ID NO 74
<211> LENGTH: 21
<212> TYPE: PRT
<213> ORGANISM: homo sapiens

<400> SEQUENCE: 74

Tyr Asn Arg Gly Asp Ser Thr Phe Glu Ser Lys Ser Tyr Lys Met Ala
```

```
1               5                  10                 15

Asp Glu Ala Gly Ser
            20

<210> SEQ ID NO 75
<211> LENGTH: 21
<212> TYPE: PRT
<213> ORGANISM: artificial
<220> FEATURE:
<223> OTHER INFORMATION: homocitrulline containing Fibrinogen alpha
      counterpart
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (14)..(14)
<223> OTHER INFORMATION: homocitrulline

<400> SEQUENCE: 75

Tyr Asn Arg Gly Asp Ser Thr Phe Glu Ser Xaa Ser Tyr Xaa Met Ala
1               5                  10                 15

Asp Glu Ala Gly Ser
            20

<210> SEQ ID NO 76
<211> LENGTH: 21
<212> TYPE: PRT
<213> ORGANISM: homo sapiens

<400> SEQUENCE: 76

Gly Asp Ser Thr Phe Glu Ser Lys Ser Tyr Lys Met Ala Asp Glu Ala
1               5                  10                 15

Gly Ser Glu Ala Asp
            20

<210> SEQ ID NO 77
<211> LENGTH: 21
<212> TYPE: PRT
<213> ORGANISM: artificial
<220> FEATURE:
<223> OTHER INFORMATION: homocitrulline containing Fibrinogen alpha
      counterpart
<220> FEATURE:
<221> NAME/KEY: MISC_FEATURE
<222> LOCATION: (8)..(8)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline

<400> SEQUENCE: 77

Gly Asp Ser Thr Phe Glu Ser Xaa Ser Tyr Xaa Met Ala Asp Glu Ala
1               5                  10                 15

Gly Ser Glu Ala Asp
            20

<210> SEQ ID NO 78
<211> LENGTH: 21
<212> TYPE: PRT
<213> ORGANISM: homo sapiens

<400> SEQUENCE: 78

Glu Ala Asp His Glu Gly Thr His Ser Thr Lys Arg Gly His Ala Lys
1               5                  10                 15
```

Ser Arg Pro Val Arg
        20

<210> SEQ ID NO 79
<211> LENGTH: 21
<212> TYPE: PRT
<213> ORGANISM: artificial
<220> FEATURE:
<223> OTHER INFORMATION: homocitrulline containing Fibrinogen alpha
      counterpart
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (16)..(16)
<223> OTHER INFORMATION: homocitrulline

<400> SEQUENCE: 79

Glu Ala Asp His Glu Gly Thr His Ser Thr Xaa Arg Gly His Ala Xaa
1               5                   10                  15

Ser Arg Pro Val Arg
        20

<210> SEQ ID NO 80
<211> LENGTH: 21
<212> TYPE: PRT
<213> ORGANISM: homo sapiens

<400> SEQUENCE: 80

Gly Thr His Ser Thr Lys Arg Gly His Ala Lys Ser Arg Pro Val Arg
1               5                   10                  15

Asp Cys Asp Asp Val
        20

<210> SEQ ID NO 81
<211> LENGTH: 21
<212> TYPE: PRT
<213> ORGANISM: artificial
<220> FEATURE:
<223> OTHER INFORMATION: homocitrulline containing Fibrinogen alpha
      counterpart
<220> FEATURE:
<221> NAME/KEY: MISC_FEATURE
<222> LOCATION: (6)..(6)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline

<400> SEQUENCE: 81

Gly Thr His Ser Thr Xaa Arg Gly His Ala Xaa Ser Arg Pro Val Arg
1               5                   10                  15

Asp Cys Asp Asp Val
        20

<210> SEQ ID NO 82
<211> LENGTH: 21
<212> TYPE: PRT
<213> ORGANISM: homo sapiens

<400> SEQUENCE: 82

Ser Gly Thr Gln Ser Gly Ile Phe Asn Ile Lys Leu Pro Gly Ser Ser
1               5                   10                  15

Lys Ile Phe Ser Val
            20

<210> SEQ ID NO 83
<211> LENGTH: 21
<212> TYPE: PRT
<213> ORGANISM: artificial
<220> FEATURE:
<223> OTHER INFORMATION: homocitrulline containing Fibrinogen alpha
      counterpart
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (17)..(17)
<223> OTHER INFORMATION: homocitrulline

<400> SEQUENCE: 83

Ser Gly Thr Gln Ser Gly Ile Phe Asn Ile Xaa Leu Pro Gly Ser Ser
1               5                   10                  15

Xaa Ile Phe Ser Val
            20

<210> SEQ ID NO 84
<211> LENGTH: 21
<212> TYPE: PRT
<213> ORGANISM: homo sapiens

<400> SEQUENCE: 84

Ile Phe Asn Ile Lys Leu Pro Gly Ser Ser Lys Ile Phe Ser Val Tyr
1               5                   10                  15

Cys Asp Gln Glu Thr
            20

<210> SEQ ID NO 85
<211> LENGTH: 21
<212> TYPE: PRT
<213> ORGANISM: artificial
<220> FEATURE:
<223> OTHER INFORMATION: homocitrulline containing Fibrinogen alpha
      counterpart
<220> FEATURE:
<221> NAME/KEY: MISC_FEATURE
<222> LOCATION: (5)..(5)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline

<400> SEQUENCE: 85

Ile Phe Asn Ile Xaa Leu Pro Gly Ser Ser Xaa Ile Phe Ser Val Tyr
1               5                   10                  15

Cys Asp Gln Glu Thr
            20

<210> SEQ ID NO 86
<211> LENGTH: 21
<212> TYPE: PRT
<213> ORGANISM: homo sapiens

<400> SEQUENCE: 86

Leu Asn Phe Asn Arg Thr Trp Gln Asp Tyr Lys Arg Gly Phe Gly Ser
1               5                   10                  15

Leu Asn Asp Glu Gly

```
<210> SEQ ID NO 87
<211> LENGTH: 21
<212> TYPE: PRT
<213> ORGANISM: artificial
<220> FEATURE:
<223> OTHER INFORMATION: homocitrulline containing Fibrinogen alpha
      counterpart
<220> FEATURE:
<221> NAME/KEY: MISC_FEATURE
<222> LOCATION: (11)..(11)
<223> OTHER INFORMATION: homocitrulline

<400> SEQUENCE: 87

Leu Asn Phe Asn Arg Thr Trp Gln Asp Tyr Xaa Arg Gly Phe Gly Ser
1               5                   10                  15

Leu Asn Asp Glu Gly
            20

<210> SEQ ID NO 88
<211> LENGTH: 16
<212> TYPE: PRT
<213> ORGANISM: homo sapiens

<400> SEQUENCE: 88

Val Arg Gly Ile His Thr Ser Pro Leu Gly Lys Pro Ser Leu Ser Pro
1               5                   10                  15

<210> SEQ ID NO 89
<211> LENGTH: 16
<212> TYPE: PRT
<213> ORGANISM: artificial
<220> FEATURE:
<223> OTHER INFORMATION: homocitrulline containing Fibrinogen alpha
      counterpart
<220> FEATURE:
<221> NAME/KEY: MISC_FEATURE
<222> LOCATION: (11)..(11)
<223> OTHER INFORMATION: homocitrulline

<400> SEQUENCE: 89

Val Arg Gly Ile His Thr Ser Pro Leu Gly Xaa Pro Ser Leu Ser Pro
1               5                   10                  15

<210> SEQ ID NO 90
<211> LENGTH: 12
<212> TYPE: PRT
<213> ORGANISM: homo sapiens

<400> SEQUENCE: 90

Met Lys Arg Met Val Ser Trp Ser Phe His Lys Leu
1               5                   10

<210> SEQ ID NO 91
<211> LENGTH: 12
<212> TYPE: PRT
<213> ORGANISM: artificial
<220> FEATURE:
<223> OTHER INFORMATION: homocitrulline containing Fibrinogen beta
      counterpart
<220> FEATURE:
<221> NAME/KEY: MISC_FEATURE
<222> LOCATION: (2)..(2)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline
```

<400> SEQUENCE: 91

Met Xaa Arg Met Val Ser Trp Ser Phe His Xaa Leu
1               5                   10

<210> SEQ ID NO 92
<211> LENGTH: 21
<212> TYPE: PRT
<213> ORGANISM: homo sapiens

<400> SEQUENCE: 92

Met Lys Arg Met Val Ser Trp Ser Phe His Lys Leu Lys Thr Met Lys
1               5                   10                  15

His Leu Leu Leu Leu
            20

<210> SEQ ID NO 93
<211> LENGTH: 21
<212> TYPE: PRT
<213> ORGANISM: artificial
<220> FEATURE:
<223> OTHER INFORMATION: homocitrulline containing Fibrinogen beta
      counterpart
<220> FEATURE:
<221> NAME/KEY: MISC_FEATURE
<222> LOCATION: (2)..(2)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (13)..(13)
<223> OTHER INFORMATION: homocitrulline
<220> FEATURE:
<221> NAME/KEY: MISC_FEATURE
<222> LOCATION: (16)..(16)
<223> OTHER INFORMATION: homocitrulline

<400> SEQUENCE: 93

Met Xaa Arg Met Val Ser Trp Ser Phe His Xaa Leu Xaa Thr Met Xaa
1               5                   10                  15

His Leu Leu Leu Leu
            20

<210> SEQ ID NO 94
<211> LENGTH: 21
<212> TYPE: PRT
<213> ORGANISM: homo sapiens

<400> SEQUENCE: 94

Arg Met Val Ser Trp Ser Phe His Lys Leu Lys Thr Met Lys His Leu
1               5                   10                  15

Leu Leu Leu Leu
            20

<210> SEQ ID NO 95
<211> LENGTH: 21
<212> TYPE: PRT
<213> ORGANISM: artificial
<220> FEATURE:
<223> OTHER INFORMATION: homocitrulline containing Fibrinogen beta
      counterpart
<220> FEATURE:
<221> NAME/KEY: MISC_FEATURE
<222> LOCATION: (9)..(9)
<223> OTHER INFORMATION: homocitrulline -continued

```
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (14)..(14)
<223> OTHER INFORMATION: homocitrulline

<400> SEQUENCE: 95

Arg Met Val Ser Trp Ser Phe His Xaa Leu Xaa Thr Met Xaa His Leu
1               5                   10                  15

Leu Leu Leu Leu Leu
            20

<210> SEQ ID NO 96
<211> LENGTH: 21
<212> TYPE: PRT
<213> ORGANISM: homo sapiens

<400> SEQUENCE: 96

Ser Trp Ser Phe His Lys Leu Lys Thr Met Lys His Leu Leu Leu Leu
1               5                   10                  15

Leu Leu Cys Val Phe
            20

<210> SEQ ID NO 97
<211> LENGTH: 21
<212> TYPE: PRT
<213> ORGANISM: artificial
<220> FEATURE:
<223> OTHER INFORMATION: homocitrulline containing Fibrinogen beta
      counterpart
<220> FEATURE:
<221> NAME/KEY: MISC_FEATURE
<222> LOCATION: (6)..(6)
<223> OTHER INFORMATION: homocitrulline
<220> FEATURE:
<221> NAME/KEY: MISC_FEATURE
<222> LOCATION: (8)..(8)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline

<400> SEQUENCE: 97

Ser Trp Ser Phe His Xaa Leu Xaa Thr Met Xaa His Leu Leu Leu Leu
1               5                   10                  15

Leu Leu Cys Val Phe
            20

<210> SEQ ID NO 98
<211> LENGTH: 21
<212> TYPE: PRT
<213> ORGANISM: homo sapiens

<400> SEQUENCE: 98

Leu Leu Leu Leu Leu Cys Val Phe Leu Val Lys Ser Gln Gly Val Asn
1               5                   10                  15

Asp Asn Glu Glu Gly
            20

<210> SEQ ID NO 99
<211> LENGTH: 21
<212> TYPE: PRT
<213> ORGANISM: artificial
```

```
<220> FEATURE:
<223> OTHER INFORMATION: homocitrulline containing Fibrinogen beta
      counterpart
<220> FEATURE:
<221> NAME/KEY: MISC_FEATURE
<222> LOCATION: (11)..(11)
<223> OTHER INFORMATION: homocitrulline

<400> SEQUENCE: 99

Leu Leu Leu Leu Leu Cys Val Phe Leu Val Xaa Ser Gln Gly Val Asn
1               5                   10                  15

Asp Asn Glu Glu Gly
            20

<210> SEQ ID NO 100
<211> LENGTH: 21
<212> TYPE: PRT
<213> ORGANISM: homo sapiens

<400> SEQUENCE: 100

Phe Ser Ala Arg Gly His Arg Pro Leu Asp Lys Lys Arg Glu Glu Ala
1               5                   10                  15

Pro Ser Leu Arg Pro
            20

<210> SEQ ID NO 101
<211> LENGTH: 21
<212> TYPE: PRT
<213> ORGANISM: artificial
<220> FEATURE:
<223> OTHER INFORMATION: homocitrulline containing Fibrinogen beta
      counterpart
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (12)..(12)
<223> OTHER INFORMATION: homocitrulline

<400> SEQUENCE: 101

Phe Ser Ala Arg Gly His Arg Pro Leu Asp Xaa Xaa Arg Glu Glu Ala
1               5                   10                  15

Pro Ser Leu Arg Pro
            20

<210> SEQ ID NO 102
<211> LENGTH: 21
<212> TYPE: PRT
<213> ORGANISM: homo sapiens

<400> SEQUENCE: 102

Ser Ala Arg Gly His Arg Pro Leu Asp Lys Lys Arg Glu Glu Ala Pro
1               5                   10                  15

Ser Leu Arg Pro Ala
            20

<210> SEQ ID NO 103
<211> LENGTH: 21
<212> TYPE: PRT
<213> ORGANISM: artificial
<220> FEATURE:
<223> OTHER INFORMATION: homocitrulline containing Fibrinogen beta
      counterpart
<220> FEATURE:
<221> NAME/KEY: MISC_FEATURE
```

```
<222> LOCATION: (10)..(10)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline

<400> SEQUENCE: 103

Ser Ala Arg Gly His Arg Pro Leu Asp Xaa Xaa Arg Glu Glu Ala Pro
1               5                   10                  15

Ser Leu Arg Pro Ala
            20

<210> SEQ ID NO 104
<211> LENGTH: 21
<212> TYPE: PRT
<213> ORGANISM: homo sapiens

<400> SEQUENCE: 104

Ser Gly Gly Gly Tyr Arg Ala Arg Pro Ala Lys Ala Ala Ala Thr Gln
1               5                   10                  15

Lys Lys Val Glu Arg
            20

<210> SEQ ID NO 105
<211> LENGTH: 21
<212> TYPE: PRT
<213> ORGANISM: artificial
<220> FEATURE:
<223> OTHER INFORMATION: homocitrulline containing Fibrinogen beta
      counterpart
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (17)..(17)
<223> OTHER INFORMATION: homocitrulline
<220> FEATURE:
<221> NAME/KEY: MISC_FEATURE
<222> LOCATION: (18)..(18)
<223> OTHER INFORMATION: homocitrulline

<400> SEQUENCE: 105

Ser Gly Gly Gly Tyr Arg Ala Arg Pro Ala Xaa Ala Ala Ala Thr Gln
1               5                   10                  15

Xaa Xaa Val Glu Arg
            20

<210> SEQ ID NO 106
<211> LENGTH: 21
<212> TYPE: PRT
<213> ORGANISM: homo sapiens

<400> SEQUENCE: 106

Ala Arg Pro Ala Lys Ala Ala Ala Thr Gln Lys Lys Val Glu Arg Lys
1               5                   10                  15

Ala Pro Asp Ala Gly
            20

<210> SEQ ID NO 107
<211> LENGTH: 21
<212> TYPE: PRT
<213> ORGANISM: artificial
<220> FEATURE:
<223> OTHER INFORMATION: homocitrulline containing Fibrinogen beta
```

```
            counterpart
<220> FEATURE:
<221> NAME/KEY: MISC_FEATURE
<222> LOCATION: (5)..(5)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (12)..(12)
<223> OTHER INFORMATION: homocitrulline
<220> FEATURE:
<221> NAME/KEY: MISC_FEATURE
<222> LOCATION: (16)..(16)
<223> OTHER INFORMATION: homocitrulline

<400> SEQUENCE: 107

Ala Arg Pro Ala Xaa Ala Ala Ala Thr Gln Xaa Xaa Val Glu Arg Xaa
1               5                   10                  15

Ala Pro Asp Ala Gly
            20

<210> SEQ ID NO 108
<211> LENGTH: 21
<212> TYPE: PRT
<213> ORGANISM: homo sapiens

<400> SEQUENCE: 108

Arg Pro Ala Lys Ala Ala Ala Thr Gln Lys Lys Val Glu Arg Lys Ala
1               5                   10                  15

Pro Asp Ala Gly Gly
            20

<210> SEQ ID NO 109
<211> LENGTH: 21
<212> TYPE: PRT
<213> ORGANISM: artificial
<220> FEATURE:
<223> OTHER INFORMATION: homocitrulline containing Fibrinogen beta
      counterpart
<220> FEATURE:
<221> NAME/KEY: MISC_FEATURE
<222> LOCATION: (4)..(4)
<223> OTHER INFORMATION: homocitrulline
<220> FEATURE:
<221> NAME/KEY: MISC_FEATURE
<222> LOCATION: (10)..(10)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (15)..(15)
<223> OTHER INFORMATION: homocitrulline

<400> SEQUENCE: 109

Arg Pro Ala Xaa Ala Ala Ala Thr Gln Xaa Xaa Val Glu Arg Xaa Ala
1               5                   10                  15

Pro Asp Ala Gly Gly
            20

<210> SEQ ID NO 110
<211> LENGTH: 21
<212> TYPE: PRT
<213> ORGANISM: homo sapiens
```

```
<400> SEQUENCE: 110

Ala Ala Ala Thr Gln Lys Lys Val Glu Arg Lys Ala Pro Asp Ala Gly
1               5                   10                  15

Gly Cys Leu His Ala
            20

<210> SEQ ID NO 111
<211> LENGTH: 21
<212> TYPE: PRT
<213> ORGANISM: artificial
<220> FEATURE:
<223> OTHER INFORMATION: homocitrulline containing Fibrinogen beta
      counterpart
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 111

Ala Ala Ala Thr Gln Xaa Xaa Val Glu Arg Xaa Ala Pro Asp Ala Gly
1               5                   10                  15

Gly Cys Leu His Ala
            20

<210> SEQ ID NO 112
<211> LENGTH: 21
<212> TYPE: PRT
<213> ORGANISM: homo sapiens

<400> SEQUENCE: 112

Ser Ser Ser Phe Gln Tyr Met Tyr Leu Leu Lys Asp Leu Trp Gln Lys
1               5                   10                  15

Arg Gln Lys Gln Val
            20

<210> SEQ ID NO 113
<211> LENGTH: 21
<212> TYPE: PRT
<213> ORGANISM: artificial
<220> FEATURE:
<223> OTHER INFORMATION: homocitrulline containing Fibrinogen beta
      counterpart
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (16)..(16)
<223> OTHER INFORMATION: homocitrulline
<220> FEATURE:
<221> NAME/KEY: MISC_FEATURE
<222> LOCATION: (19)..(19)
<223> OTHER INFORMATION: homocitrulline

<400> SEQUENCE: 113

Ser Ser Ser Phe Gln Tyr Met Tyr Leu Leu Xaa Asp Leu Trp Gln Xaa
1               5                   10                  15

Arg Gln Xaa Gln Val
            20

<210> SEQ ID NO 114
<211> LENGTH: 21
```

-continued

```
<212> TYPE: PRT
<213> ORGANISM: homo sapiens

<400> SEQUENCE: 114

Tyr Met Tyr Leu Leu Lys Asp Leu Trp Gln Lys Arg Gln Lys Gln Val
1               5                   10                  15

Lys Asp Asn Glu Asn
            20

<210> SEQ ID NO 115
<211> LENGTH: 21
<212> TYPE: PRT
<213> ORGANISM: artificial
<220> FEATURE:
<223> OTHER INFORMATION: homocitrulline containing Fibrinogen beta
      counterpart
<220> FEATURE:
<221> NAME/KEY: MISC_FEATURE
<222> LOCATION: (6)..(6)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (14)..(14)
<223> OTHER INFORMATION: homocitrulline
<220> FEATURE:
<221> NAME/KEY: MISC_FEATURE
<222> LOCATION: (17)..(17)
<223> OTHER INFORMATION: homocitrulline

<400> SEQUENCE: 115

Tyr Met Tyr Leu Leu Xaa Asp Leu Trp Gln Xaa Arg Gln Xaa Gln Val
1               5                   10                  15

Xaa Asp Asn Glu Asn
            20

<210> SEQ ID NO 116
<211> LENGTH: 21
<212> TYPE: PRT
<213> ORGANISM: homo sapiens

<400> SEQUENCE: 116

Leu Leu Lys Asp Leu Trp Gln Lys Arg Gln Lys Gln Val Lys Asp Asn
1               5                   10                  15

Glu Asn Val Val Asn
            20

<210> SEQ ID NO 117
<211> LENGTH: 21
<212> TYPE: PRT
<213> ORGANISM: artificial
<220> FEATURE:
<223> OTHER INFORMATION: homocitrulline containing Fibrinogen beta
      counterpart
<220> FEATURE:
<221> NAME/KEY: MISC_FEATURE
<222> LOCATION: (3)..(3)
<223> OTHER INFORMATION: homocitrulline
<220> FEATURE:
<221> NAME/KEY: MISC_FEATURE
<222> LOCATION: (8)..(8)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline
<220> FEATURE:
```

```
<221> NAME/KEY: MISC_FEATURE
<222> LOCATION: (14)..(14)
<223> OTHER INFORMATION: homocitrulline

<400> SEQUENCE: 117

Leu Leu Xaa Asp Leu Trp Gln Xaa Arg Gln Xaa Gln Val Xaa Asp Asn
1               5                   10                  15

Glu Asn Val Val Asn
            20

<210> SEQ ID NO 118
<211> LENGTH: 21
<212> TYPE: PRT
<213> ORGANISM: homo sapiens

<400> SEQUENCE: 118

Asp Leu Trp Gln Lys Arg Gln Lys Gln Val Lys Asp Asn Glu Asn Val
1               5                   10                  15

Val Asn Glu Tyr Ser
            20

<210> SEQ ID NO 119
<211> LENGTH: 21
<212> TYPE: PRT
<213> ORGANISM: artificial
<220> FEATURE:
<223> OTHER INFORMATION: homocitrulline containing Fibrinogen beta
      counterpart
<220> FEATURE:
<221> NAME/KEY: MISC_FEATURE
<222> LOCATION: (5)..(5)
<223> OTHER INFORMATION: homocitrulline
<220> FEATURE:
<221> NAME/KEY: MISC_FEATURE
<222> LOCATION: (8)..(8)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline

<400> SEQUENCE: 119

Asp Leu Trp Gln Xaa Arg Gln Xaa Gln Val Xaa Asp Asn Glu Asn Val
1               5                   10                  15

Val Asn Glu Tyr Ser
            20

<210> SEQ ID NO 120
<211> LENGTH: 21
<212> TYPE: PRT
<213> ORGANISM: homo sapiens

<400> SEQUENCE: 120

Pro Val Val Ser Cys Glu Glu Ile Ile Arg Lys Gly Gly Glu Thr Ser
1               5                   10                  15

Glu Met Tyr Leu Ile
            20

<210> SEQ ID NO 121
<211> LENGTH: 21
<212> TYPE: PRT
<213> ORGANISM: artificial
<220> FEATURE:
<223> OTHER INFORMATION: homocitrulline containing Fibrinogen beta
      counterpart
<220> FEATURE:
<221> NAME/KEY: MISC_FEATURE
```

<222> LOCATION: (11)..(11)
<223> OTHER INFORMATION: homocitrulline

<400> SEQUENCE: 121

Pro Val Val Ser Cys Glu Glu Ile Ile Arg Xaa Gly Gly Glu Thr Ser
1               5                   10                  15

Glu Met Tyr Leu Ile
            20

<210> SEQ ID NO 122
<211> LENGTH: 21
<212> TYPE: PRT
<213> ORGANISM: homo sapiens

<400> SEQUENCE: 122

Met Tyr Leu Ile Gln Pro Asp Ser Ser Val Lys Pro Tyr Arg Val Tyr
1               5                   10                  15

Cys Asp Met Asn Thr
            20

<210> SEQ ID NO 123
<211> LENGTH: 21
<212> TYPE: PRT
<213> ORGANISM: artificial
<220> FEATURE:
<223> OTHER INFORMATION: homocitrulline containing Fibrinogen beta
      counterpart
<220> FEATURE:
<221> NAME/KEY: MISC_FEATURE
<222> LOCATION: (11)..(11)
<223> OTHER INFORMATION: homocitrulline

<400> SEQUENCE: 123

Met Tyr Leu Ile Gln Pro Asp Ser Ser Val Xaa Pro Tyr Arg Val Tyr
1               5                   10                  15

Cys Asp Met Asn Thr
            20

<210> SEQ ID NO 124
<211> LENGTH: 21
<212> TYPE: PRT
<213> ORGANISM: homo sapiens

<400> SEQUENCE: 124

Val Asp Phe Gly Arg Lys Trp Asp Pro Tyr Lys Gln Gly Phe Gly Asn
1               5                   10                  15

Val Ala Thr Asn Thr
            20

<210> SEQ ID NO 125
<211> LENGTH: 21
<212> TYPE: PRT
<213> ORGANISM: artificial
<220> FEATURE:
<223> OTHER INFORMATION: homocitrulline containing Fibrinogen beta
      counterpart
<220> FEATURE:
<221> NAME/KEY: MISC_FEATURE
<222> LOCATION: (6)..(6)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline

<400> SEQUENCE: 125

```
Val Asp Phe Gly Arg Xaa Trp Asp Pro Tyr Xaa Gln Gly Phe Gly Asn
1               5                   10                  15

Val Ala Thr Asn Thr
            20

<210> SEQ ID NO 126
<211> LENGTH: 21
<212> TYPE: PRT
<213> ORGANISM: homo sapiens

<400> SEQUENCE: 126

Phe Gly Asn Val Ala Thr Asn Thr Asp Gly Lys Asn Tyr Cys Gly Leu
1               5                   10                  15

Pro Gly Glu Tyr Trp
            20

<210> SEQ ID NO 127
<211> LENGTH: 21
<212> TYPE: PRT
<213> ORGANISM: artificial
<220> FEATURE:
<223> OTHER INFORMATION: homocitrulline containing Fibrinogen beta
      counterpart
<220> FEATURE:
<221> NAME/KEY: MISC_FEATURE
<222> LOCATION: (11)..(11)
<223> OTHER INFORMATION: homocitrulline

<400> SEQUENCE: 127

Phe Gly Asn Val Ala Thr Asn Thr Asp Gly Xaa Asn Tyr Cys Gly Leu
1               5                   10                  15

Pro Gly Glu Tyr Trp
            20

<210> SEQ ID NO 128
<211> LENGTH: 21
<212> TYPE: PRT
<213> ORGANISM: homo sapiens

<400> SEQUENCE: 128

Leu Pro Gly Glu Tyr Trp Leu Gly Asn Asp Lys Ile Ser Gln Leu Thr
1               5                   10                  15

Arg Met Gly Pro Thr
            20

<210> SEQ ID NO 129
<211> LENGTH: 21
<212> TYPE: PRT
<213> ORGANISM: artificial
<220> FEATURE:
<223> OTHER INFORMATION: homocitrulline containing Fibrinogen beta
      counterpart
<220> FEATURE:
<221> NAME/KEY: MISC_FEATURE
<222> LOCATION: (11)..(11)
<223> OTHER INFORMATION: homocitrulline

<400> SEQUENCE: 129

Leu Pro Gly Glu Tyr Trp Leu Gly Asn Asp Xaa Ile Ser Gln Leu Thr
1               5                   10                  15

Arg Met Gly Pro Thr
            20

<210> SEQ ID NO 130
<211> LENGTH: 21
```

<212> TYPE: PRT
<213> ORGANISM: homo sapiens

<400> SEQUENCE: 130

Thr Glu Leu Leu Ile Glu Met Glu Asp Trp Lys Gly Asp Lys Val Lys
1               5                   10                  15

Ala His Tyr Gly Gly
            20

<210> SEQ ID NO 131
<211> LENGTH: 21
<212> TYPE: PRT
<213> ORGANISM: artificial
<220> FEATURE:
<223> OTHER INFORMATION: homocitrulline containing Fibrinogen beta
      counterpart
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (14)..(14)
<223> OTHER INFORMATION: homocitrulline
<220> FEATURE:
<221> NAME/KEY: MISC_FEATURE
<222> LOCATION: (16)..(16)
<223> OTHER INFORMATION: homocitrulline

<400> SEQUENCE: 131

Thr Glu Leu Leu Ile Glu Met Glu Asp Trp Xaa Gly Asp Xaa Val Xaa
1               5                   10                  15

Ala His Tyr Gly Gly
            20

<210> SEQ ID NO 132
<211> LENGTH: 21
<212> TYPE: PRT
<213> ORGANISM: homo sapiens

<400> SEQUENCE: 132

Leu Ile Glu Met Glu Asp Trp Lys Gly Asp Lys Val Lys Ala His Tyr
1               5                   10                  15

Gly Gly Phe Thr Val
            20

<210> SEQ ID NO 133
<211> LENGTH: 21
<212> TYPE: PRT
<213> ORGANISM: artificial
<220> FEATURE:
<223> OTHER INFORMATION: homocitrulline containing Fibrinogen beta
      counterpart
<220> FEATURE:
<221> NAME/KEY: MISC_FEATURE
<222> LOCATION: (8)..(8)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (13)..(13)
<223> OTHER INFORMATION: homocitrulline

<400> SEQUENCE: 133

Leu Ile Glu Met Glu Asp Trp Xaa Gly Asp Xaa Val Xaa Ala His Tyr
1               5                   10                  15

```
Gly Gly Phe Thr Val
         20

<210> SEQ ID NO 134
<211> LENGTH: 21
<212> TYPE: PRT
<213> ORGANISM: homo sapiens

<400> SEQUENCE: 134

Glu Met Glu Asp Trp Lys Gly Asp Lys Val Lys Ala His Tyr Gly Gly
1               5                   10                  15

Phe Thr Val Gln Asn
         20

<210> SEQ ID NO 135
<211> LENGTH: 21
<212> TYPE: PRT
<213> ORGANISM: artificial
<220> FEATURE:
<223> OTHER INFORMATION: homocitrulline containing Fibrinogen beta
      counterpart
<220> FEATURE:
<221> NAME/KEY: MISC_FEATURE
<222> LOCATION: (6)..(6)
<223> OTHER INFORMATION: homocitrulline
<220> FEATURE:
<221> NAME/KEY: MISC_FEATURE
<222> LOCATION: (9)..(9)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline

<400> SEQUENCE: 135

Glu Met Glu Asp Trp Xaa Gly Asp Xaa Val Xaa Ala His Tyr Gly Gly
1               5                   10                  15

Phe Thr Val Gln Asn
         20

<210> SEQ ID NO 136
<211> LENGTH: 21
<212> TYPE: PRT
<213> ORGANISM: homo sapiens

<400> SEQUENCE: 136

Gly Gly Phe Thr Val Gln Asn Glu Ala Asn Lys Tyr Gln Ile Ser Val
1               5                   10                  15

Asn Lys Tyr Arg Gly
         20

<210> SEQ ID NO 137
<211> LENGTH: 21
<212> TYPE: PRT
<213> ORGANISM: artificial
<220> FEATURE:
<223> OTHER INFORMATION: homocitrulline containing Fibrinogen beta
      counterpart
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (18)..(18)
<223> OTHER INFORMATION: homocitrulline

<400> SEQUENCE: 137
```

Gly Gly Phe Thr Val Gln Asn Glu Ala Asn Xaa Tyr Gln Ile Ser Val
1               5                   10                  15

Asn Xaa Tyr Arg Gly
            20

<210> SEQ ID NO 138
<211> LENGTH: 21
<212> TYPE: PRT
<213> ORGANISM: homo sapiens

<400> SEQUENCE: 138

Glu Ala Asn Lys Tyr Gln Ile Ser Val Asn Lys Tyr Arg Gly Thr Ala
1               5                   10                  15

Gly Asn Ala Leu Met
            20

<210> SEQ ID NO 139
<211> LENGTH: 21
<212> TYPE: PRT
<213> ORGANISM: artificial
<220> FEATURE:
<223> OTHER INFORMATION: homocitrulline containing Fibrinogen beta
      counterpart
<220> FEATURE:
<221> NAME/KEY: MISC_FEATURE
<222> LOCATION: (4)..(4)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline

<400> SEQUENCE: 139

Glu Ala Asn Xaa Tyr Gln Ile Ser Val Asn Xaa Tyr Arg Gly Thr Ala
1               5                   10                  15

Gly Asn Ala Leu Met
            20

<210> SEQ ID NO 140
<211> LENGTH: 21
<212> TYPE: PRT
<213> ORGANISM: homo sapiens

<400> SEQUENCE: 140

Asn Asp Gly Trp Leu Thr Ser Asp Pro Arg Lys Gln Cys Ser Lys Glu
1               5                   10                  15

Asp Gly Gly Gly Trp
            20

<210> SEQ ID NO 141
<211> LENGTH: 21
<212> TYPE: PRT
<213> ORGANISM: artificial
<220> FEATURE:
<223> OTHER INFORMATION: homocitrulline containing Fibrinogen beta
      counterpart
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (15)..(15)
<223> OTHER INFORMATION: homocitrulline

<400> SEQUENCE: 141

```
Asn Asp Gly Trp Leu Thr Ser Asp Pro Arg Xaa Gln Cys Ser Xaa Glu
1               5                   10                  15

Asp Gly Gly Gly Trp
            20

<210> SEQ ID NO 142
<211> LENGTH: 21
<212> TYPE: PRT
<213> ORGANISM: homo sapiens

<400> SEQUENCE: 142

Leu Thr Ser Asp Pro Arg Lys Gln Cys Ser Lys Glu Asp Gly Gly Gly
1               5                   10                  15

Trp Trp Tyr Asn Arg
            20

<210> SEQ ID NO 143
<211> LENGTH: 21
<212> TYPE: PRT
<213> ORGANISM: artificial
<220> FEATURE:
<223> OTHER INFORMATION: homocitrulline containing Fibrinogen beta
      counterpart
<220> FEATURE:
<221> NAME/KEY: MISC_FEATURE
<222> LOCATION: (7)..(7)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline

<400> SEQUENCE: 143

Leu Thr Ser Asp Pro Arg Xaa Gln Cys Ser Xaa Glu Asp Gly Gly Gly
1               5                   10                  15

Trp Trp Tyr Asn Arg
            20

<210> SEQ ID NO 144
<211> LENGTH: 21
<212> TYPE: PRT
<213> ORGANISM: homo sapiens

<400> SEQUENCE: 144

Trp Gly Gly Gln Tyr Thr Trp Asp Met Ala Lys His Gly Thr Asp Asp
1               5                   10                  15

Gly Val Val Trp Met
            20

<210> SEQ ID NO 145
<211> LENGTH: 21
<212> TYPE: PRT
<213> ORGANISM: artificial
<220> FEATURE:
<223> OTHER INFORMATION: homocitrulline containing Fibrinogen beta
      counterpart
<220> FEATURE:
<221> NAME/KEY: MISC_FEATURE
<222> LOCATION: (11)..(11)
<223> OTHER INFORMATION: homocitrulline

<400> SEQUENCE: 145

Trp Gly Gly Gln Tyr Thr Trp Asp Met Ala Xaa His Gly Thr Asp Asp
1               5                   10                  15

Gly Val Val Trp Met
            20
```

<210> SEQ ID NO 146
<211> LENGTH: 21
<212> TYPE: PRT
<213> ORGANISM: homo sapiens

<400> SEQUENCE: 146

Thr Asp Asp Gly Val Val Trp Met Asn Trp Lys Gly Ser Trp Tyr Ser
1               5                   10                  15

Met Arg Lys Met Ser
            20

<210> SEQ ID NO 147
<211> LENGTH: 21
<212> TYPE: PRT
<213> ORGANISM: artificial
<220> FEATURE:
<223> OTHER INFORMATION: homocitrulline containing Fibrinogen beta
      counterpart
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (19)..(19)
<223> OTHER INFORMATION: homocitrulline

<400> SEQUENCE: 147

Thr Asp Asp Gly Val Val Trp Met Asn Trp Xaa Gly Ser Trp Tyr Ser
1               5                   10                  15

Met Arg Xaa Met Ser
            20

<210> SEQ ID NO 148
<211> LENGTH: 21
<212> TYPE: PRT
<213> ORGANISM: homo sapiens

<400> SEQUENCE: 148

Asn Trp Lys Gly Ser Trp Tyr Ser Met Arg Lys Met Ser Met Lys Ile
1               5                   10                  15

Arg Pro Phe Phe Gln
            20

<210> SEQ ID NO 149
<211> LENGTH: 21
<212> TYPE: PRT
<213> ORGANISM: artificial
<220> FEATURE:
<223> OTHER INFORMATION: homocitrulline containing Fibrinogen beta
      counterpart
<220> FEATURE:
<221> NAME/KEY: MISC_FEATURE
<222> LOCATION: (3)..(3)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (15)..(15)
<223> OTHER INFORMATION: homocitrulline

<400> SEQUENCE: 149

Asn Trp Xaa Gly Ser Trp Tyr Ser Met Arg Xaa Met Ser Met Xaa Ile
1               5                   10                  15

Arg Pro Phe Phe Gln
            20

<210> SEQ ID NO 150
<211> LENGTH: 19
<212> TYPE: PRT
<213> ORGANISM: homo sapiens

<400> SEQUENCE: 150

Ser Trp Tyr Ser Met Arg Lys Met Ser Met Lys Ile Arg Pro Phe Phe
1               5                   10                  15

Pro Gln Gln

<210> SEQ ID NO 151
<211> LENGTH: 19
<212> TYPE: PRT
<213> ORGANISM: artificial
<220> FEATURE:
<223> OTHER INFORMATION: homocitrulline containing Fibrinogen beta
      counterpart
<220> FEATURE:
<221> NAME/KEY: MISC_FEATURE
<222> LOCATION: (7)..(7)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline

<400> SEQUENCE: 151

Ser Trp Tyr Ser Met Arg Xaa Met Ser Met Xaa Ile Arg Pro Phe Phe
1               5                   10                  15

Pro Gln Gln

<210> SEQ ID NO 152
<211> LENGTH: 21
<212> TYPE: PRT
<213> ORGANISM: homo sapiens

<400> SEQUENCE: 152

Ile Ala Asp Phe Leu Ser Thr Tyr Gln Thr Lys Val Asp Lys Asp Leu
1               5                   10                  15

Gln Ser Leu Glu Asp
            20

<210> SEQ ID NO 153
<211> LENGTH: 21
<212> TYPE: PRT
<213> ORGANISM: artificial
<220> FEATURE:
<223> OTHER INFORMATION: homocitrulline containing Fibrinogen gamma
      counterpart
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (14)..(14)
<223> OTHER INFORMATION: homocitrulline

<400> SEQUENCE: 153

Ile Ala Asp Phe Leu Ser Thr Tyr Gln Thr Xaa Val Asp Xaa Asp Leu
1               5                   10                  15

Gln Ser Leu Glu Asp
            20

```
<210> SEQ ID NO 154
<211> LENGTH: 21
<212> TYPE: PRT
<213> ORGANISM: homo sapiens

<400> SEQUENCE: 154

Phe Leu Ser Thr Tyr Gln Thr Lys Val Asp Lys Asp Leu Gln Ser Leu
1               5                   10                  15

Glu Asp Ile Leu His
            20

<210> SEQ ID NO 155
<211> LENGTH: 21
<212> TYPE: PRT
<213> ORGANISM: artificial
<220> FEATURE:
<223> OTHER INFORMATION: homocitrulline containing Fibrinogen gamma
      counterpart
<220> FEATURE:
<221> NAME/KEY: MISC_FEATURE
<222> LOCATION: (8)..(8)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline

<400> SEQUENCE: 155

Phe Leu Ser Thr Tyr Gln Thr Xaa Val Asp Xaa Asp Leu Gln Ser Leu
1               5                   10                  15

Glu Asp Ile Leu His
            20

<210> SEQ ID NO 156
<211> LENGTH: 21
<212> TYPE: PRT
<213> ORGANISM: homo sapiens

<400> SEQUENCE: 156

Leu Glu Asp Ile Leu His Gln Val Glu Asn Lys Thr Ser Glu Val Lys
1               5                   10                  15

Gln Leu Ile Lys Ala
            20

<210> SEQ ID NO 157
<211> LENGTH: 21
<212> TYPE: PRT
<213> ORGANISM: artificial
<220> FEATURE:
<223> OTHER INFORMATION: homocitrulline containing Fibrinogen gamma
      counterpart
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (16)..(16)
<223> OTHER INFORMATION: homocitrulline
<220> FEATURE:
<221> NAME/KEY: MISC_FEATURE
<222> LOCATION: (20)..(20)
<223> OTHER INFORMATION: homocitrulline

<400> SEQUENCE: 157

Leu Glu Asp Ile Leu His Gln Val Glu Asn Xaa Thr Ser Glu Val Xaa
1               5                   10                  15
```

```
Gln Leu Ile Xaa Ala
            20

<210> SEQ ID NO 158
<211> LENGTH: 21
<212> TYPE: PRT
<213> ORGANISM: homo sapiens

<400> SEQUENCE: 158

His Gln Val Glu Asn Lys Thr Ser Glu Val Lys Gln Leu Ile Lys Ala
1               5                   10                  15

Ile Gln Leu Thr Tyr
            20

<210> SEQ ID NO 159
<211> LENGTH: 21
<212> TYPE: PRT
<213> ORGANISM: artificial
<220> FEATURE:
<223> OTHER INFORMATION: homocitrulline containing Fibrinogen gamma
      counterpart
<220> FEATURE:
<221> NAME/KEY: MISC_FEATURE
<222> LOCATION: (6)..(6)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (15)..(15)
<223> OTHER INFORMATION: homocitrulline

<400> SEQUENCE: 159

His Gln Val Glu Asn Xaa Thr Ser Glu Val Xaa Gln Leu Ile Xaa Ala
1               5                   10                  15

Ile Gln Leu Thr Tyr
            20

<210> SEQ ID NO 160
<211> LENGTH: 21
<212> TYPE: PRT
<213> ORGANISM: homo sapiens

<400> SEQUENCE: 160

Asn Lys Thr Ser Glu Val Lys Gln Leu Ile Lys Ala Ile Gln Leu Thr
1               5                   10                  15

Tyr Asn Pro Asp Glu
            20

<210> SEQ ID NO 161
<211> LENGTH: 21
<212> TYPE: PRT
<213> ORGANISM: artificial
<220> FEATURE:
<223> OTHER INFORMATION: homocitrulline containing Fibrinogen gamma
      counterpart
<220> FEATURE:
<221> NAME/KEY: MISC_FEATURE
<222> LOCATION: (2)..(2)
<223> OTHER INFORMATION: homocitrulline
<220> FEATURE:
<221> NAME/KEY: MISC_FEATURE
<222> LOCATION: (7)..(7)
<223> OTHER INFORMATION: homocitrulline
<220> FEATURE:
<221> NAME/KEY: MISC_FEATURE
```

<222> LOCATION: (11)..(11)
<223> OTHER INFORMATION: homocitrulline

<400> SEQUENCE: 161

Asn Xaa Thr Ser Glu Val Xaa Gln Leu Ile Xaa Ala Ile Gln Leu Thr
1               5                   10                  15

Tyr Asn Pro Asp Glu
            20

<210> SEQ ID NO 162
<211> LENGTH: 21
<212> TYPE: PRT
<213> ORGANISM: homo sapiens

<400> SEQUENCE: 162

Gln Leu Thr Tyr Asn Pro Asp Glu Ser Ser Lys Pro Asn Met Ile Asp
1               5                   10                  15

Ala Ala Thr Leu Lys
            20

<210> SEQ ID NO 163
<211> LENGTH: 21
<212> TYPE: PRT
<213> ORGANISM: artificial
<220> FEATURE:
<223> OTHER INFORMATION: homocitrulline containing Fibrinogen gamma
      counterpart
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (21)..(21)
<223> OTHER INFORMATION: homocitrulline

<400> SEQUENCE: 163

Gln Leu Thr Tyr Asn Pro Asp Glu Ser Ser Xaa Pro Asn Met Ile Asp
1               5                   10                  15

Ala Ala Thr Leu Xaa
            20

<210> SEQ ID NO 164
<211> LENGTH: 21
<212> TYPE: PRT
<213> ORGANISM: homo sapiens

<400> SEQUENCE: 164

Lys Pro Asn Met Ile Asp Ala Ala Thr Leu Lys Ser Arg Lys Met Leu
1               5                   10                  15

Glu Glu Ile Met Lys
            20

<210> SEQ ID NO 165
<211> LENGTH: 21
<212> TYPE: PRT
<213> ORGANISM: artificial
<220> FEATURE:
<223> OTHER INFORMATION: homocitrulline containing Fibrinogen gamma
      counterpart
<220> FEATURE:
<221> NAME/KEY: MISC_FEATURE
<222> LOCATION: (1)..(1)
<223> OTHER INFORMATION: homocitrulline
<220> FEATURE:
<221> NAME/KEY: MISC_FEATURE
<222> LOCATION: (11)..(11)

```
<223> OTHER INFORMATION: homocitrulline
<220> FEATURE:
<221> NAME/KEY: MISC_FEATURE
<222> LOCATION: (14)..(14)
<223> OTHER INFORMATION: homocitrulline
<220> FEATURE:
<221> NAME/KEY: MISC_FEATURE
<222> LOCATION: (21)..(21)
<223> OTHER INFORMATION: homocitrulline

<400> SEQUENCE: 165

Xaa Pro Asn Met Ile Asp Ala Ala Thr Leu Xaa Ser Arg Xaa Met Leu
1               5                   10                  15

Glu Glu Ile Met Xaa
            20

<210> SEQ ID NO 166
<211> LENGTH: 21
<212> TYPE: PRT
<213> ORGANISM: homo sapiens

<400> SEQUENCE: 166

Met Ile Asp Ala Ala Thr Leu Lys Ser Arg Lys Met Leu Glu Glu Ile
1               5                   10                  15

Met Lys Tyr Glu Ala
            20

<210> SEQ ID NO 167
<211> LENGTH: 21
<212> TYPE: PRT
<213> ORGANISM: artificial
<220> FEATURE:
<223> OTHER INFORMATION: homocitrulline containing Fibrinogen gamma
      counterpart
<220> FEATURE:
<221> NAME/KEY: MISC_FEATURE
<222> LOCATION: (8)..(8)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (18)..(18)
<223> OTHER INFORMATION: homocitrulline

<400> SEQUENCE: 167

Met Ile Asp Ala Ala Thr Leu Xaa Ser Arg Xaa Met Leu Glu Glu Ile
1               5                   10                  15

Met Xaa Tyr Glu Ala
            20

<210> SEQ ID NO 168
<211> LENGTH: 21
<212> TYPE: PRT
<213> ORGANISM: homo sapiens

<400> SEQUENCE: 168

Lys Ser Arg Lys Met Leu Glu Glu Ile Met Lys Tyr Glu Ala Ser Ile
1               5                   10                  15

Leu Thr His Asp Ser
            20

<210> SEQ ID NO 169
<211> LENGTH: 21
<212> TYPE: PRT
```

```
<213> ORGANISM: artificial
<220> FEATURE:
<223> OTHER INFORMATION: homocitrulline containing Fibrinogen gamma
      counterpart
<220> FEATURE:
<221> NAME/KEY: MISC_FEATURE
<222> LOCATION: (1)..(1)
<223> OTHER INFORMATION: homocitrulline
<220> FEATURE:
<221> NAME/KEY: MISC_FEATURE
<222> LOCATION: (4)..(4)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline

<400> SEQUENCE: 169

Xaa Ser Arg Xaa Met Leu Glu Glu Ile Met Xaa Tyr Glu Ala Ser Ile
1               5                   10                  15

Leu Thr His Asp Ser
            20

<210> SEQ ID NO 170
<211> LENGTH: 21
<212> TYPE: PRT
<213> ORGANISM: homo sapiens

<400> SEQUENCE: 170

Leu Gln Glu Ile Tyr Asn Ser Asn Asn Gln Lys Ile Val Asn Leu Lys
1               5                   10                  15

Glu Lys Val Ala Gln
            20

<210> SEQ ID NO 171
<211> LENGTH: 21
<212> TYPE: PRT
<213> ORGANISM: artificial
<220> FEATURE:
<223> OTHER INFORMATION: homocitrulline containing Fibrinogen gamma
      counterpart
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (16)..(16)
<223> OTHER INFORMATION: homocitrulline
<220> FEATURE:
<221> NAME/KEY: MISC_FEATURE
<222> LOCATION: (18)..(18)
<223> OTHER INFORMATION: homocitrulline

<400> SEQUENCE: 171

Leu Gln Glu Ile Tyr Asn Ser Asn Asn Gln Xaa Ile Val Asn Leu Xaa
1               5                   10                  15

Glu Xaa Val Ala Gln
            20

<210> SEQ ID NO 172
<211> LENGTH: 21
<212> TYPE: PRT
<213> ORGANISM: homo sapiens

<400> SEQUENCE: 172

Asn Ser Asn Asn Gln Lys Ile Val Asn Leu Lys Glu Lys Val Ala Gln
1               5                   10                  15
```

```
Leu Glu Ala Gln Cys
            20

<210> SEQ ID NO 173
<211> LENGTH: 21
<212> TYPE: PRT
<213> ORGANISM: artificial
<220> FEATURE:
<223> OTHER INFORMATION: homocitrulline containing Fibrinogen gamma
      counterpart
<220> FEATURE:
<221> NAME/KEY: MISC_FEATURE
<222> LOCATION: (6)..(6)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (13)..(13)
<223> OTHER INFORMATION: homocitrulline

<400> SEQUENCE: 173

Asn Ser Asn Asn Gln Xaa Ile Val Asn Leu Xaa Glu Xaa Val Ala Gln
1               5                   10                  15

Leu Glu Ala Gln Cys
            20

<210> SEQ ID NO 174
<211> LENGTH: 21
<212> TYPE: PRT
<213> ORGANISM: homo sapiens

<400> SEQUENCE: 174

Asn Asn Gln Lys Ile Val Asn Leu Lys Glu Lys Val Ala Gln Leu Glu
1               5                   10                  15

Ala Gln Cys Gln Glu
            20

<210> SEQ ID NO 175
<211> LENGTH: 21
<212> TYPE: PRT
<213> ORGANISM: artificial
<220> FEATURE:
<223> OTHER INFORMATION: homocitrulline containing Fibrinogen gamma
      counterpart
<220> FEATURE:
<221> NAME/KEY: MISC_FEATURE
<222> LOCATION: (4)..(4)
<223> OTHER INFORMATION: homocitrulline
<220> FEATURE:
<221> NAME/KEY: MISC_FEATURE
<222> LOCATION: (9)..(9)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline

<400> SEQUENCE: 175

Asn Asn Gln Xaa Ile Val Asn Leu Xaa Glu Xaa Val Ala Gln Leu Glu
1               5                   10                  15

Ala Gln Cys Gln Glu
            20

<210> SEQ ID NO 176
<211> LENGTH: 21
<212> TYPE: PRT
```

<213> ORGANISM: homo sapiens

<400> SEQUENCE: 176

Gln Leu Glu Ala Gln Cys Gln Glu Pro Cys Lys Asp Thr Val Gln Ile
1               5                   10                  15

His Asp Ile Thr Gly
            20

<210> SEQ ID NO 177
<211> LENGTH: 21
<212> TYPE: PRT
<213> ORGANISM: artificial
<220> FEATURE:
<223> OTHER INFORMATION: homocitrulline containing Fibrinogen gamma
      counterpart
<220> FEATURE:
<221> NAME/KEY: MISC_FEATURE
<222> LOCATION: (11)..(11)
<223> OTHER INFORMATION: homocitrulline c

<400> SEQUENCE: 177

Gln Leu Glu Ala Gln Cys Gln Glu Pro Cys Xaa Asp Thr Val Gln Ile
1               5                   10                  15

His Asp Ile Thr Gly
            20

<210> SEQ ID NO 178
<211> LENGTH: 21
<212> TYPE: PRT
<213> ORGANISM: homo sapiens

<400> SEQUENCE: 178

Asp Thr Val Gln Ile His Asp Ile Thr Gly Lys Asp Cys Gln Asp Ile
1               5                   10                  15

Ala Asn Lys Gly Ala
            20

<210> SEQ ID NO 179
<211> LENGTH: 21
<212> TYPE: PRT
<213> ORGANISM: artificial
<220> FEATURE:
<223> OTHER INFORMATION: homocitrulline containing Fibrinogen gamma
      counterpart
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (19)..(19)
<223> OTHER INFORMATION: homocitrulline

<400> SEQUENCE: 179

Asp Thr Val Gln Ile His Asp Ile Thr Gly Xaa Asp Cys Gln Asp Ile
1               5                   10                  15

Ala Asn Xaa Gly Ala
            20

<210> SEQ ID NO 180
<211> LENGTH: 21
<212> TYPE: PRT
<213> ORGANISM: homo sapiens

<400> SEQUENCE: 180

Thr Gly Lys Asp Cys Gln Asp Ile Ala Asn Lys Gly Ala Lys Gln Ser

```
1               5                   10                  15

Gly Leu Tyr Phe Ile
            20

<210> SEQ ID NO 181
<211> LENGTH: 21
<212> TYPE: PRT
<213> ORGANISM: artificial
<220> FEATURE:
<223> OTHER INFORMATION: homocitrulline containing Fibrinogen gamma
      counterpart
<220> FEATURE:
<221> NAME/KEY: MISC_FEATURE
<222> LOCATION: (3)..(3)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (14)..(14)
<223> OTHER INFORMATION: homocitrulline

<400> SEQUENCE: 181

Thr Gly Xaa Asp Cys Gln Asp Ile Ala Asn Xaa Gly Ala Xaa Gln Ser
1               5                   10                  15

Gly Leu Tyr Phe Ile
            20

<210> SEQ ID NO 182
<211> LENGTH: 21
<212> TYPE: PRT
<213> ORGANISM: homo sapiens

<400> SEQUENCE: 182

Asp Cys Gln Asp Ile Ala Asn Lys Gly Ala Lys Gln Ser Gly Leu Tyr
1               5                   10                  15

Phe Ile Lys Pro Leu
            20

<210> SEQ ID NO 183
<211> LENGTH: 21
<212> TYPE: PRT
<213> ORGANISM: artificial
<220> FEATURE:
<223> OTHER INFORMATION: homocitrulline containing Fibrinogen gamma
      counterpart
<220> FEATURE:
<221> NAME/KEY: MISC_FEATURE
<222> LOCATION: (8)..(8)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (19)..(19)
<223> OTHER INFORMATION: homocitrulline

<400> SEQUENCE: 183

Asp Cys Gln Asp Ile Ala Asn Xaa Gly Ala Xaa Gln Ser Gly Leu Tyr
1               5                   10                  15

Phe Ile Xaa Pro Leu
            20

<210> SEQ ID NO 184
```

```
<211> LENGTH: 21
<212> TYPE: PRT
<213> ORGANISM: homo sapiens

<400> SEQUENCE: 184

Gly Ala Lys Gln Ser Gly Leu Tyr Phe Ile Lys Pro Leu Lys Ala Asn
1               5                   10                  15

Gln Gln Phe Leu Val
            20

<210> SEQ ID NO 185
<211> LENGTH: 21
<212> TYPE: PRT
<213> ORGANISM: artificial
<220> FEATURE:
<223> OTHER INFORMATION: homocitrulline containing Fibrinogen gamma
      counterpart
<220> FEATURE:
<221> NAME/KEY: MISC_FEATURE
<222> LOCATION: (3)..(3)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (14)..(14)
<223> OTHER INFORMATION: homocitrulline

<400> SEQUENCE: 185

Gly Ala Xaa Gln Ser Gly Leu Tyr Phe Ile Xaa Pro Leu Xaa Ala Asn
1               5                   10                  15

Gln Gln Phe Leu Val
            20

<210> SEQ ID NO 186
<211> LENGTH: 21
<212> TYPE: PRT
<213> ORGANISM: homo sapiens

<400> SEQUENCE: 186

Gly Ser Gly Asn Gly Trp Thr Val Phe Gln Lys Arg Leu Asp Gly Ser
1               5                   10                  15

Val Asp Phe Lys Lys
            20

<210> SEQ ID NO 187
<211> LENGTH: 21
<212> TYPE: PRT
<213> ORGANISM: artificial
<220> FEATURE:
<223> OTHER INFORMATION: homocitrulline containing Fibrinogen gamma
      counterpart
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (20)..(20)
<223> OTHER INFORMATION: homocitrulline
<220> FEATURE:
<221> NAME/KEY: MISC_FEATURE
<222> LOCATION: (21)..(21)
<223> OTHER INFORMATION: homocitrulline

<400> SEQUENCE: 187

Gly Ser Gly Asn Gly Trp Thr Val Phe Gln Xaa Arg Leu Asp Gly Ser
```

```
1               5                   10                  15

Val Asp Phe Xaa Xaa
            20

<210> SEQ ID NO 188
<211> LENGTH: 21
<212> TYPE: PRT
<213> ORGANISM: homo sapiens

<400> SEQUENCE: 188

Gln Lys Arg Leu Asp Gly Ser Val Asp Phe Lys Lys Asn Trp Ile Gln
1               5                   10                  15

Tyr Lys Glu Gly Phe
            20

<210> SEQ ID NO 189
<211> LENGTH: 21
<212> TYPE: PRT
<213> ORGANISM: artificial
<220> FEATURE:
<223> OTHER INFORMATION: homocitrulline containing Fibrinogen gamma
      counterpart
<220> FEATURE:
<221> NAME/KEY: MISC_FEATURE
<222> LOCATION: (2)..(2)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (12)..(12)
<223> OTHER INFORMATION: homocitrulline
<220> FEATURE:
<221> NAME/KEY: MISC_FEATURE
<222> LOCATION: (18)..(18)
<223> OTHER INFORMATION: homocitrulline

<400> SEQUENCE: 189

Gln Xaa Arg Leu Asp Gly Ser Val Asp Phe Xaa Xaa Asn Trp Ile Gln
1               5                   10                  15

Tyr Xaa Glu Gly Phe
            20

<210> SEQ ID NO 190
<211> LENGTH: 21
<212> TYPE: PRT
<213> ORGANISM: homo sapiens

<400> SEQUENCE: 190

Lys Arg Leu Asp Gly Ser Val Asp Phe Lys Lys Asn Trp Ile Gln Tyr
1               5                   10                  15

Lys Glu Gly Phe Gly
            20

<210> SEQ ID NO 191
<211> LENGTH: 21
<212> TYPE: PRT
<213> ORGANISM: artificial
<220> FEATURE:
<223> OTHER INFORMATION: homocitrulline containing Fibrinogen gamma
      counterpart
<220> FEATURE:
<221> NAME/KEY: MISC_FEATURE
<222> LOCATION: (1)..(1)
<223> OTHER INFORMATION: homocitrulline
<220> FEATURE:
```

```
<221> NAME/KEY: MISC_FEATURE
<222> LOCATION: (10)..(10)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (17)..(17)
<223> OTHER INFORMATION: homocitrulline

<400> SEQUENCE: 191

Xaa Arg Leu Asp Gly Ser Val Asp Phe Xaa Xaa Asn Trp Ile Gln Tyr
1               5                   10                  15

Xaa Glu Gly Phe Gly
            20

<210> SEQ ID NO 192
<211> LENGTH: 21
<212> TYPE: PRT
<213> ORGANISM: homo sapiens

<400> SEQUENCE: 192

Val Asp Phe Lys Lys Asn Trp Ile Gln Tyr Lys Glu Gly Phe Gly His
1               5                   10                  15

Leu Ser Pro Thr Gly
            20

<210> SEQ ID NO 193
<211> LENGTH: 21
<212> TYPE: PRT
<213> ORGANISM: artificial
<220> FEATURE:
<223> OTHER INFORMATION: homocitrulline containing Fibrinogen gamma
      counterpart
<220> FEATURE:
<221> NAME/KEY: MISC_FEATURE
<222> LOCATION: (4)..(4)
<223> OTHER INFORMATION: homocitrulline
<220> FEATURE:
<221> NAME/KEY: MISC_FEATURE
<222> LOCATION: (5)..(5)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline

<400> SEQUENCE: 193

Val Asp Phe Xaa Xaa Asn Trp Ile Gln Tyr Xaa Glu Gly Phe Gly His
1               5                   10                  15

Leu Ser Pro Thr Gly
            20

<210> SEQ ID NO 194
<211> LENGTH: 21
<212> TYPE: PRT
<213> ORGANISM: homo sapiens

<400> SEQUENCE: 194

Gly Thr Thr Glu Phe Trp Leu Gly Asn Glu Lys Ile His Leu Ile Ser
1               5                   10                  15

Thr Gln Ser Ala Ile
            20

<210> SEQ ID NO 195
```

```
<211> LENGTH: 21
<212> TYPE: PRT
<213> ORGANISM: artificial
<220> FEATURE:
<223> OTHER INFORMATION: homocitrulline containing Fibrinogen gamma
      counterpart
<220> FEATURE:
<221> NAME/KEY: MISC_FEATURE
<222> LOCATION: (11)..(11)
<223> OTHER INFORMATION: homocitrulline

<400> SEQUENCE: 195

Gly Thr Thr Glu Phe Trp Leu Gly Asn Glu Xaa Ile His Leu Ile Ser
1               5                   10                  15

Thr Gln Ser Ala Ile
            20

<210> SEQ ID NO 196
<211> LENGTH: 21
<212> TYPE: PRT
<213> ORGANISM: homo sapiens

<400> SEQUENCE: 196

Arg Thr Ser Thr Ala Asp Tyr Ala Met Phe Lys Val Gly Pro Glu Ala
1               5                   10                  15

Asp Lys Tyr Arg Leu
            20

<210> SEQ ID NO 197
<211> LENGTH: 21
<212> TYPE: PRT
<213> ORGANISM: artificial
<220> FEATURE:
<223> OTHER INFORMATION: homocitrulline containing Fibrinogen gamma
      counterpart
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (18)..(18)
<223> OTHER INFORMATION: homocitrulline

<400> SEQUENCE: 197

Arg Thr Ser Thr Ala Asp Tyr Ala Met Phe Xaa Val Gly Pro Glu Ala
1               5                   10                  15

Asp Xaa Tyr Arg Leu
            20

<210> SEQ ID NO 198
<211> LENGTH: 21
<212> TYPE: PRT
<213> ORGANISM: homo sapiens

<400> SEQUENCE: 198

Ala Met Phe Lys Val Gly Pro Glu Ala Asp Lys Tyr Arg Leu Thr Tyr
1               5                   10                  15

Ala Tyr Phe Ala Gly
            20

<210> SEQ ID NO 199
<211> LENGTH: 21
<212> TYPE: PRT
<213> ORGANISM: artificial
<220> FEATURE:
<223> OTHER INFORMATION: homocitrulline containing Fibrinogen gamma
```

```
    counterpart
<220> FEATURE:
<221> NAME/KEY: MISC_FEATURE
<222> LOCATION: (4)..(4)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline

<400> SEQUENCE: 199

Ala Met Phe Xaa Val Gly Pro Glu Ala Asp Xaa Tyr Arg Leu Thr Tyr
1               5                  10                  15

Ala Tyr Phe Ala Gly
            20

<210> SEQ ID NO 200
<211> LENGTH: 21
<212> TYPE: PRT
<213> ORGANISM: homo sapiens

<400> SEQUENCE: 200

Gly Phe Asp Phe Gly Asp Asp Pro Ser Asp Lys Phe Phe Thr Ser His
1               5                  10                  15

Asn Gly Met Gln Phe
            20

<210> SEQ ID NO 201
<211> LENGTH: 21
<212> TYPE: PRT
<213> ORGANISM: artificial
<220> FEATURE:
<223> OTHER INFORMATION: homocitrulline containing Fibrinogen gamma
      counterpart
<220> FEATURE:
<221> NAME/KEY: MISC_FEATURE
<222> LOCATION: (11)..(11)
<223> OTHER INFORMATION: homocitrulline

<400> SEQUENCE: 201

Gly Phe Asp Phe Gly Asp Asp Pro Ser Asp Xaa Phe Phe Thr Ser His
1               5                  10                  15

Asn Gly Met Gln Phe
            20

<210> SEQ ID NO 202
<211> LENGTH: 21
<212> TYPE: PRT
<213> ORGANISM: homo sapiens

<400> SEQUENCE: 202

Gln Phe Ser Thr Trp Asp Asn Asp Asn Asp Lys Phe Glu Gly Asn Cys
1               5                  10                  15

Ala Glu Gln Asp Gly
            20

<210> SEQ ID NO 203
<211> LENGTH: 21
<212> TYPE: PRT
<213> ORGANISM: artificial
<220> FEATURE:
<223> OTHER INFORMATION: homocitrulline containing Fibrinogen gamma
      counterpart
<220> FEATURE:
<221> NAME/KEY: MISC_FEATURE
<222> LOCATION: (11)..(11)
<223> OTHER INFORMATION: homocitrulline
```

```
<400> SEQUENCE: 203

Gln Phe Ser Thr Trp Asp Asn Asp Asn Asp Xaa Phe Glu Gly Asn Cys
1               5                   10                  15

Ala Glu Gln Asp Gly
            20

<210> SEQ ID NO 204
<211> LENGTH: 21
<212> TYPE: PRT
<213> ORGANISM: homo sapiens

<400> SEQUENCE: 204

Glu Gln Asp Gly Ser Gly Trp Trp Met Asn Lys Cys His Ala Gly His
1               5                   10                  15

Leu Asn Gly Val Tyr
            20

<210> SEQ ID NO 205
<211> LENGTH: 21
<212> TYPE: PRT
<213> ORGANISM: artificial
<220> FEATURE:
<223> OTHER INFORMATION: homocitrulline containing Fibrinogen gamma
      counterpart
<220> FEATURE:
<221> NAME/KEY: MISC_FEATURE
<222> LOCATION: (11)..(11)
<223> OTHER INFORMATION: homocitrulline

<400> SEQUENCE: 205

Glu Gln Asp Gly Ser Gly Trp Trp Met Asn Xaa Cys His Ala Gly His
1               5                   10                  15

Leu Asn Gly Val Tyr
            20

<210> SEQ ID NO 206
<211> LENGTH: 21
<212> TYPE: PRT
<213> ORGANISM: homo sapiens

<400> SEQUENCE: 206

Gly Val Tyr Tyr Gln Gly Gly Thr Tyr Ser Lys Ala Ser Thr Pro Asn
1               5                   10                  15

Gly Tyr Asp Asn Gly
            20

<210> SEQ ID NO 207
<211> LENGTH: 21
<212> TYPE: PRT
<213> ORGANISM: artificial
<220> FEATURE:
<223> OTHER INFORMATION: homocitrulline containing Fibrinogen gamma
      counterpart
<220> FEATURE:
<221> NAME/KEY: MISC_FEATURE
<222> LOCATION: (11)..(11)
<223> OTHER INFORMATION: homocitrulline

<400> SEQUENCE: 207

Gly Val Tyr Tyr Gln Gly Gly Thr Tyr Ser Xaa Ala Ser Thr Pro Asn
1               5                   10                  15

Gly Tyr Asp Asn Gly
            20
```

<210> SEQ ID NO 208
<211> LENGTH: 21
<212> TYPE: PRT
<213> ORGANISM: homo sapiens

<400> SEQUENCE: 208

Tyr Asp Asn Gly Ile Ile Trp Ala Thr Trp Lys Thr Arg Trp Tyr Ser
1               5                   10                  15

Met Lys Lys Thr Thr
            20

<210> SEQ ID NO 209
<211> LENGTH: 21
<212> TYPE: PRT
<213> ORGANISM: artificial
<220> FEATURE:
<223> OTHER INFORMATION: homocitrulline containing Fibrinogen gamma
      counterpart
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (18)..(18)
<223> OTHER INFORMATION: homocitrulline
<220> FEATURE:
<221> NAME/KEY: MISC_FEATURE
<222> LOCATION: (19)..(19)
<223> OTHER INFORMATION: homocitrulline

<400> SEQUENCE: 209

Tyr Asp Asn Gly Ile Ile Trp Ala Thr Trp Xaa Thr Arg Trp Tyr Ser
1               5                   10                  15

Met Xaa Xaa Thr Thr
            20

<210> SEQ ID NO 210
<211> LENGTH: 21
<212> TYPE: PRT
<213> ORGANISM: homo sapiens

<400> SEQUENCE: 210

Ala Thr Trp Lys Thr Arg Trp Tyr Ser Met Lys Lys Thr Thr Met Lys
1               5                   10                  15

Ile Ile Pro Phe Asn
            20

<210> SEQ ID NO 211
<211> LENGTH: 21
<212> TYPE: PRT
<213> ORGANISM: artificial
<220> FEATURE:
<223> OTHER INFORMATION: homocitrulline containing Fibrinogen gamma
      counterpart
<220> FEATURE:
<221> NAME/KEY: MISC_FEATURE
<222> LOCATION: (4)..(4)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (12)..(12)
<223> OTHER INFORMATION: homocitrulline
<220> FEATURE:
<221> NAME/KEY: MISC_FEATURE

```
<222> LOCATION: (16)..(16)
<223> OTHER INFORMATION: homocitrulline

<400> SEQUENCE: 211

Ala Thr Trp Xaa Thr Arg Trp Tyr Ser Met Xaa Xaa Thr Thr Met Xaa
1               5                   10                  15

Ile Ile Pro Phe Asn
            20

<210> SEQ ID NO 212
<211> LENGTH: 21
<212> TYPE: PRT
<213> ORGANISM: homo sapiens

<400> SEQUENCE: 212

Thr Trp Lys Thr Arg Trp Tyr Ser Met Lys Lys Thr Thr Met Lys Ile
1               5                   10                  15

Ile Pro Phe Asn Arg
            20

<210> SEQ ID NO 213
<211> LENGTH: 21
<212> TYPE: PRT
<213> ORGANISM: artificial
<220> FEATURE:
<223> OTHER INFORMATION: homocitrulline containing Fibrinogen gamma
      counterpart
<220> FEATURE:
<221> NAME/KEY: MISC_FEATURE
<222> LOCATION: (3)..(3)
<223> OTHER INFORMATION: homocitrulline
<220> FEATURE:
<221> NAME/KEY: MISC_FEATURE
<222> LOCATION: (10)..(10)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline
<220> FEATURE:
<221> NAME/KEY: MISC_FEATURE
<222> LOCATION: (15)..(15)
<223> OTHER INFORMATION: homocitrulline

<400> SEQUENCE: 213

Thr Trp Xaa Thr Arg Trp Tyr Ser Met Xaa Xaa Thr Thr Met Xaa Ile
1               5                   10                  15

Ile Pro Phe Asn Arg
            20

<210> SEQ ID NO 214
<211> LENGTH: 21
<212> TYPE: PRT
<213> ORGANISM: homo sapiens

<400> SEQUENCE: 214

Arg Trp Tyr Ser Met Lys Lys Thr Thr Met Lys Ile Ile Pro Phe Asn
1               5                   10                  15

Arg Leu Thr Ile Gly
            20

<210> SEQ ID NO 215
<211> LENGTH: 21
<212> TYPE: PRT
<213> ORGANISM: artificial
<220> FEATURE:
<223> OTHER INFORMATION: homocitrulline containing Fibrinogen gamma
```

```
                        counterpart
<220> FEATURE:
<221> NAME/KEY: MISC_FEATURE
<222> LOCATION: (6)..(6)
<223> OTHER INFORMATION: homocitrulline
<220> FEATURE:
<221> NAME/KEY: MISC_FEATURE
<222> LOCATION: (7)..(7)
<223> OTHER INFORMATION: homocitrulline
<220> FEATURE:
<221> NAME/KEY: MISC_FEATURE
<222> LOCATION: (11)..(11)
<223> OTHER INFORMATION: homocitrulline

<400> SEQUENCE: 215

Arg Trp Tyr Ser Met Xaa Xaa Thr Thr Met Xaa Ile Ile Pro Phe Asn
1               5                   10                  15

Arg Leu Thr Ile Gly
                20
```

ANTI-CARBAMYLATED PROTEIN ANTIBODIES AND THE RISK FOR ARTHRITIS

CROSS-REFERENCE TO RELATED APPLICATIONS

This application is a national phase entry under 35 U.S.C. §371 of International Patent Application PCT/NL2012/050056, filed Feb. 1, 2012, designating the United States of America and published in English as International Patent Publication WO 2012/105838 A1 on Aug. 9, 2012, which claims the benefit under Article 8 of the Patent Cooperation Treaty and under 35 U.S.C. §119(e) to European Patent Application Serial No. 11182399.3, filed Sep. 22, 2011, and to European Patent Application Serial No. 11153046.5, filed Feb. 2, 2011.

STATEMENT ACCORDING TO 37 C.F.R. §1.821(c) OR (e)—SEQUENCE LISTING SUBMITTED AS A TXT AND PDF FILES

Pursuant to 37 C.F.R. §1.821(c) or (e), files containing a TXT version and a PDF version of the Sequence Listing have been submitted concomitant with this application, the contents of which are hereby incorporated by reference.

TECHNICAL FIELD

The disclosure relates to the fields of post-translational modification and arthritis. In particular, it relates to methods classifying samples of individuals based on the detection of post-translationally modified proteins or peptides or antibodies specific for post-translationally modified proteins or peptides in a sample containing a body fluid of the individual.

BACKGROUND

There are over 100 different forms of arthritis. The most common form is osteoarthritis (degenerative joint disease). Osteoarthritis is most commonly the result of a trauma or of an infection of the joint, albeit that there are also not readily identifiable causes. The latter are often collectively referred to as "age-related osteoarthritis." Other forms of arthritis are, for example, rheumatoid arthritis, psoriatic arthritis, and related autoimmune diseases.

The major complaint by individuals who have arthritis is joint pain. Pain is often constant and may be localized to the joint affected. The pain from arthritis is often the result of damage to the joint or the result of the inflammation that occurs around the joint. Other complaints are pain as a result of muscle strains caused by forceful movements against stiff, painful joints and fatigue.

The diagnosis of patients with joint-associated pain is not easy as the complaints are typically vague and can be attributed to a variety of different causes, some of which are not arthritis. Indeed, many patients that first see a doctor with joint pain-associated complaints go into remission and don't develop a chronic form of arthritis, whereas a significant minority progress to develop Rheumatoid Arthritis (RA). It is clear that individuals that go into remission spontaneously do not need to receive treatment, whereas individuals that progress would benefit considerably from early treatment. To discriminate between the respective groups, the field has developed a series of tests with which the diagnosis of arthritis can be made with more certainty.

Such tests presently involve the screening of tissue samples and/or body fluid samples for the presence of arthritis indicators therein. Such indicators are, among others, determination of "chronic" inflammation indicators such as, for instance, certain chemokines, cytokines and other immune cell signaling factors; the determination of "accumulation of" active immune cells in joints, and/or the presence of the certain factors in the blood, the most notable of which is rheumatoid factor. Recently, tests directed toward the detection of citrullinated protein or peptides or antibodies specific for such citrullinated protein or peptide have been developed as a useful tool for such tests. The availability of such tests has greatly improved the diagnosis of individuals suspected of having a form of arthritis. These tests also aid the clinician in giving a more accurate prognosis for the future development of the disease to individuals suffering from arthritis. However, in spite of these developments, the diagnosis of arthritis or individuals at risk thereof still leaves much to be desired.

For example, in the Netherlands, the recommendation to diagnose RA is based on a probability score generated by the ACR/EULAR 2010 criteria. This criteria combines clinical features such as involvement of type and number of joints, presence or absence of the serological factors, rheumatoid factor and anti-CCP antibodies, presence or absence of acute phase proteins such as CRP, and duration of complaints. Patients that are diagnosed with RA according to this protocol need to have more than six points. The fact that only the clinical involvement and duration of complaints are sufficient for a positive diagnosis indicates that the arthritis population is very heterogeneous and, in fact, often a wrong diagnosis is made.

In the Netherlands and in other countries, tests for the typing of arthritis or diagnoses of an individual at risk of developing arthritis presently include tests for the detection of antibodies specific for citrullinated protein or peptide in samples of body fluids of such patients. These tests have led to the insight that arthritis patients can be classified on the basis of positivity for antibodies directed toward citrullinated proteins (ACPA). The identification of ACPA has had an important impact on the understanding of RA.[1] Major differences have been observed when comparing ACPA-positive vs. ACPA-negative RA patients regarding genetic and environmental risk factors,[2] progression,[3] remission,[4] and response to treatment.[5] Over the recent years, much more insight has been gained into the occurrence and etiopathology of ACPA-positive RA. However, much less information is available on ACPA-negative RA. In part, this is because it is relatively difficult to identify or even subgroup these individuals as no good assays are currently available. Interestingly, rituximab treatment has been reported to also be beneficial in patients negative for RF and ACPA.[6, 7]

The post-translational modification of arginine residues into citrulline residues by the PAD enzymes is the essential step to generate antigens for ACPA.[1] Under physiological circumstances, this citrullination is important in tissues like hair and skin to generate layers of tissue that are not-well connected.[8] Also, in the nucleus, citrullination plays a role in epigenetic regulation[9] and condensation of chromatin, which is important, both in translation[8] and in host defense against pathogens.[10] Under pathological conditions where cell death may overwhelm the phagocytic capacity, necrotic cell death may release PAD into the extracellular space, where higher calcium concentrations now also allow other host molecules to become citrullinated.[8] Since many of these molecules will be presented to the immune system as non-self, it can induce an antibody response in some individuals. Citrulline highly resembles (FIG. 1) another post-translationally modified amino acid called homocitrulline.[11] Homocitrulline is only one carbon longer, but similar in structure.[11] Homocitrulline is generated from a Lysine residue following an attack from cyanate, which exists in the body in equilibrium with urea. Under physiological conditions, the urea concentration may be too low to allow extensive carbamylation (the process of changing lysine to homocitrulline). In conditions of renal failure, the urea concentration increases and carbamylation can be readily detected. However, most carbamylation is taking place during inflammation when myeloperoxidase (MPO) is released from neutrophils.[12] This enzyme strongly shifts the equilibrium of urea toward cyanate, now allowing more carbamylation to occur.[13] It has been shown recently that homocitrulline-containing proteins are present in the RA joint and that this may affect T-cell triggering and autoantibody formation in animal models.[11, 14] Although highly similar, carbamylation differs from citrullination as, next to their structural difference, lysine and not arginine is modified. Therefore, homocitrulline will, by definition, be located at other positions in proteins than citrulline.

DISCLOSURE

Autoantibodies against carbamylated proteins have been found to be present in arthritis, and it has been determined that measurement of such antibodies is useful in the diagnosis, prognosis, and management (e.g., treatment) of early arthritis and RA. Thus, provided is a method for classifying an individual that is suffering from, or at risk of suffering from, a faun of arthritis, the method comprising determining whether a sample comprising a body fluid of the individual comprises an anti-Carbamylated Protein (anti-CarP) antibody.

An individual that is suffering from arthritis can be classified, on the basis of anti-CarP antibodies, as low or high risk of developing a more severe form of arthritis. Individuals with arthritis that are positive for anti-CarP tend to develop a more severe form of arthritis than anti-CarP-negative individuals with arthritis, at least within any given time period. The anti-CarP-positive individuals also tend to progress into more severe forms more quickly when compared with anti-CarP-negative individuals. The method is thus preferably used to allocate an individual that is suffering from a form of arthritis to a group with a lower or a higher than average risk for progressing to a more severe or chronic form of arthritis. In a preferred embodiment, the individual is suffering from undifferentiated arthritis at presentation. In a preferred aspect of this embodiment, the more severe or chronic form is RA. In another preferred aspect of this embodiment, the more severe or chronic form is juvenile arthritis, preferably juvenile idiopathic arthritis. In a preferred embodiment, the group with a lower than average risk is a group that has a higher than average incidence of spontaneous remission of the arthritis complaints.

The at-risk population may be healthy individuals, patients suffering from undifferentiated arthritis or arthralgia, autoantibody-positive individuals with joint complaints, autoantibody-positive individuals, or family members from patients with arthritis. "Juvenile idiopathic arthritis" is the term used for a subset of arthritis seen in childhood, which may be transient and self-limiting or chronic. Children with juvenile idiopathic arthritis are considered an at-risk population, as some of these patients may develop a chronic form of arthritis.

The application shows that detection of anti-CarP antibodies is useful in individuals that present with undifferentiated arthritis, arthralgia, and other joint complaints, and/or with juvenile arthritis. The presence or absence of anti-CarP antibodies is predictive of the development of RA or persistent arthritis later in life. This predictive power is observed both in ACPA-negative and ACPA-positive subjects.

The method may be used to predict whether the individual is at risk of developing RA or persistent arthritis later in life.

For instance, human carbamylated fibrinogen can be used as a target for anti-CarP antibodies. Carbamylated fibrinogen is recognized by both IgG and IgA anti-CarP antibodies. Intact fibrinogen, or any of peptides derived from carbamylated fibrinogen, can be used as targets in assays to detect anti-CarP antibodies. The intact protein or any of the peptides derived from fibrinogen can be used directly in the assay or can be immobilized via an attached biotin group that will bind to streptavidin-coated surfaces or can be used in any other way to detect anti-CarP antibodies. In a preferred embodiment, a method according to the invention is provided, wherein the anti-CarP antibody is capable of specifically binding carbamylated fibrinogen. Throughout the description, the abbreviation "anti-Ca-Fib antibody" is used to indicate such antibody capable of specifically binding carbamylated fibrinogen.

Progression of disease in arthritis, for instance, progressive pain complaints or progressive joint damage, is not a constant. The progression may be faster or slower for some period of time. When mention is made herein of a lower or higher risk of progression, this is typically compared to the average risk of progression within the group of individuals that is studied.

Progression of diseases is at a group level established every year, so that follow-up data can be analyzed using repeated measurement analysis. Yet, at the individual levels, positivity for anti-CarP, preferably anti-Ca-Fib, is predictive for future progression. Currently, several methods including MRI, ultrasound and other techniques are available to measure progression of disease in the short term.

To assess whether a sample comprises anti-CarP antibodies, preferably anti-Ca-Fib antibodies, a test for the presence of the antibodies is performed. Such tests can involve, but are not limited to, ELISA and/or Western blot, using one or several carbamylated proteins and/or peptides. Commonly, though not necessarily, the result obtained for the sample is compared with a reference. The reference is typically the result of a similar test, preferably the same test, performed on one or a number of healthy individuals (i.e., not known to suffer from arthritis and not known to be at immediate risk of developing arthritis). The result of the sample can be directly compared with the result of the reference, or the reference can be used to determine a threshold, below which any sample is to be judged a negative for anti-CarP, preferably anti-Ca-Fib, antibodies when below the threshold or positive when above the threshold.

Further provided is a method for providing a prognosis for the development of arthritis to an individual suffering from arthritis, the method comprising determining whether a sample comprising a body fluid of the individual comprises an anti-Carbamylated Protein (anti-CarP) antibody, and estimating the future severity of the arthritis based on the detection of the anti-CarP antibody in the sample. In a preferred embodiment, the anti-CarP antibody is capable of specifically binding carbamylated fibrinogen (anti-Ca-Fib antibody). This estimation is typically accompanied by a time interval within which the more severe form or progression becomes apparent or not (see hereinabove).

One advantage of the classifications as indicated hereinbefore is that the groups of individuals have more homogeneous genetic profile within each group than with other methods. Another advantage is that the groups of individuals are more homogeneous in their response to (prophylactic) treatment. Since it has been shown that early aggressive treatment is beneficial[18, 19] provided are methods for arthritis treatment of individuals suffering from, or at risk of suffering from, arthritis, the method comprising an arthritis diagnosis of the individual wherein the diagnosis comprises a method for determining an anti-CarP antibody, preferably an anti-Ca-Fib antibody, in a sample comprising a body fluid of the individual. Preferably, the sample was determined to contain an anti-CarP antibody, preferably an anti-Ca-Fib antibody. A more stringent treatment of the anti-CarP or anti-Ca-Fib-positive individual is beneficial to the patient. The treatment is typically a therapeutic treatment given to a patient that was diagnosed with arthritis prior to receiving the treatment. Further provided is a method of treating an individual suffering from arthritis with an arthritis medication and/or treatment, the method characterized in that the individual was diagnosed with a method hereof prior to the treatment. Preferably, the individual was diagnosed as suffering from arthritis with a method for classifying individuals suffering from arthritis of the invention, prior to receiving the arthritis medication and/or treatment. Further provided is a method for the prophylactic treatment of an individual at risk of developing arthritis with an arthritis medication and/or treatment, the method characterized in that the individual was diagnosed being at risk of developing arthritis with a method for classifying individuals of the invention, prior to receiving the arthritis medication and/or treatment. Treatment, in this case, prophylactic, can also be given to individuals that are classified to be at risk of developing the disease in the near future, typically within one year of classification. Such prophylactic treatments are capable of at least postponing the onset of the disease and/or reducing the severity of the disease.

The methods used to classify arthritis patients or individuals at risk of developing arthritis typically involve a number of different tests. Such tests may also be combined with a method of the invention to arrive at a more accurate assessment of the classification. To this end, the invention further provides means and methods to further classify individuals that suffer from arthritis or that are suspected/at risk of having arthritis. In a preferred embodiment, a method of the invention is combined with a test for Anti-Citrullinated Protein Antibodies (ACPA).

The ACPA test has been used for quite some time (reviewed, among others, in Venrooij et al. "Anticitrullinated protein/peptide antibody and its role in the diagnosis and prognosis of early rheumatoid arthritis," *The Netherlands Journal of Medicine*, 2002, 60:383-388; and L. Klareskog, J. Ronnelid, K. Lundberg, L. Padyukov, and L. Alfredsson, "Immunity to citrullinated proteins in rheumatoid arthritis," *Annu. Rev. Immunol.* 2008, 26:651-75.

Many different citrullinated proteins or peptides can be used in tests to detect anti-citrullinated protein antibodies (ACPA). Citrullinated filaggrin has been used to detect the so-called anti-filaggrin antibodies (AFA). In first attempts to find suitable substrates for RA auto-antibodies, a number of linear peptides containing one citrulline residue were developed. These citrullinated peptides were specifically recognized by the RA auto-antibodies and, more important, their arginine-containing counterparts were not. However, most peptides reacted with only 30 to 45% of the RA sera, although more than 75% of RA sera reacted with at least one of a total of nine peptides tested (Schellekens et al. (1998), *J. Clin. Invest.* 101:271-281). Although linear peptides may be used, it has been found that cyclic peptides render the tests more sensitive. Tests that include cyclic citrullinated protein/peptide are typically referred to as CCP tests. The CCP1 test was already sensitive, but it has been found that a novel selection of cyclic citrullinated protein/peptides with improved immune recognition properties has increased the sensitivity of the CCP test to at least 80%. This latter test is typically referred to as the CCP2 test. Thus, in one embodiment hereof, the method for detecting ACPA comprises detecting anti-cyclic citrullinated protein/peptide in the sample. Preferably, the method for detecting ACPA is a CCP2 test as described in G. J. Pruijn, A. Wiik, and W. J. van Venrooij, "The use of citrullinated peptides and proteins for the diagnosis of rheumatoid arthritis, *Arthritis Res. Ther.* 2010, 12(1):203, Epub. 2010 Feb. 15; and F. A. van Gaalen, H. Visser, and T. W. Huizinga, "Review and a comparison of the diagnostic accuracy and prognostic value of the first and second anti-cyclic citrullinated peptides (CCP1 and CCP2) autoantibody tests for rheumatoid arthritis," *Ann. Rheum. Dis.*, October 2005, 64(10):1510-2.

As is the case for ACPA, also for an anti-CarP antibody in principle, many different carbamylated proteins or peptides can be used in tests to detect anti-carbamylated protein antibodies. In a preferred embodiment, the carbamylated protein or peptide is a cyclic peptide. A good source of carbamylated proteins is carbamylated fetal calf serum. Serum proteins from other species are, however, also suitable. Following optimization, human proteins might also be used. For reasons of inevitable background, human serum cannot be used in carbamylated form without extensive depletion of Ig. In a preferred embodiment, the carbamylated protein is fibrinogen, preferably human fibrinogen.

A peptide for use in a method hereof, be it for the detection of ACPA in general or of anti-CarP antibodies or of anti-Ca-Fib antibodies, is typically a peptide of between 6 and 50 amino acids. Preferably, the peptide is a peptide of between 12 and 30 amino acids, more preferably of between 18 and 22 amino acids, most preferably of about 21 amino acids. The mentioned ranges include the number mentioned, i.e., a range of between 12 and 30 amino acids includes peptides of 12 and 30 amino acids, respectively. The peptide may or may not be a cyclic peptide depending on the sensitivity and/or specificity than the comparable linear peptide. Circular peptides can be generated in any molecular composition as to generate the cyclic nature. Any method may be used to couple peptides and or proteins in carbamylated, citrullinated or native form to plates and/or beads, being either direct coating or using biotin-streptavidin or any other available coating method.

In a preferred embodiment, such peptide for use in a method of the invention is a peptide derived from human fibrinogen. The peptide preferably comprises a contiguous amino acid of between 12 and 30 amino acids, more preferably of between 18 and 22 amino acids, most preferably of about 21 amino acids present in the amino acid sequence of any one of fibrinogen alpha (FIG. 14), fibrinogen beta (FIG. 15) or fibrinogen gamma (FIG. 16). In a more preferred embodiment, the peptide is any one of the peptides depicted in Table I, Table II, or Table III.

Further provided is, as indicated hereinabove, a method for classifying an individual that is suffering from, or at risk of suffering from, a form of arthritis, the method comprising determining whether a sample comprising a body fluid of the individual comprises an anti-CarP antibody, preferably an anti-Ca-Fib antibody, and determining whether the sample comprises Anti-Citrullinated Protein Antibodies (ACPA) and classifying the individual on the basis of the detection of the anti-CarP antibody and/or the ACPA.

The anti-CarP antibody, the anti-Ca-Fib antibody, and ACPA can be of any immunoglobulin isotype. The art typically focuses on one or more of the IgG subclasses. In the present invention, it has been found that the level of an anti-CarP antibody, anti-Ca-Fib antibody and/or ACPA of both the Ig-subtype A (IgA) and the Ig-subtype G (IgG) in a sample comprising body fluid of the individual is predictive for clinical outcome measures such as joint destruction. It has also been found that whereas a sample can be negative for anti-CarP or anti-Ca-Fib IgG, it can be positive for anti-CarP or anti-Ca-Fib IgA and vice versa. Thus, in a preferred embodiment of a method hereof, the method comprises determining whether a sample comprising a body fluid of the individual comprises an anti-CarP and/or anti-Ca-Fib antibody of Ig-subtype IgA or an anti-CarP and/or anti-Ca-Fib antibody of Ig-subtype IgG, or both, and wherein detection of the IgA and/or IgG anti-CarP and/or anti-Ca-Fib antibody indicates that the individual is suffering from, or at risk of suffering from, arthritis. In a preferred embodiment, the method further comprises determining whether a sample comprising a body fluid of the individual comprises ACPA. As mentioned hereinabove, a method of the invention is particularly useful in subdividing the heterogeneous group of ACPA-negative individuals. Using a method hereof, this ACPA-negative group can be divided into a group that is anti-CarP and/or anti-Ca-Fib antibody positive and that can be classified as suffering from, or at risk of suffering from, arthritis, and a group that is anti-CarP and/or anti-Ca-Fib antibody negative that can be classified as not suffering from arthritis or not at risk of suffering from arthritis. This determination can also be done on an individual basis. Thus, a method hereof may further comprise determining whether a sample comprising a body fluid of the individual comprises Anti-Citrullinated Protein Antibodies (ACPA) and wherein the level of the ACPA in the sample is below the detection limit and or cut-off of positivity.

A sample of an individual tested for the presence of an anti-CarP antibody, preferably of isotype IgA or of isotype IgG, or both, and ACPA can be classified on the basis of the result as an:
a) an anti-CarP and/or anti-Ca-Fib antibody positive, ACPA-negative sample;
b) an anti-CarP and/or anti-Ca-Fib antibody positive, ACPA-positive sample;
c) an anti-CarP and/or anti-Ca-Fib antibody negative, ACPA-positive; and
d) an anti-CarP and/or anti-Ca-Fib antibody negative, ACPA-negative sample.

Results a), b) and c) classify the sample as a sample of an individual that is at high risk to be currently suffering from, or at risk of developing, arthritis. Result d) classifies the sample as a sample of an individual that has a low risk to be currently suffering from or developing arthritis. In the event that the individual presented with undifferentiated arthritis, then classifying the sample in group d) indicates that the individual has a high chance of spontaneous remission. Such an individual is not expected to benefit on the long term from an anti-arthritis treatment. The invention further provides a method for typing a sample comprising a body fluid of an individual suffering from undifferentiated arthritis, the method comprising determining whether the sample comprises an anti-CarP antibody, preferably an anti-Ca-Fib antibody, and typing the sample as derived from an individual that has a higher than average chance of spontaneous remission of the arthritis when the sample was determined to be negative for the anti-CarP antibody, preferably the anti-Ca-Fib antibody, and typing the sample as derived from an individual that has a higher than average chance of having or progressing to RA when the sample was determined to be positive for the anti-CarP antibody, preferably the anti-Ca-Fib antibody. The higher than average chance is typically arrived at by comparison of the chance with the average chance arrived at for a number of unselected individuals presenting with undifferentiated arthritis.

In another aspect, provided is a method for estimating the severity of arthritis for an individual that is suffering from a form of arthritis and has an increased risk of developing a more severe form of arthritis, the method comprising determining whether a sample comprising a body fluid of the selected individual comprises anti-homocitrulline-Containing Protein antibodies (an anti-CarP antibody), preferably anti-homocitrulline-Containing Fibrinogen antibodies (an anti-Ca-Fib antibody), and estimating the severity of the arthritis based on the detection of the anti-CarP antibodies, preferably, the anti-Ca-Fib antibody in the sample.

In yet another aspect, provided is a method for providing a prognosis for the development of arthritis to an individual suffering from arthritis, the method comprising determining whether a sample comprising a body fluid of the individual comprises an anti-CarP antibody, preferably an anti-Ca-Fib antibody, and estimating the future severity of arthritis based on the detection of the anti-CarP antibody, preferably an anti-Ca-Fib antibody, in the sample. The method is preferably combined with a method for determining ACPA is the sample and the combined result of the anti-CarP and/or anti-Ca-Fib antibody test and the ACPA test is used to estimate the future severity of arthritis for the individual.

The sample to be tested for the presence of an anti-CarP antibody, preferably an anti-Ca-Fib antibody, and/or ACPA can, in principle, be any type of sample as long as it contains body fluid of the individual. Typically, however, the sample is a sample of body fluid. In a preferred embodiment, the sample comprising body fluid is a serum sample or a synovial fluid sample.

Arthritis is, as mentioned hereinabove, a complex disease and many different forms of arthritis have presently been identified. The arthritis that the individual is suffering from or at risk of suffering from is preferably an arthritis selected from rheumatoid arthritis, juvenile arthritis, psoriatic arthritis, osteoarthritis, polymyalgia rheumatica, ankylosing spondylitis, reactive arthritis, gout, pseudogout, autoimmune arthritis, systemic lupus erythematosus, polymyositis, fibromyalgia, Lyme disease, undifferentiated arthritis, non-rheumatoid arthritis or spondyloarthropathy. More preferably, the arthritis that the individual is suffering from or at risk of suffering from is an arthritis selected from rheumatoid arthritis, psoriatic arthritis, osteoarthritis, polymyalgia rheumatica, ankylosing spondylitis, reactive arthritis, gout, pseudogout, autoimmune arthritis, systemic lupus erythematosus, polymyositis, fibromyalgia, Lyme disease, undifferentiated arthritis, non-rheumatoid arthritis or spondyloarthropathy. Preferably, the arthritis is selected from rheumatoid arthritis, juvenile arthritis, more preferably juvenile idiopathic arthritis, or undifferentiated arthritis. More preferably, the arthritis is selected from rheumatoid arthritis or undifferentiated arthritis.

Further provided is a method for typing the arthritis of an individual suffering from a form of arthritis, the method comprising determining whether a sample comprising a body fluid of the individual comprises an anti-Carbamylated Protein (anti-CarP) antibody, preferably an anti-Carbamylated Fibrinogen (anti-Ca-Fib) antibody. The arthritis can be typed on the basis of the detected presence or absence of the anti-CarP and/or anti-Ca-Fib antibody. A sample in which the anti-CarP antibody, preferably the anti-Ca-Fib antibody, is detected is more likely to be derived from an individual with rheumatoid arthritis. Thus, this method can be used alone, or in combination with another test for RA to assess the likelihood that the individual is suffering from RA. In a preferred embodiment, the further test comprises a test for the presence of ACPA, preferably a CCP2 test and or a test for Rheumatoid Factor.

Shown herein is that anti-CarP antibodies can be detected in asymptomatic, healthy individuals before RA development. Thus, detection of anti-CarP antibodies are also useful in the healthy population for the early identification of patients at risk to develop RA or persistent arthritis later in life. In addition, the detection of anti-CarP antibodies is useful to identify persons that would benefit from early treatment, preferably before they fulfill the current classification for RA.

In a further aspect, provided is a method for determining whether an individual is at risk of developing or suffering from a form of arthritis, and wherein the individual was not known to suffer, or preferably not suffering from, arthritis at the time that the sample comprising body fluid was collected, the method comprising determining whether a sample comprising a body fluid of the individual comprises an Anti-Carbamylated Protein (anti-CarP) antibody. In a preferred embodiment, a method hereof is provided wherein the anti-CarP antibody is an Anti-Carbamylated Fibrinogen (anti-Ca-Fib) antibody. A sample in which the anti-CarP antibody, preferably the anti-Ca-Fib antibody, is detected is likely to be derived from an individual that is at risk of suffering from or developing arthritis, in particular RA, in the near future, particularly within five years from the date of sample collection, particularly within three years and more particularly within one and a half years from the date of sample collection. This method can be used alone, or in combination with, another test for RA to assess the risk. In a preferred embodiment, the further test comprises a test for the presence of ACPA, preferably a CCP2 test and/or a test for Rheumatoid Factor.

In another aspect, provided is a kit for the detection of anti-CarP antibodies, preferably anti-Ca-Fib antibodies, in a body fluid of an individual, the kit comprising a carbamylated protein or peptide. Preferably, the carbamylated protein or peptide is carbamylated fibrinogen or a fibrinogen-derived peptide. In a preferred embodiment, the protein or peptide is a carbamylated protein or peptide as indicated hereinabove. In particular, the kit comprises at least one peptide comprising a contiguous amino acid of between 12 and 30 amino acids, more preferably of between 18 and 22 amino acids, most preferably of about 21 amino acids, present in the amino acid sequence of any one of fibrinogen alpha (FIG. 14), fibrinogen beta (FIG. 15) or fibrinogen gamma (FIG. 16). In a more preferred embodiment, the kit comprises at least one of the peptides depicted in Table I, Table II, or Table III.

As also mentioned hereinabove, in a preferred embodiment, the kit further comprises an anti-human IgG antibody and/or an anti-human IgA antibody. Preferably, the anti-human Ig antibody comprises a label that can be detected. Non-limiting examples of such labels are a direct labeling with HRP or AP. Alternatively, the kit preferably further comprises another antibody, which antibody is specific for the anti-human Ig antibody used. In this embodiment, another antibody comprises a label that can be detected, such as biotin or DIG. This nesting can, of course, be continued with label being present on the last and/or one or more (earlier) antibodies. In a preferred embodiment, the anti-human Ig antibody comprises an anti-human IgA antibody. In a more preferred embodiment, the kit comprises an anti-human IgA antibody and an anti-human IgG antibody. The anti-human Ig antibody, as indicated hereinabove, is typically a full antibody; however, a fragment that contains the antigen binding site is also within the use of the term "antibody." Similarly, there are presently a great variety of different binding proteins or peptides available that can be tailored to specifically bind to human Ig. Such human Ig-specific binding proteins or peptides are equivalents of an anti-human Ig antibody as defined herein. Similarly, the one or more further antibodies in a nesting setting can be replaced with binding proteins and/or peptides that specifically bind the earlier antibody and/or binding protein/peptide in the nesting tree.

In a particularly preferred embodiment, the kit further comprises a citrullinated protein or peptide. In a preferred embodiment, the protein or peptide is a citrullinated protein or peptide as indicated hereinabove. As also mentioned hereinabove, the citrullinated protein or peptide is preferably a protein or cyclic peptide. Preferably, the kit comprises a cyclic citrullinated peptide of a CCP1 or CCP2 test. Preferably, the kit comprises all cyclic peptides of a CCP test, preferably a CCP2 test.

A method hereof is, as mentioned hereinabove, preferably combined with another arthritis classifier test. Thus, in a preferred embodiment of a method hereof, the method further comprises determining a further factor as an arthritis classifier for the individual. Preferably, the further factor comprises determining ACPA, rheumatoid factor, C-reactive protein, and/or erythrocyte sedimentation rate.

Carbamylation is defined herein as the process of providing a protein or peptide with a modification that generates a homocitrulline residue. In this document where reference is made to a "carbamylated protein or peptide or collection thereof," reference is made to the protein or peptide having a homocitrulline modification, or a collection of proteins or peptide having homocitrulline modifications.

Further provided is an anti-CarP antibody, preferably an anti-Ca-Fib antibody, and ACPA for use in determining whether an individual is suffering from, or at risk of suffering from, a form of arthritis. The invention further provides an anti-CarP antibody, preferably an anti-Ca-Fib antibody, and ACPA for use in the classification of arthritis, the determining and/or classification being a determining or classification as indicated hereinabove.

Further provided is a method for determining whether an individual that is suffering from a form of arthritis has an increased risk of developing a more severe form of arthritis, the method comprising selecting an individual that is suffering from arthritis but that does not have the most severe form of arthritis and determining whether a sample comprising a body fluid of the selected individual comprises an anti-Carbamylated Protein Antibody (an anti-CarP antibody), wherein detection of the anti-CarP indicates that the individual has increased risk of developing a more severe form of arthritis. In a preferred embodiment, a method according to the invention is provided, wherein the anti-CarP antibody is an anti-Carbamylated Fibrinogen Antibody (an anti-Ca-Fib antibody).

In this document where reference is made to "detection, determination or other assessment" of an anti-CarP antibody, an anti-Ca-Fib antibody or an ACPA, the reference includes that more than one anti-Carp antibody, anti-Ca-Fib antibody and/or more than one ACPA is detected, determined or otherwise assessed. Anti-CarP or anti-Ca-Fib antibody can recognize a homocitrulline modification per se or, more typically, recognize the modification in the context of one or more of the amino acids of the protein or peptide in the immediate vicinity of the homocitrulline modification. A method or kit of the invention is more accurate when anti-CarP antibodies and/or anti-Ca-Fib antibodies of more than one specificity is detected, determined or otherwise assessed. A method of the invention thus preferably comprises determining two or more, and preferably three or more, more preferably five or more, most preferably at least seven anti-CarP and/or anti-Ca-Fib antibodies in the sample. Similarly, a kit of the invention preferably comprises two or more, and preferably three or more, more preferably five or more, most preferably at least seven carbamylated proteins and/or peptides, preferably fibrinogen and/or fibrinogen-derived peptides.

BRIEF DESCRIPTION OF THE DRAWINGS

(FIG. 1A) Dose response curves of the anti-CarP antibody-positive standard on carbamylated FCS and native FCS in ELISA. (FIG. 1 B) Inhibition studies where anti-CarP antibody binding to ELISA plates coated with Ca-FCS was inhibited using pre-incubations with fluid-phase inhibitors as indicated. Only Ca-FCS inhibited the binding of anti-CarP antibodies. (FIG. 1C) Coomassie staining showing equal loading of Ca-FCS and FCS, and Western blot showing a positive staining of Ca-FCS-loaded lanes and not FCS-loaded lanes by a serum sample of an anti-CarP-positive sample and not by a negative sample.

FIG. 12A: Sera of patients that presented with Undifferentiated Arthritis (UA) at baseline were measured for anti-CarP IgG antibodies and analyzed for their conversion toward RA at 1 year follow-up. Data shown are also split up on the basis of ACPA positivity. Anti-CarP antibodies associate strongly with development of RA from a UA population. FIG. 12B: Also in sera of patients that presented with arthralgia at baseline, anti-CarP antibodies are predictive for development of RA. FIG. 12C: Sera of healthy persons that do not develop RA or that do develop RA later in life are compared for anti-CarP positivity. The presence of anti-CarP is associated with future development of RA.

FIG. 14: Amino Acid Sequence of Fibrinogen alpha (SEQ ID NO:1).

FIG. 15: Amino Acid Sequence of Fibrinogen beta (SEQ ID NO:2).

FIG. 16: Amino Acid Sequence of Fibrinogen gamma (SEQ ID NO:3).

DETAILED DESCRIPTION

EXAMPLES

Example 1

Figure 1A:
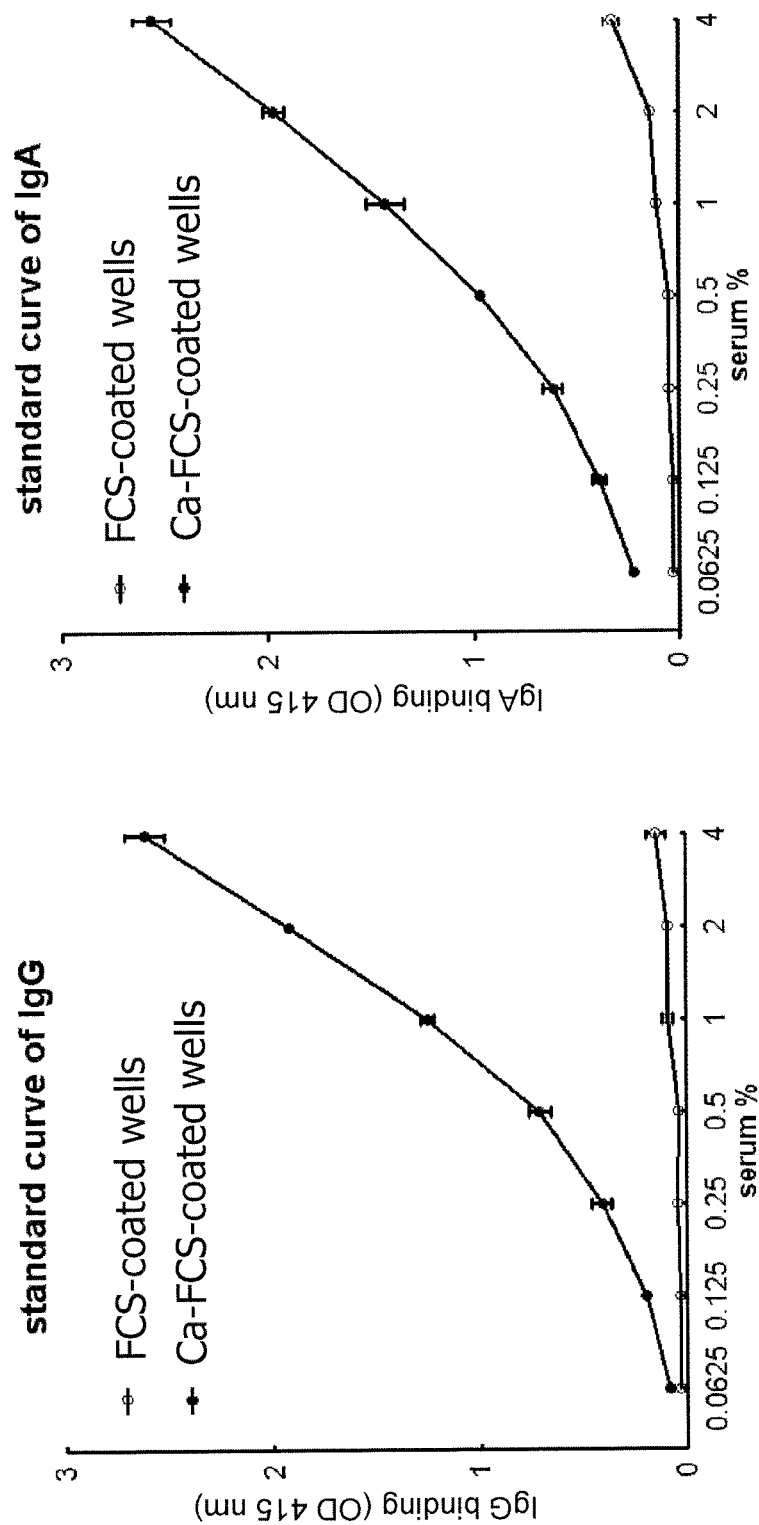
FIGS. 1A through 1C: Development of a novel and specific assay for the detection of anti-CarP antibodies.

Materials and Methods
Generation of Antigens

As a source of antigens, we have used fetal calf serum (FCS) (Bodinco, batch No. 212-192909). This was carbamylated, citrullinated or employed as an unmodified source.

Carbamylated FCS (Ca-FCS) was generated by diluting FCS in bidest to 4 mg/ml. Potassium cyanate (sigma, Cat. No. 215074) was added at 80 mg/ml. Following incubation at 37° C. for 12 hours, the sample was extensively dialyzed against bidest.

As a control, citrullinated FCS (Ci FCS). For this purpose, 50 µl FCS (24 mg/me with 24 µl 0.5 M Tris-HCl pH 7.6+15 µl 0.125 M $CaCl_2$+31 µl PAD4 (Sigma P1584) was incubated for 24 hours at 37° C.

Detection of Anti-CarP Antibodies by ELISA

Non-modified FCS and Ca-FCS were coated at 10 µg/ml (diluted in pH 9.6 0.1 M carbonate-bicarbonate buffer) 50 µl on Nunc immunoplates (Thermo Scientific, Cat. No. 430341), overnight at 4° C. Following washing for four times in phosphate-buffered saline (PBS) containing 0.05% TWEEN® (Sigma, Cat. No. 27,434-8) (PT), the plates were blocked by incubating 100 µl PBS/1% bovine serum albumin (BSA) (Sigma, Cat. No. A2153) for 1 hour at 37° C. Following additional washing, the sera were incubated in 50 µl at a 1/50 (in PBS/0.05% TWEEN®/1% BSA buffer (PTB)) to both FCS- and Ca-FCS-coated wells and incubated at 37° C. for 1 hour. Serial dilutions of a standard serum (diluted in PTB) were incubated on Ca-FCS-coated wells. Following washing, bound human IgG or IgA was detected by incubating the wells with 50 µl 1/5000 diluted (in PTB) rabbit anti-human IgG antibody (Dako, Cat. No. A0423) or 1/1000 diluted (in PTB) rabbit anti-human IgA antibody (Dako, Cat. No. A0262) incubated at 37° C. for 1 hour. Following washing, wells were incubated at 37° C. for 1 hour with 50 µl 1/2000 diluted (in PTB) goat anti-rabbit IgG HRP-labeled antibody (Dako, Cat. No. PO448). Following the last washings, HRP enzyme activity was visualized by incubating 50 µl 2,2'Azino-bis-(3-ethylbenzo-thiazole-6-sulfonic acid) diammonium salt (ABTS) and $H_2O_2$, measuring absorbance at 415 nm on a standard ELISA reader.

Detection of Anti-CarP Antibodies by Western Blot

Both FCS and Ca-FCS were loaded onto regular 10% sodium dodecyl sulfate (SDS)-polyacrylamide gels and transferred onto Hybond-C Extra membranes (Amersham, Diegem, Belgium). Blots were then incubated in blocking buffer (3% ELK Milk/PBS/0.05% TWEEN®) 1 hour at RT, following washing with PBS/0.05% TWEEN®. The blots were subsequently incubated with 5 ml serum 1:500 diluted in blocking buffer for 1 hour at RT. After three washes with PBS/0.05% TWEEN®, blots were incubated with 3 ml horseradish peroxidase conjugated rabbit anti-human IgG (DAKO, Heverlee, Belgium) 1:50,000 diluted in blocking buffer for 1 hour at RT. Next, blots were washed and bound antibodies were visualized using enhanced chemiluminescence (ECL; Amersham). Equal protein loading was verified using Coomassie Brilliant Blue (Bio-Rad, Veenendaal, The Netherlands).

Sera and Synovial Fluids

The sera analyzed were from patients participating in the Leiden Early Arthritis Clinic (EAC) cohort. The Leiden EAC is an inception cohort of patients with recent-onset arthritis (symptoms duration <2 years) that was started at the Department of Rheumatology of the Leiden University Medical Center in 1993.[15] All RA patients fulfilled the American College of Rheumatology (formerly the American Rheumatism Association) 1987 revised criteria for the classification of RA[16] within one year of follow-up (EAC cohort). A total of 1007 patients were analyzed, of which 582 were diagnosed as RA and 425 as UA, of which 151 developed RA on follow-up. These patient samples were compared to 280 healthy control samples also derived from the Leiden area. An additional set of paired serum/synovial fluid of RA patients was analyzed. The protocols were approved by the relevant local ethics committee and all participants provided informed consent.

ELISA for the Detection of ACPA

Total IgG anti-CCP2, as a measure of ACPA, was measured in sera collected at baseline by enzyme-linked immunosorbent assay (ELISA) (Immunoscan RA Mark 2; Eurodiagnostica, Arnhem, The Netherlands). Samples with a value above 25 units/ml were considered positive according to the manufacturer's instructions. Individuals with antibodies against CCP2 were considered ACPA-positive.

ELISA for the Detection of Anti-CaFib Antibodies

Non-modified Fib and Ca-Fib were coated at 20 µg/ml in 50 µl (diluted in pH 9.0 PBS) on Nunc Maxisorp plates ON. Following washing in PBS TWEEN®, the plates were blocked by incubating 200 µl pH 9.0 PBS/2% BSA for 2 hours at 4° C. Following additional washing, the wells were incubated with 50 µl serum at a 1/50 dilution in RIA buffer (10 mM Tris pH 7.6; 350 mM NaCl; 1% TritonX; 0.5% Na-deoxycholate; 0.1% SDS) (Sigma) on ice for 3 hours. All subsequent incubations are performed in RIA buffer. As a standard, serial dilutions of a pool of positive sera were used.

Human IgG was detected using HRP-labeled rabbit anti human IgG antibody (DAKO) incubated on ice for 2 hours. Following the last washings, HRP enzyme activity was visualized using ABTS. We transformed the absorbance on Fib and Ca-Fib to aU/mL. We established the cut-off for a positive response as the mean plus 2×the standard deviation of the specific anti-CarP reactivity of the healthy controls.

We analyzed 67 sera of healthy children and 110 sera of patients suffering from juvenile arthritis.

Statistics

Data were analyzed using the Statistical Package for the Social Sciences (SPSS) 17.0 using logistic regression. P-values below 0.05 were considered to be statistically significant.

Example 2

Materials and Methods
Patient and Control Sera

The sera analyzed were from patients participating in the Leiden Early Arthritis Clinic (EAC) cohort. The Leiden EAC is an inception cohort of patients with recent-onset arthritis (symptoms duration <2 years) that was started at the Department of Rheumatology of the Leiden University Medical Center in 1993.[39] All RA patients fulfilled the American College of Rheumatology (formerly the American Rheumatism Association) 1987 revised criteria for the classification of RA[40] within 1 year of follow-up. A total of 571 RA patients were involved in the analyses. Patient samples were compared to 305 healthy control samples also living in the Leiden area. The protocols were approved by the local ethics committee and informed consent was obtained.

Detection of Anti-CarP Antibodies by ELISA

In brief, Non-modified FCS and modified-FCS were coated on NUNC MAXISORP™ plates (Thermo Scientific) over night. Following washings and blocking, the wells were incubated with serum. Bound human IgG or IgA was detected using rabbit anti-human IgG or IgA antibodies (DAKO), followed by HRP-labeled goat anti-rabbit IgG 4bb ABTS.[41] A more detailed description of the protein modifications and ELISA assays based on FCS and Fib, including F(ab)2, is available online (SI-materials and Methods). The cut-off for a positive response was established as the mean plus 2×the standard deviation of the specific anti-CarP reactivity of the healthy controls. The methods for the detection of ACPA and Western blotting are available online (SI-materials and Methods).

ELISA for Fib Peptides

Streptavidin (Invitrogen) was coated at 2 µg/ml in 100 µl on Nunc plates at 4° C. ON. After washing, Fib peptides containing either an arginine, citrulline, homocitrulline or a lysine (FIG. 8, Panel A)[42] were incubated at 10 µg/ml in 100 µl PTB for 1 hour at RT. Next, the reactivity of antibodies reactive to these antigens was detected as described above.

Inhibition Studies

To determine whether anti-CarP antibodies and ACPA are cross-reactive antibodies, we performed inhibition studies in which autoantibody-positive serum samples, positive for both ACPA and anti-CarP antibodies, were pre-incubated with increasing concentrations of either non-modified FCS, Ca-FCS, Ci-FCS or the citrulline- or arginine-containing form of the CCP1 peptide.[43] Following pre-incubation at room temperature (RT), the samples were tested for reactivity against Ca-FCS and Ci-FCS as described above. Serum and F(ab')2 samples positive for both Ci-Fib and Ca-Fib were pre-incubated with Fib, Ci-Fib and Ca-Fib at 4° C. ON and subsequently analyzed on the Fib ELISA (SI-materials and Methods).

Radiological Progression

In the EAC cohort, radiographs of the hands and feet, which had been obtained in a longitudinal fashion, were scored according to the Sharp/van der Heijde method.[44] Scoring and analysis have been described in detail before.[21] Data are analyzed directly, or using repeated measurement analysis, as to optimally make use of the longitudinal data obtained for each patient.[21] More detailed information is available online (SI-materials and Methods).

Generation of Antigens

Because it was not known whether antibodies against carbamylated proteins would be present in sera of RA patients, or which proteins they would recognize, a study of a diverse set of carbamylated proteins was commenced in order to maximize the chances of detecting as many of the anti-CarP reactivities as possible. For this purpose, fetal calf serum (FCS) (Bodinco) that was carbamylated, citrullinated or left untreated was used. For generating carbamylated FCS (Ca-FCS), FCS was diluted in $H_2O$ to 4 mg/ml and potassium cyanate (Sigma) was added to a concentration of 1 M. Following incubation at 37° C. for 12 hours, the sample was extensively dialyzed against $H_2O$. Carbamylated fibrinogen (Ca-Fib) was generated by incubating 5 mg/ml fibrinogen (Fib) with 0.5 M potassium cyanate at 4° C. for three days, followed by extensive dialysis against PBS. Citrullinated FCS (Ci-FCS) and citrullinated fibrinogen (Ci-Fib) was generated by incubation of 10 mg FCS or Fib in a volume of 1 mL containing 0.1 M Tris-HCl pH 7.6, 0.015 M $CaCl_2$ and 40 U PAD4 (Sigma) for 24 hours at 37° C. The presence of citrulline and homocitrulline residues was confirmed using mass-spectrometry analysis. For Fib, extensive citrullination and complete carbamylation was observed in the protein segments analyzed.

Detection of Anti-CarP Antibodies by ELISA

Figure 7:
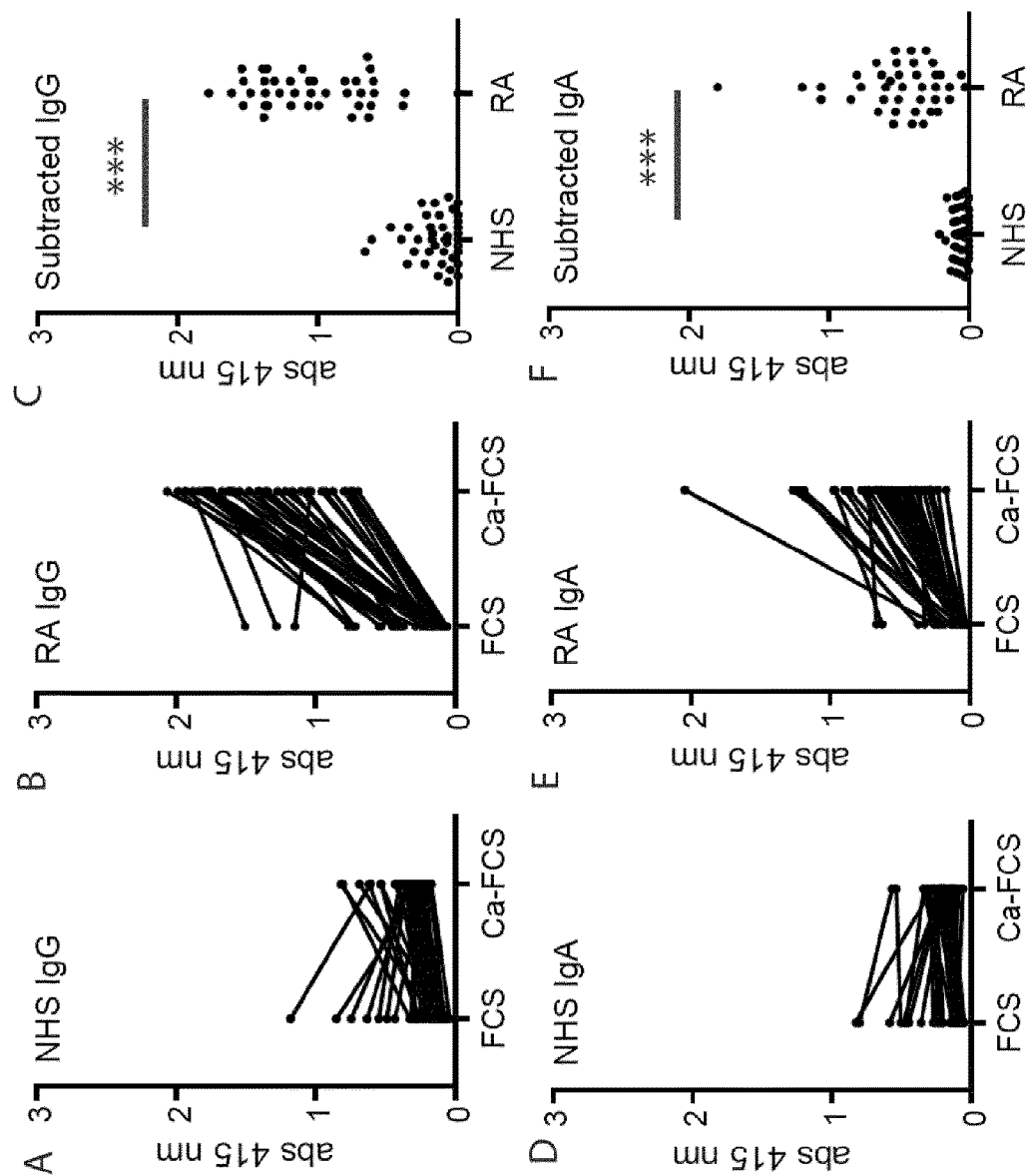
FIG. 7: Antibodies against carbamylated proteins are present in sera of RA patients. The reactivity of IgG (Panels A and B) and IgA (Panels D and E) from sera of healthy controls (NHS) or RA patients (RA) to wells coated with non-modified FCS (FCS) or carbamylated FCS (Ca-FCS) is depicted. Data expressed as absorbance at 415 nm. In Panels C and F, absorbance units of FCS were subtracted from the absorbance units of Ca-FCS, representing the specific anti-carbamylated protein response.

Non-modified FCS and modified-FCS were coated at 10 µg/ml in 50 µl (diluted in pH 9.6 0.1 M carbonate-bicarbonate buffer) (CB) on NUNC MAXISORP™ plates (Thermo Scientific) overnight (ON). Following washing in PBS containing 0.05% TWEEN.RTM. (Sigma) (PT), the plates were blocked by incubating 100 µl PBS/1% bovine serum albumin (BSA) (Sigma) for 6 hours at 4° C. Following additional washing, the wells were incubated with 50 µl serum at a 1/50 dilution in PBS/0.05% TWEEN.RTM./1% BSA buffer (PTB) on ice overnight. All subsequent incubations are performed in PTB. As a standard, serial dilutions of a pool of positive sera were used. Human IgG or IgA was detected using rabbit anti-human IgG antibody (DAKO) or rabbit anti-human IgA antibody (Dako) incubated on ice for 3.5 hours. Following washing, wells were incubated on ice for 3.5 hours with HRP-labeled goat anti-rabbit IgG antibody (Dako). Following the last washings, HRP enzyme activity was visualized using ABTS as described before.[22] Sera of healthy subjects (n=305) were used as controls. The absorbance on both Ca-FCS and FCS was transformed to aU/mL and subtracted the background signal (aU/mL) of FCS from the signal (aU/mL) of Ca-FCS as to analyze the specific anti-CarP reactivity (FIG. 7). The cut-off was established for a positive response as the mean plus 2×the standard deviation of the specific anti-CarP reactivity of the healthy controls.

ELISA for Fibrinogen

Non-modified Fib Ci-Fib and Ca-Fib were coated at 20 µg/ml in 50 µl (diluted in pH 9.0 PBS) on NUNC MAXISORP™ plates ON. Following washing in PT, the plates were blocked by incubating 200 μl pH 9.0 PBS/2% BSA for 2 hours at 4° C. Following additional washing, the wells were incubated with 50 μl serum at a 1/50 dilution in RIA buffer (10 mM Tris pH 7.6; 350 mM NaCl; 1% TritonX; 0.5% Na-deoxycholate; 0.1% SDS) (Sigma) on ice for 3 hours. All subsequent incubations are performed in RIA buffer. As a standard, serial dilutions of a pool of positive sera were used. Human IgG was detected using HRP-labeled rabbit anti-human IgG antibody (DAKO) incubated on ice for 2 hours. Following the last washings, HRP enzyme activity was visualized using ABTS. Sera of 214 RA patients and 54 healthy subjects as controls was analyzed. The absorbance on Fib Ci-Fib and Ca-Fib was transformed to aU/mL. The cut-off was established for a positive response as the mean plus 2×the standard deviation of the specific anti-CarP reactivity of the healthy controls. These assays were repeated three times showing the same data.

F(ab')2 Preparation

Total IgG from two anti-CarP-positive and two control sera were isolated via a HiTrap™ protein A HP column (GE Healthcare) following the protocol for the column provided by the manufacturer. F(ab')2 fragments were generated from purified IgG samples using a F(ab')2 Preparation Kit (Thermo Scientific) following the protocol provided by the manufacturer. The molecular nature of the intact IgG and the F(ab')2 was verified using Coomassie-stained SDS page gels. These F(ab')2 were used in ELISA as described above, now using either HRP-labeled rabbit anti-human IgG, IgA, IgM kappa, lamda antibody (anti-light chain) (Dako) or HRP-labeled rabbit anti-human IgG (Dako).

Detection of ACPA by ELISA

ACPA were measured by the CCP2 ELISA (Immunoscan RA Mark 2; Eurodiagnostica, Arnhem, The Netherlands). Samples with a value above 25 units/ml were considered positive according to the manufacturer's instructions. A small percentage of ACPA-positive RA patients may be outside the anti-CCP2 reactivity and, therefore, both terms will be used to explicitly indicate what has been used in our analyses.

ACPA reactivity toward Ci-FCS was detected using ELISA plates that were coated with Ci-FCS (50 μl/well 10 .mu.g/ml) diluted with CB in the NUNC MAXISORP™ plates ON at 4° C. The plates were washed in PT followed by blocking with 100 μl PBS/1% BSA solution at 37° C. for 1 hour. Following washing, sera were incubated at a 1/50 dilution in 50 μl PTB and incubated at 37° C. for 1 hour. After washing, human IgA and IgG were detected as described above.

Detection of Anti-CarP Antibodies by Western Blot

FCS, Ca-FCS and Ci-FCS were loaded onto 10% sodium dodecyl sulfate (SDS)-polyacrylamide gels and transferred onto Hybond-C Extra membranes (Amersham). Blots were incubated in blocking buffer (3% ELK Milk/PBS/0.05% TWEEN®) for 1 hour at RT, following washing with PT. The blots were subsequently incubated with 2.5 ml 1:500 diluted serum in blocking buffer for 1.5 hours at RT. The sera were either ACPA-positive anti-CarP negative or ACPA-negative anti-CarP positive as determined by ELISA. After three washes with PT, blots were incubated with 5 mL HRP-labeled rabbit anti-human IgG diluted in blocking buffer for 1 hour at RT. Next, blots were washed and bound antibodies were visualized using enhanced chemiluminescence (Amersham).

Statistics of Radiological Progression

Association between anti-CarP antibodies positivity and radiographic progression was analyzed using the Statistical Package for the Social Sciences (SPSS) 17.0 as described before. P-values below 0.05 were considered statistically significant. A multivariate normal regression analysis for longitudinal data was used with radiological score as response variable. This method analyses repeated measurements at once and takes advantage of the correlation between these measurements, which results in a more precise standard error. Radiological scores were log-transformed to obtain a normal distribution. The rate of joint destruction over time was tested by an interaction of time with anti-CarP. The effect of time was assumed to be linear in the interaction term. The effect of time was entered as factor in the model as well, allowing a mean response profile over time. Age, gender and inclusion period as proxy for treatment were included as correction variables in all analyses. In a separate analysis, the effect of anti-CarP antibodies was corrected for the effect of anti-CCP and RF.

Example 1

Results

Detection of Anti-CarP Antibodies

Figure 1B:
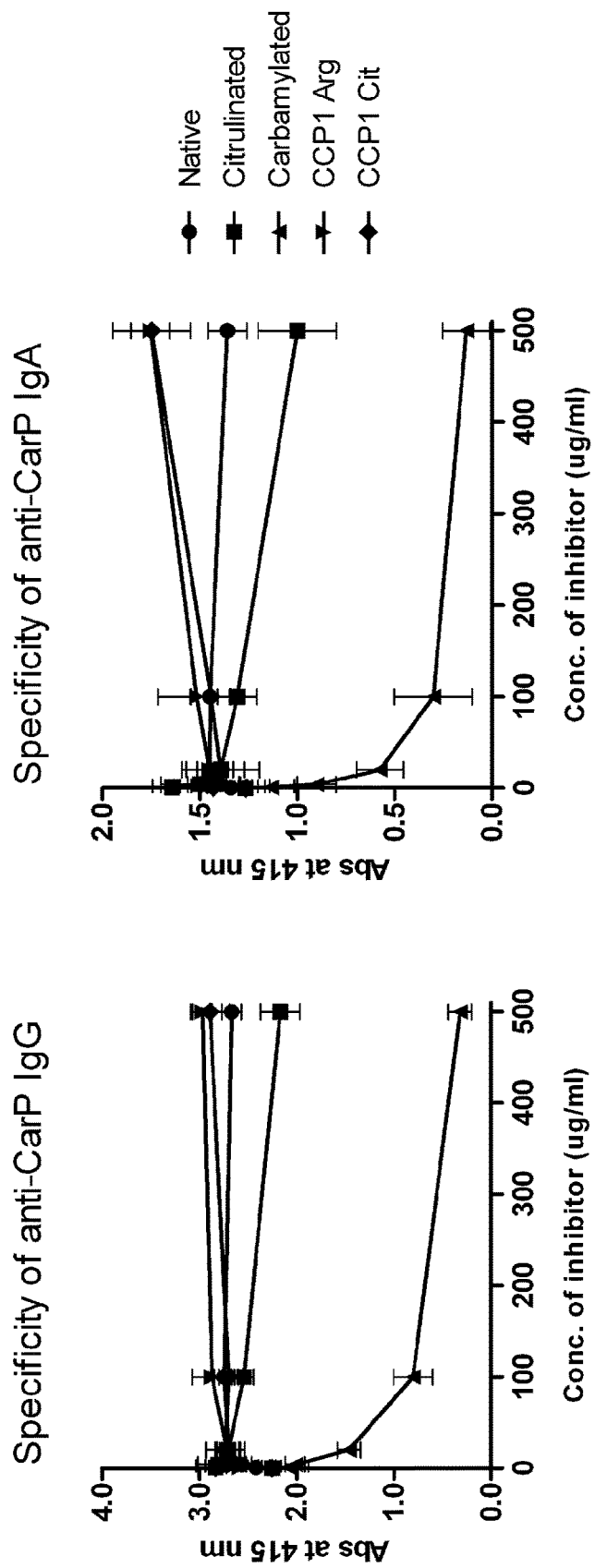

A novel ELISA was generated to detect anti-CarP antibodies from serum and synovial fluid using plates coated with, in vitro-generated, carbamylated FCS. A standard was generated from a pool of positive sera showing a dose-dependent binding of both IgG and IgA to Carbamylated FCS (Ca-FCS) and no binding to the native FCS (FIG. 1A). Since homocitrulline and citrulline are very similar residues but differ from each other by one atom, excluding the possibility that the anti-CarP antibodies were actually ACPA was desired. As a first test to exclude this, inhibition studies were performed that show that anti-CarP antibody binding to Ca-FCS can only be inhibited by Ca-FCS itself and not by citrullinated FCS (Ci-FCS), native FCS or by peptides used to detect ACPA (FIG. 1B), indicating that anti-CarP is truly a different reactivity. In addition, binding of ACPA to CCP2 plates was not inhibited by addition of Ca-FCS (data not shown).

Figure 1C:
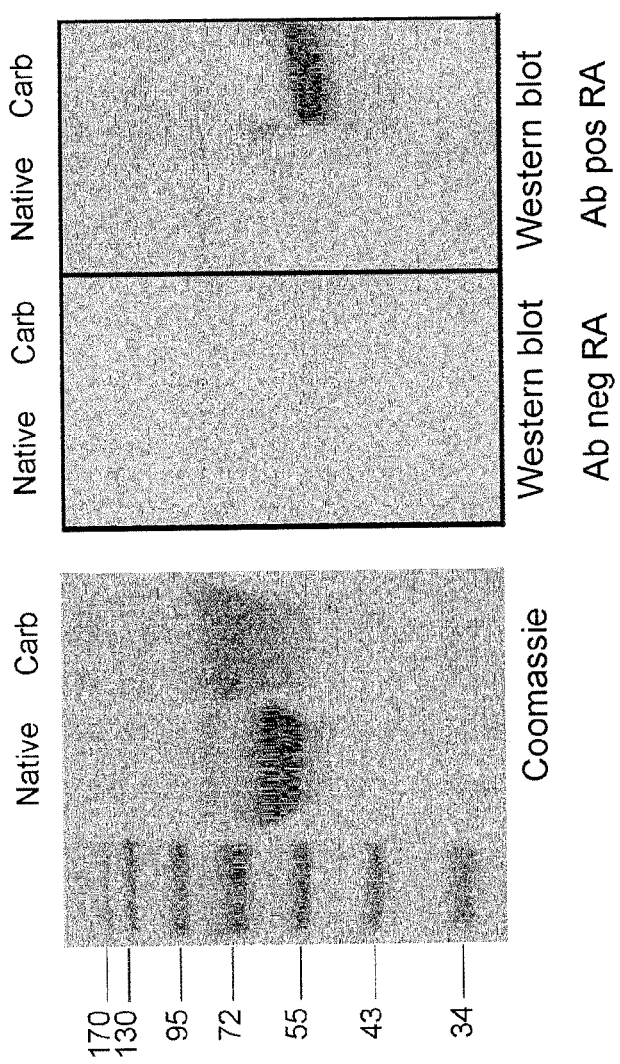

Since these methods rely on ELISA, confirmation of those findings using Western blotting was desired. FCS and Ca-FCS was run on non-reducing gels, and following Western blotting, stained the blots using sera of patients that were positive or negative for anti-CarP antibodies as detected by ELISA. Serum of anti-CarP antibody-positive patients tested positive on lanes loaded with Ca-FCS, while no reactivity was seen in lanes loaded with FCS (FIG. 1C). Sera from anti-CarP antibody-negative patients did not show such staining. Using Coomassie staining on loaded gels, it was confirmed that the FCS-loaded lanes did contain similar protein amounts. Collectively, these data indicate that a novel assay has been generated that can specifically detect anti-CarP antibodies, both IgG and IgA.

Anti-CarP Antibodies are Present in RA

Figure 2:
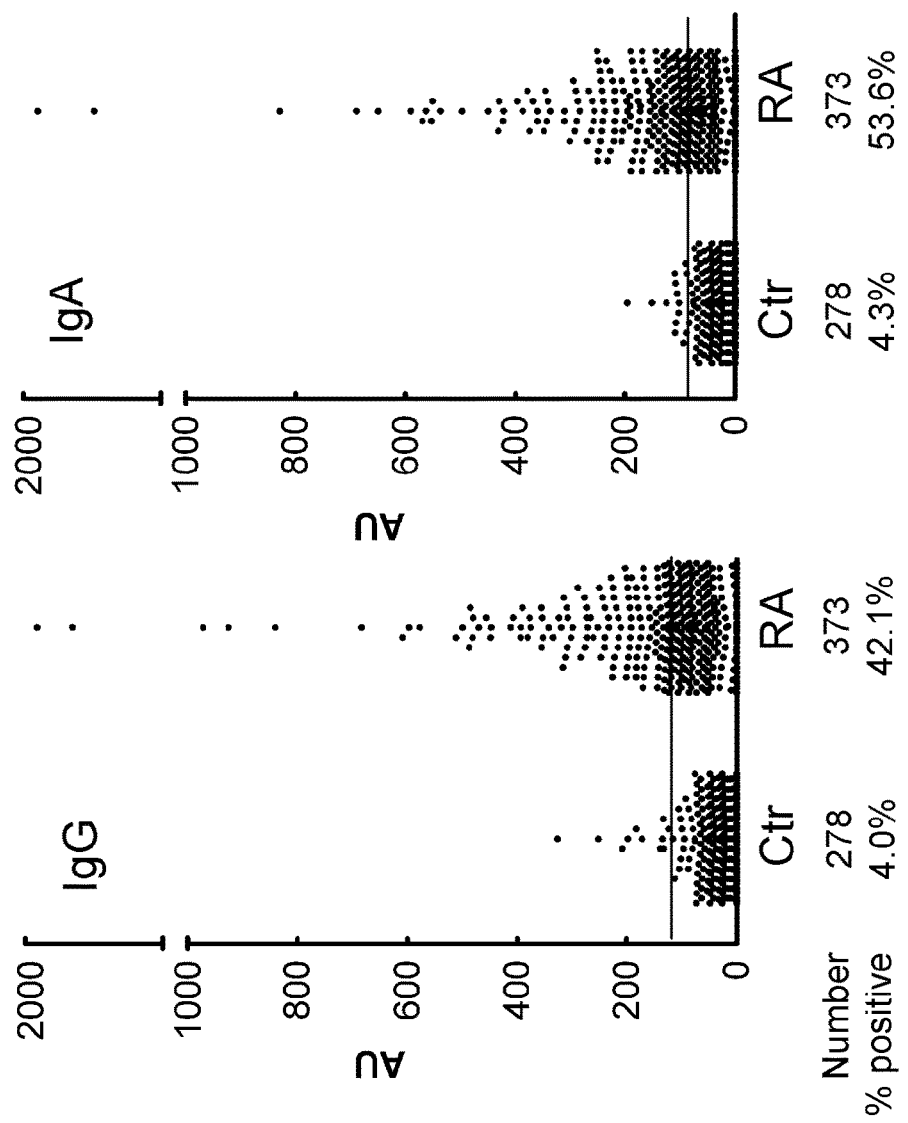
FIG. 2: Anti-CarP IgG and IgA antibodies are present in RA sera. ELISA was performed for the detection of anti-CarP IgG and IgA in sets of sera of healthy controls and RA patients. A cut-off was established using the mean plus two times the standard deviation of the healthy controls. Shown is the titer expressed as arbitrary units per ml following calculation based on the standard curve. Below the graph, both the number of samples tested and the percentage positivity is indicated.

From the Leiden Early Arthritis Clinic (EAC), patients suffering from UA or RA have been used according to the 1987 inclusion criteria. In addition, healthy controls were also used from the Leiden region. The presence of anti-CarP antibodies in patients and controls was measured simultaneously. OD values were calculated to arbitrary units per mL using a standard. Healthy persons were used to calculate the cut-off for positivity as defined by the mean plus 2×the standard deviation of the healthy controls. Samples were considered to be positive when they had a titer higher than the cut-off and an absorbance that was at least 0.1 units higher on Ca-FCS as compared to FCS.[17] Using this approach, it was established that 42% of the RA patients were positive for IgG anti-CarP antibodies, whereas 54% of sera from RA patients tested were positive for IgA anti-CarP-antibodies (FIG. 2). Analysis of paired serum/synovial fluid samples revealed that anti-CarP IgG and IgA can also be found in synovial fluid of patients that are positive for these autoantibodies in serum (data not shown).

Anti-CarP antibodies are present in serum and synovial fluid in a substantial proportion of RA patients.

Anti-CarP Antibodies are Independent from ACPA

Figure 3:
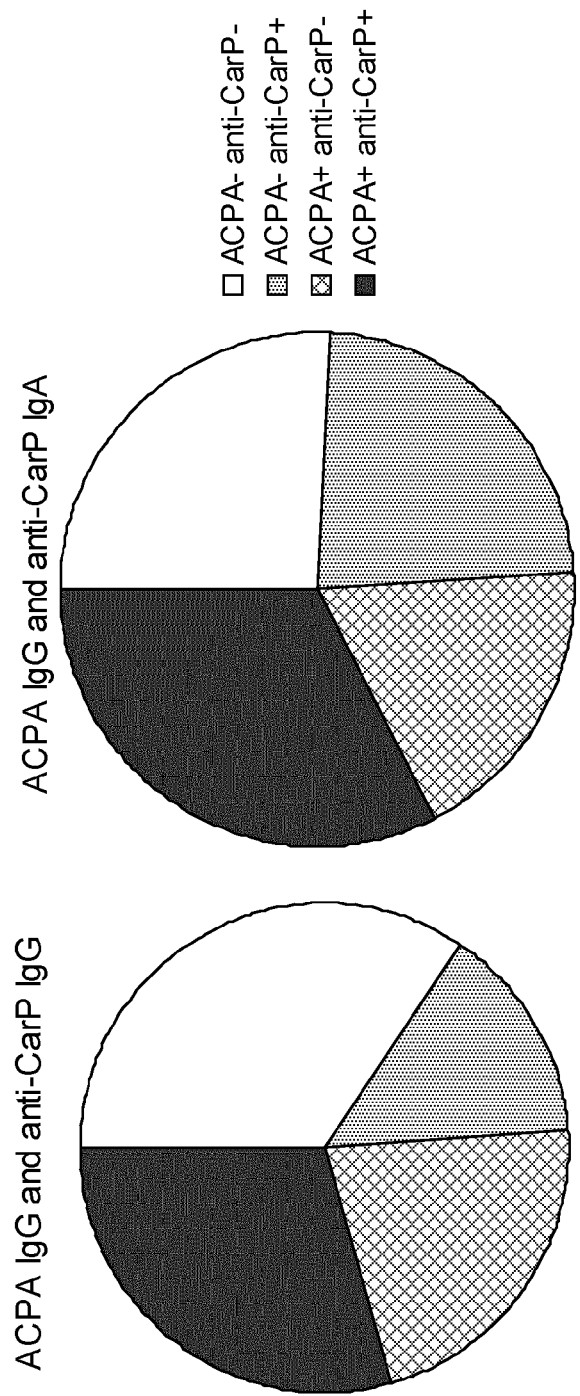
FIG. 3: Anti-CarP antibodies and ACPA are two separate autoantibody systems. Pie charts showing the percentages of RA patients positive and negative for ACPA and/or anti-CarP antibodies.

Next, it was analyzed as to whether the anti-CarP antibodies occur independently of ACPA. To this end, the relationship between ACPA and anti-CarP antibodies in a set of 373 RA patients was analyzed. The data show that 14% and 23% of the RA patients did not display ACPA but did harbor anti-CarP IgG and IgA, respectively. Likewise, 22% and 19% of the RA patients were positive for ACPA but negative for anti-CarP IgG and IgA, respectively (FIG. 3). Zooming in on the ACPA-negative individuals, it was observed that around 50% of all ACPA-negative RA patients tested positively for anti-CarP antibodies. Thus, anti-CarP antibodies occur independently from ACPA.

Anti-CarP Antibodies are Predictive for Development of RA

Figure 4:
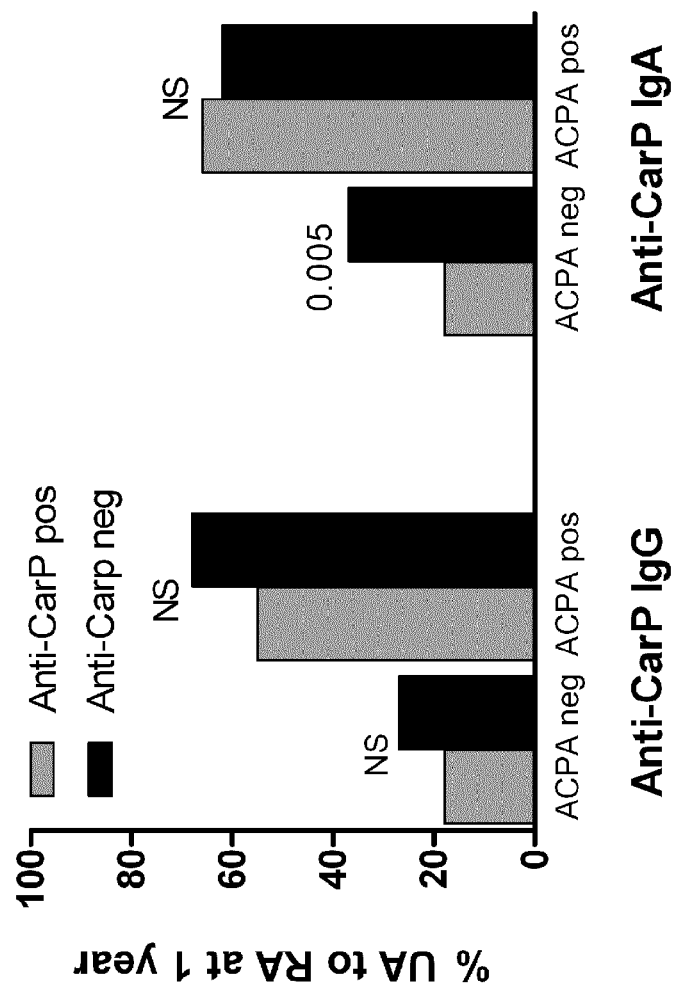
FIG. 4: Anti-CarP IgA antibodies are associated with the conversion of undifferentiated arthritis (UA) to RA. Sera of patients that presented with UA at baseline were measured for anti-CarP IgG and IgA antibodies and analyzed for their conversion toward RA at the one-year follow-up. Data shown are also split up on the basis of ACPA positivity. IgA anti-CarP antibodies associate strongly with development of RA from a UA population.

Patients presenting themselves at baseline with a diagnosis of undifferentiated arthritis can go into remission, develop another form of arthritis or can develop RA. Clinically, it would be relevant to be able to discriminate between the patients in need for treatment and the patients that will remit spontaneously. Therefore, 425 patients that had UA at baseline for the presence of anti-CarP antibodies and the development of RA (n=151) were analyzed. It was observed that positivity for IgG anti-CarP antibodies did not associate with RA development according to the 1987 criteria in a statistically significant manner (p=0.11). In contrast, IgA anti-CarP antibodies were strongly associated with future development of RA in the UA group as a whole (p=0.002) (FIG. 4). This effect was especially prominent in the ACPA-negative individuals (FIG. 4).

Measuring anti-CarP antibodies in patients suffering from undifferentiated arthritis is useful to identify persons at risk to develop RA.

Anti-CarP Antibodies are Associated with More Severe Radiological Damage

Figure 5:
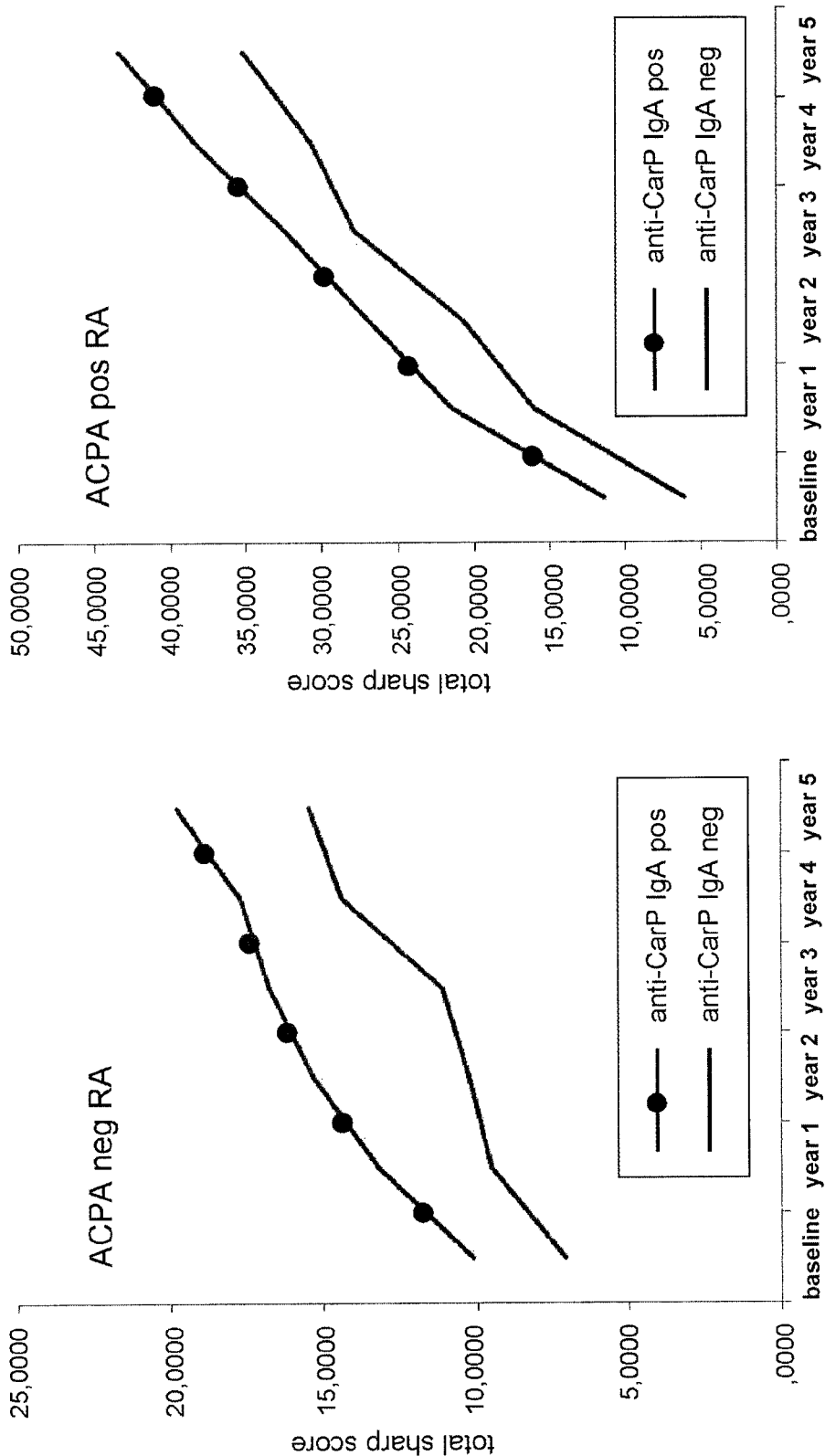
FIG. 5: Anti-CarP IgA antibodies are associated with more severe radiological progression in RA. The extent and rate of joint destruction were analyzed in the RA patients split up on the basis of positivity for ACPA and anti-CarP antibodies. Positivity for anti-CarP IgA antibodies is associated with a more severe radiological damage in both ACPA-negative and ACPA-positive RA patients.

Finally, analysis was performed to ascertain whether RA patients that are positive at baseline for anti-CarP antibodies would have a different clinical course of their disease. Therefore, comparisons were made as to the extent of joint damage over time. Also in this analysis, positivity for IgG anti-CarP antibodies did not associate with radiological damage in a statistically significant manner (p=0.43). However, IgA anti-CarP antibodies are strongly associated with more severe damage to the joints (p=0.002) (FIG. 5), an effect that was independent from Rheumatoid Factor (RF) or ACPA. Together, these data indicate that anti-CarP antibodies are associated with a more severe disease course, independent of the presence of RA and or ACPA.

Discussion

A novel family of autoantibodies that recognize carbamylated proteins (anti-CarP) is described. These anti-CarP antibodies can be detected in both the IgG and IgA isotypes. Both inhibition studies and cohort studies show that anti-CarP antibodies are different from ACPA. Interestingly, positivity for anti-CarP, especially IgA, has clinical implications as individuals positive for anti-CarP IgA have an increased risk to progress from UA to RA and anti-CarP IgA-positive RA patients have a worse outcome compared to anti-CarP IgA-negative RA patients.

A complex protein mix was used as an initial source of carbamylated protein antigens and, therefore, generated Ca-FCS. It was observed that antibodies exist that are specifically directed against the carbamylated form of FCS, which do not bind to native or citrullinated FCS in both ELISA and Western blot systems. These antibodies are of both the IgG and IgA isotypes, indicating that they are derived from class-switched B cells, a process that would require T cell help. Indeed, data indicate that homocitrulline directed T cells can be induced by immunization with carbamylated model antigens.[11]

It is shown herein that detection of these antibodies in early arthritis can predict the future development of RA and predict a more severe disease course. Since it has been shown that early aggressive treatment is beneficial,[18, 19] the invention provides methods for arthritis treatment of individuals suffering from, or at risk of suffering from, arthritis, the method comprising an arthritis diagnosis of the individual wherein the diagnosis comprises a method for determining an anti-CarP antibody in a sample comprising a body fluid of the individual. Preferably, the sample was determined to contain an anti-Carp antibody. A more stringent treatment of the anti-CarP-positive individual is beneficial to the patient.

In conclusion, next to the autoantibody system that recognizes citrullinated proteins (ACPA), an autoantibody system is also present against carbamylated proteins (anti-CarP). Detection of such antibodies is useful since its presence is, independently of ACPA, associated with development of UA to RA and is associated with a more severe disease course.

Example 2

Results

Anti-CarP Antibodies and ACPA are Different Antibody Families

Figure 6A:
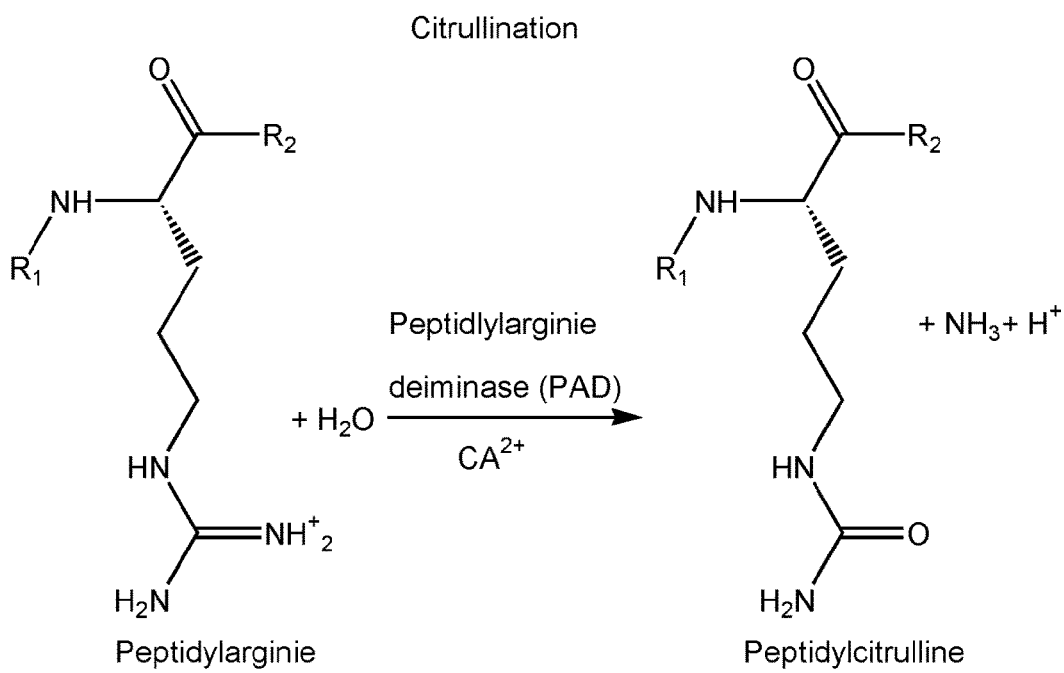
FIGS. 6A and 6B: Illustration of citrullination and carbamylation. Citrullination and carbamylation occur on different amino acids via different mechanisms, but yield similar end-products.
Figure 6B:
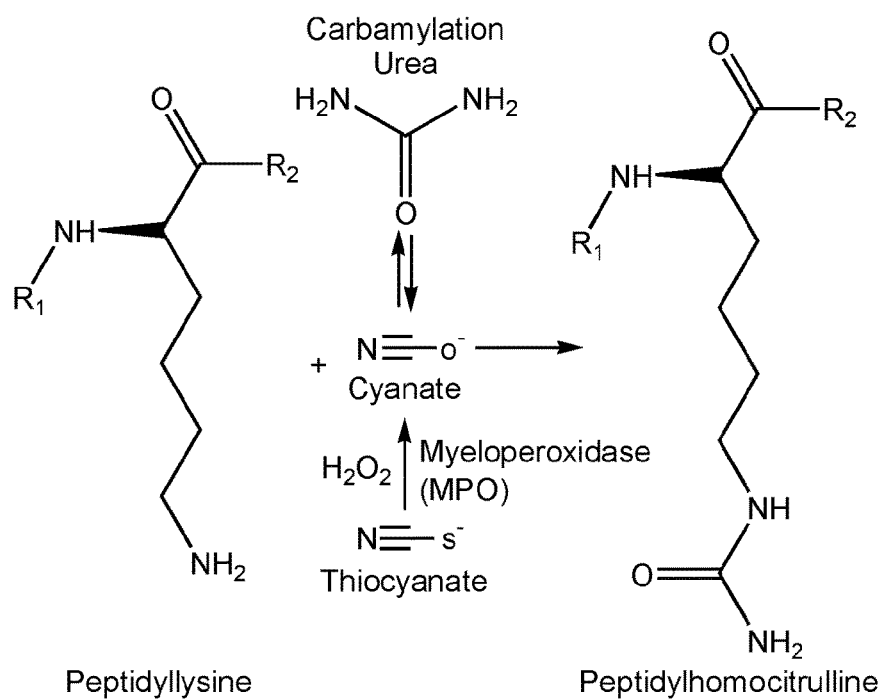
Figure 8:
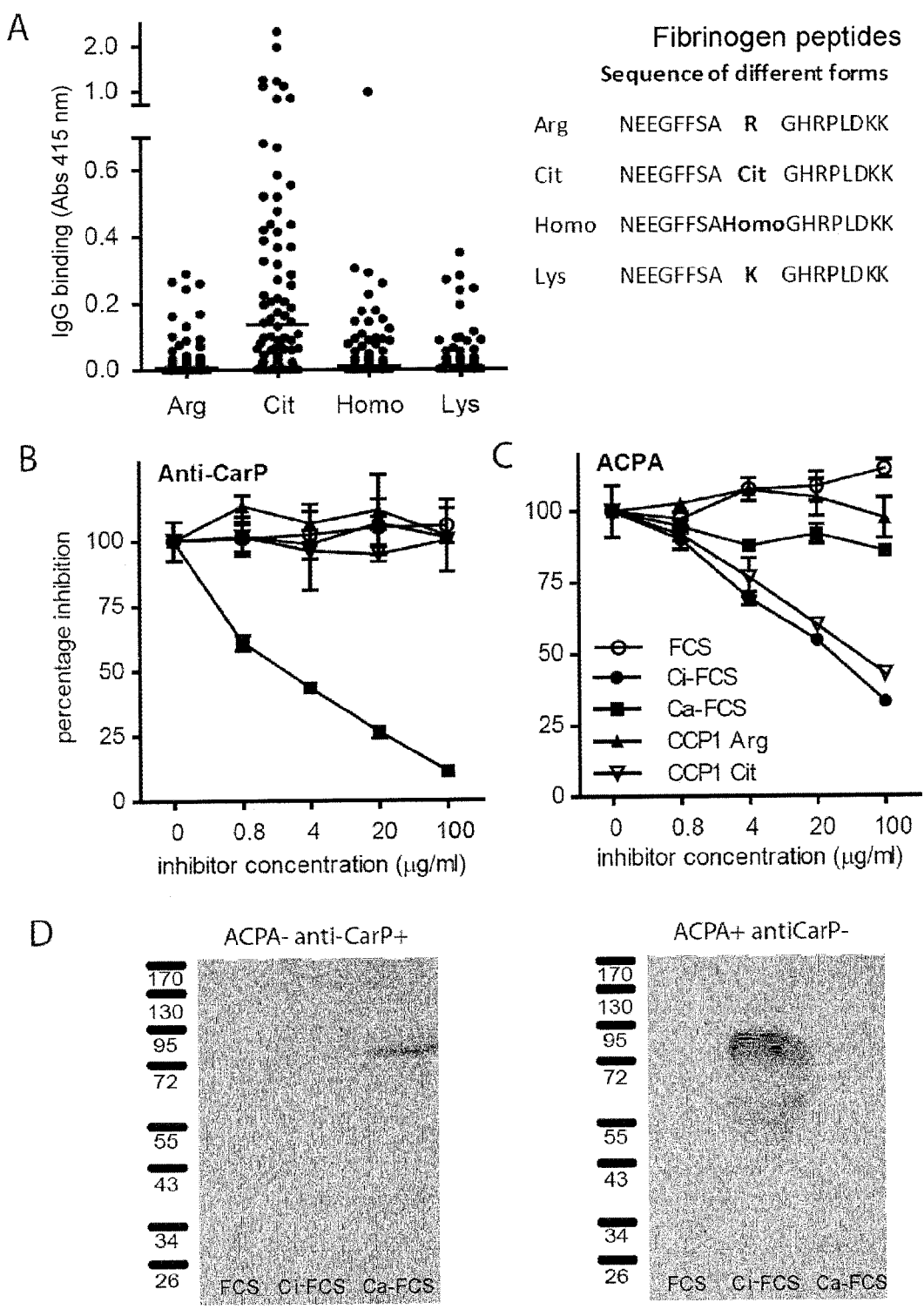
FIG. 8: Anti-CarP antibodies and ACPA are two separate autoantibody systems. Panel A depicts IgG reactivity of 76 sera from RA patients toward several forms of a Fib peptide. Panels B and C depict binding to Ca-FCS or Ci-FCS was inhibited using pre-incubations with fluid-phase inhibitors. Panel D shows that FCS, Ca-FCS and Ci-FCS were separated by SDS-page gels and blotted. The presence of antibodies reactive to proteins on the blots was analyzed by incubating these blots with either anti-CarP-positive ACPA-negative and anti-CarP-negative ACPA-positive sera.
Figure 9:
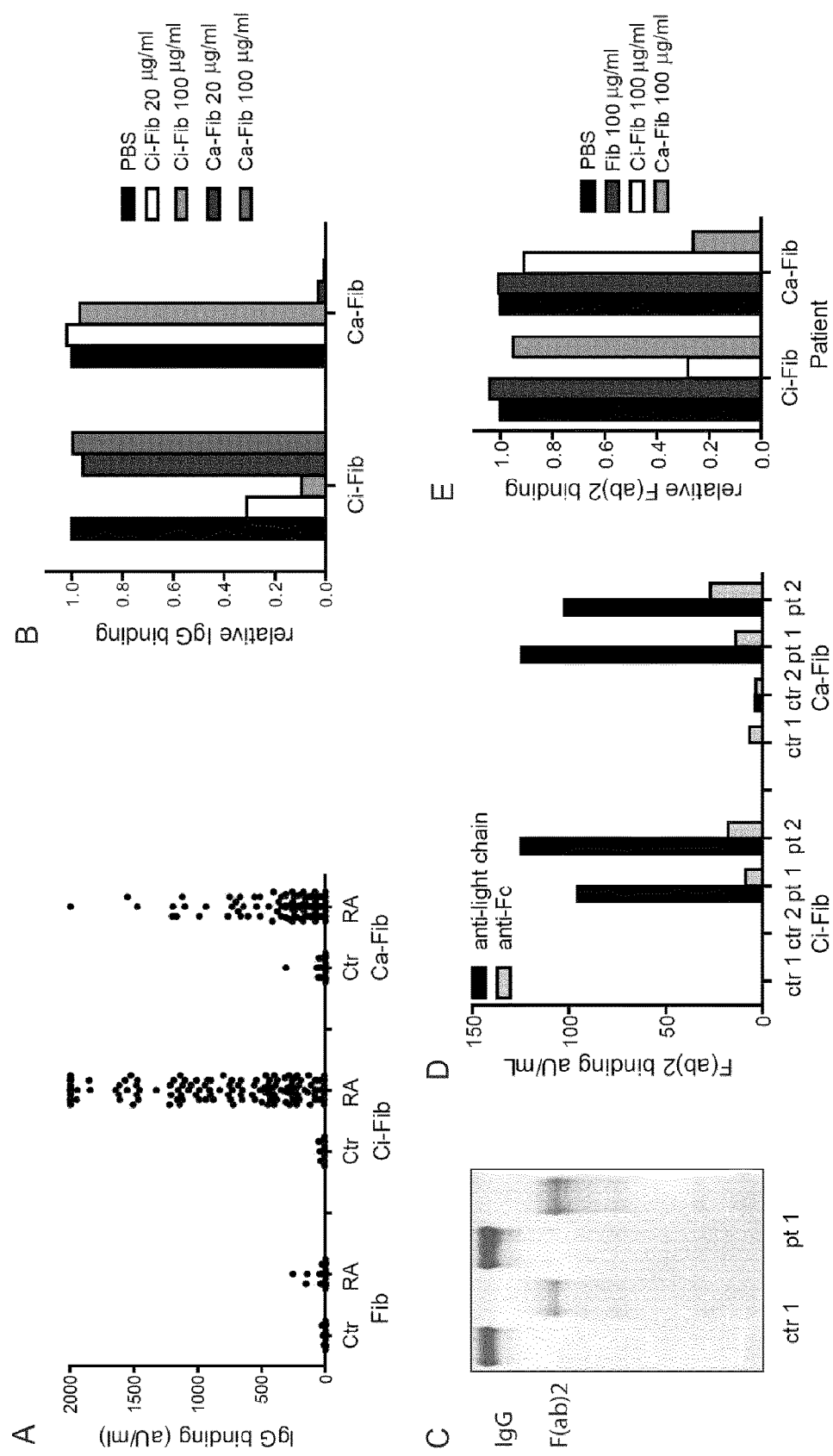
FIG. 9: Anti-CarP antibodies bind to Ca-Fib via variable domains. Panel A: IgG reactivity against Fib, Ci-Fib and Ca-Fib of 54 healthy controls and 214 RA patients was analyzed by ELISA. Panel B: Specificity of anti-Ca-Fib reactivity was confirmed using inhibition studies. One sample is shown, where data are expressed relative to inhibition with PBS. Panel C: The molecular nature of purified IgG and F(ab')2 was confirmed by Coomassie-stained SDS page gel. Panel D: F(ab')2 fragments were generated from purified IgG of two anti-CarP-positive patients and two negative controls. Only F(ab')2 from patients reacted with Ci-Fib and Ca-Fib. Panel E: Inhibition experiments also confirm that F(ab')2 are not necessarily cross-reactive between Ci-Fib and Ca-Fib.

To detect antibodies against carbamylated proteins (anti-CarP antibodies), an ELISA was developed using carbamylated FCS (Ca-FCS) and non-modified FCS as antigens. Analyzing sera of 40 RA patients and 40 controls, it was observed that sera of RA patients reacted with Ca-FCS as compared to sera obtained from healthy subjects with both IgG (FIG. 7, Panels A and B) and IgA (FIG. 7, Panels C and D) reactivity. The enhanced reactivity of RA sera to Ca-FCS is further emphasized after subtraction of the reactivity against unmodified FCS (FIG. 7, Panels C and E). Since citrulline and homocitrulline are two rather similar amino acids (FIG. 6), it was next determined whether ACPA also recognizes homocitrulline when located at the same position as citrulline in a peptide. For this purpose, ELISAs were performed using a citrullinated Fib peptide known to be recognized by ACPA.[20] Within this peptide backbone, a citrulline, an arginine, a homocitrulline or a lysine residue was introduced for further analysis. Analyzing a set of 76 RA sera, it was observed that ACPA only recognized the citrullinated peptide, but not the arginine-containing or the homocitrulline-containing peptide (FIG. 8, Panel A). These data indicate that ACPA can discriminate between citrulline and homocitrulline present within the same peptide backbone. Next, analysis was performed as to whether there is cross-reactivity between anti-CarP antibodies and ACPA for binding to post-translationally modified proteins. Therefore, inhibition studies were performed using sera that were reactive to both citrullinated and carbamylated antigens. The binding of anti-CarP antibodies to Ca-FCS-coated plates following pre-incubation with Ca-FCS, citrullinated FCS (Ci-FCS), native FCS or by citrullinated peptides used to detect ACPA (CCP1) was analyzed. Following pre-incubation, it was observed that anti-CarP antibody binding to Ca-FCS can only be inhibited by Ca-FCS but not by citrullinated FCS (Ci-FCS), native FCS or by peptides used to detect ACPA (FIG. 8, Panel B). The reverse inhibition experiment was performed where the binding of ACPA to plates coated with Ci-FCS following the same pre-incubation procedure was analyzed. It was observed that ACPA binding to Ci-FCS could only be inhibited by Ci-FCS and the citrullinated peptide but not by Ca-FCS, non-modified FCS, or the arginine form of the peptide (FIG. 8, Panel C). Together, these data indicate that anti-CarP antibodies and ACPA are not (or only limited) cross-reactive and specifically directed against homocitrulline, respectively, citrulline-containing antigens. Since all observations described above were made using ELISA, confirmation of the findings using a different technique was desirable. For this reason, a Western blot analysis was performed using FCS, Ca-FCS and Ci-FCS on reduced gels, followed by Western blotting. The different blots were incubated with sera of individuals that were either anti-CarP positive and ACPA negative or anti-CarP negative and ACPA positive. A positive staining of the anti-CarP-positive sample was observed only on Ca-FCS but not on Ci-FCS or FCS (FIG. 8, Panel D). In contrast, the anti-CarP negative, ACPA-positive sample reacted to Ci-FCS, but not to Ca-FCS and FCS (FIG. 8, Panel D). To confirm the presence of anti-CarP antibodies, these experiments were repeated using a more defined protein, human Fib, as target antigen. Fib was citrullinated by PAD (Ci-Fib) or carbamylated by cyanate (Ca-Fib). The non-modified form (Fib), Ci-Fib and Ca-Fib were used as antigens in ELISA. Similar to the observations for FCS, significant binding of antibodies to the Ci-Fib and the Ca-Fib but not to the Fib-coated wells was observed (FIG. 9, Panel A). This was largely restricted to the RA sera and not the controls ($p=<0.0001$). To analyze cross-reactivity, inhibition studies were performed as described above. ELISA analyses confirmed that ACPA and anti-CarP antibodies are largely non-cross-reactive. To ensure that reactivity toward carbamylated proteins is mediated by the antigen-binding-part of the antibodies, F(ab')2 was generated. As expected, F(ab')2, generated from anti-CarP IgG-positive samples but not from negative samples, display anti-CarP reactivity (FIG. 9, Panels C and D). As observed using intact antibodies, F(ab')2 reactivity toward Ca-Fib could be inhibited specifically by Ca-Fib, whereas F(ab')2 reactivity toward Ci-Fib could only be inhibited specifically by Ci-Fib (FIG. 9, Panel E).

Collectively, these data indicate that anti-CarP antibodies and ACPA recognize different antigens, one recognizing citrullinated proteins (ACPA) and the other carbamylated proteins (anti-CarP). Likewise, these data indicate that antigen recognition is most likely mediated via the variable domains present in the F(ab')2 fragments.

Anti-CarP Antibodies are Present in RA

Figure 10:
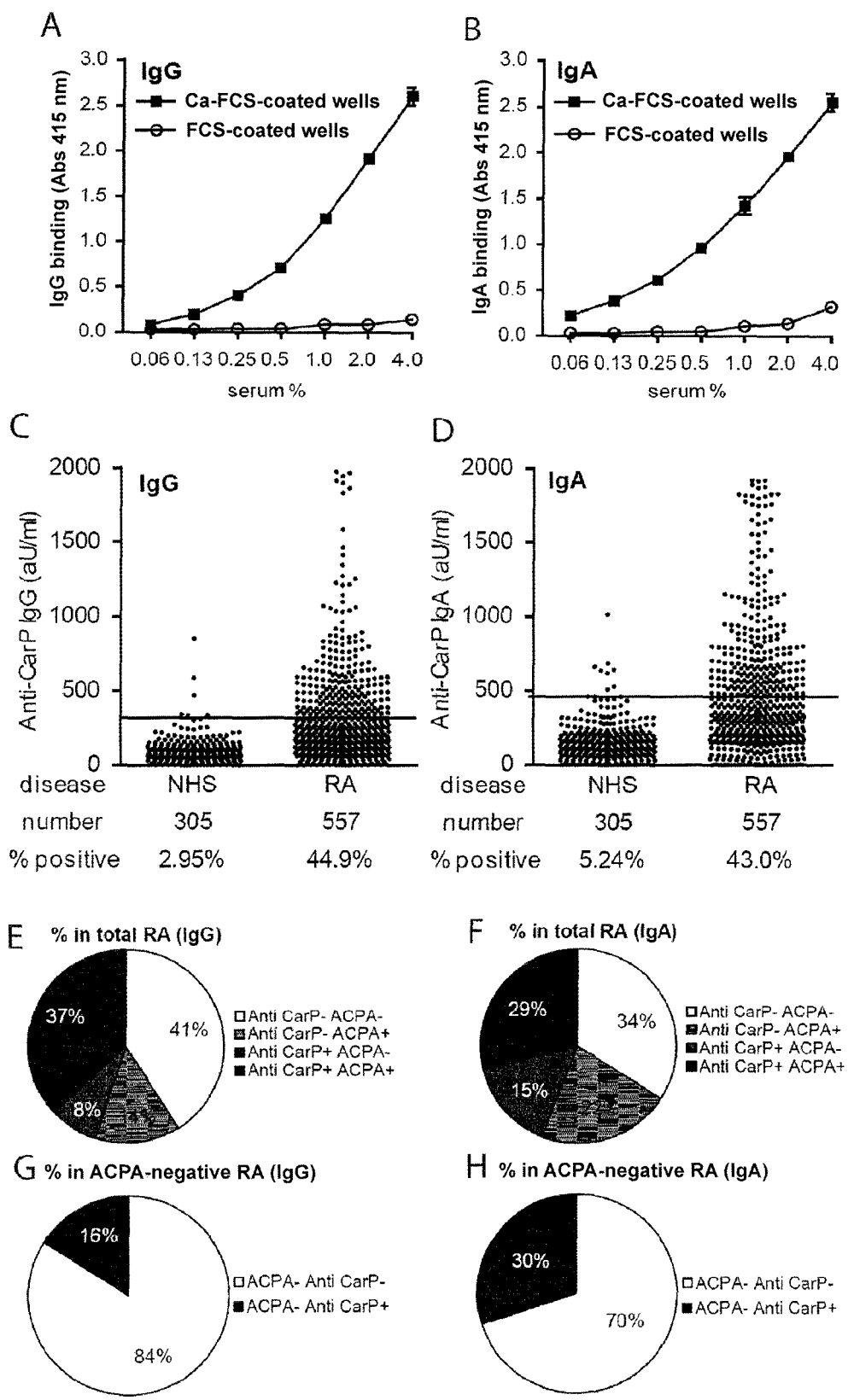
FIG. 10: Anti-CarP IgG and IgA antibodies are present in RA sera. Panels A and B: Dose response curves of the anti-CarP antibody-positive standard (IgG and IgA) on Ca-FCS and FCS in ELISA. Panels C and D: ELISA was performed for the detection of anti-CarP IgG and IgA in sera of healthy controls (NHS) and RA patients. A cut-off was established using the mean plus two times the standard deviation of the healthy controls as described in the methods. Reactivity is depicted as arbitrary units per mL. The number of samples tested and the % positivity is indicated below the graph. Panels E and F: Pie charts showing the % of RA patients positive and negative for anti-CCP2 and/or anti-CarP antibodies. Panels G and H: Pie charts showing the % of anti-CarP IgG- or IgA-positive patients negative for anti-CCP2.

Following the identification of anti-CarP antibodies as an autoantibody family separate from ACPA, quantifying the presence of these anti-CarP antibodies in a large population of RA patients and controls was desired. For this reason, first, a standard was generated comprising a pool of anti-CarP antibody-positive sera. This standard displayed a specific, dose-dependent, binding of both IgG and IgA to carbamylated FCS (Ca-FCS) but no binding to unmodified FCS (FIG. 10, Panels A and B). For this analysis, the FCS-based assay was again used in an attempt to capture as many anti-CarP reactivities as possible. A cut-off for positivity was established using sera of 305 healthy individuals as described in the methods section. Using this approach, it was observed that 45% of the sera of RA patients analyzed are positive for IgG anti-CarP antibodies (FIG. 10, Panel C). Likewise, 43% of sera from RA patients tested are positive for IgA anti-CarP-antibodies (FIG. 10, Panel D).

Anti-CarP Antibodies are Also Present in Sera of Anti-CCP2-Negative RA Patients

The group of RA patients analyzed in this study consisted of both ACPA-positive and ACPA-negative individuals, as measured by the CCP2 assay. Therefore, the association between anti-CarP antibodies and anti-CCP2 antibodies was analyzed next. The presence of anti-CarP antibodies and anti-CCP2 antibodies showed a limited degree of correlation when analyzing the entire RA population ($r^2=0.27$, $p<0.001$ for anti-CarP IgG or $r^2=0.15$, $p<0.001$ for IgA). However, substantial numbers of RA patients were also identified that are only positive for anti-CCP2 antibodies as well as a group of patients that is only positive for anti-CarP antibodies (FIG. 10, Panels E and F). It was observed that approximately 16% of the anti-CCP2-negative RA patients displayed anti-CarP IgG antibodies, whereas 30% of the anti-CCP2-negative RA patients tested positive for anti-CarP IgA (FIG. 10, Panels G and H). These data indicate that the presence of anti-CarP antibodies overlaps with the occurrence of anti-CCP2 antibodies, but that this overlap is not absolute as over 30% of the anti-CCP2-negative patients harbor anti-CarP antibodies. In total, more than 35% of all anti-CCP2-negative patients have either anti-CarP IgG or IgA antibodies.

Anti-CarP Antibodies are Associated with More Severe Radiological Damage

Figure 11:
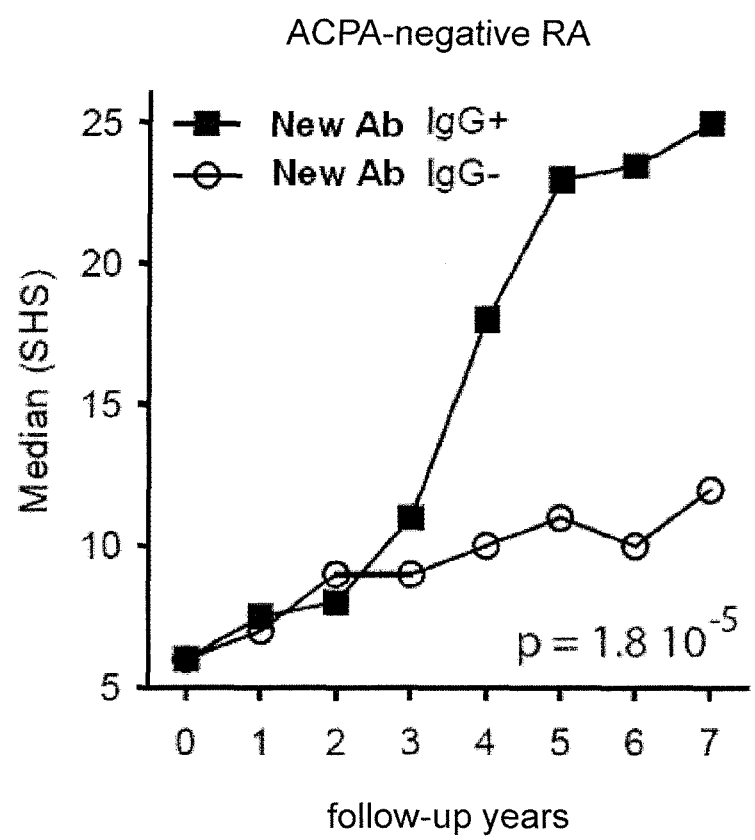
FIG. 11: Anti-CarP IgG antibodies are associated with a more severe radiological progression in ACPA-negative RA. The extent and rate of joint destruction were analyzed in all RA patients included, or analyzed separately for ACPA-negative or ACPA-positive subgroups (FIG. 13). The severity of joint destruction is depicted as median Sharp/van der Heijde score (SHS) on the Y-axis and the follow-up years on the X-axis. The patient number is listed for each time point below the X-axis. Radiological progression for the anti-CCP2-negative RA patients is shown. The P-value is derived from the analysis model as described in the methods section.
Figure 12A:
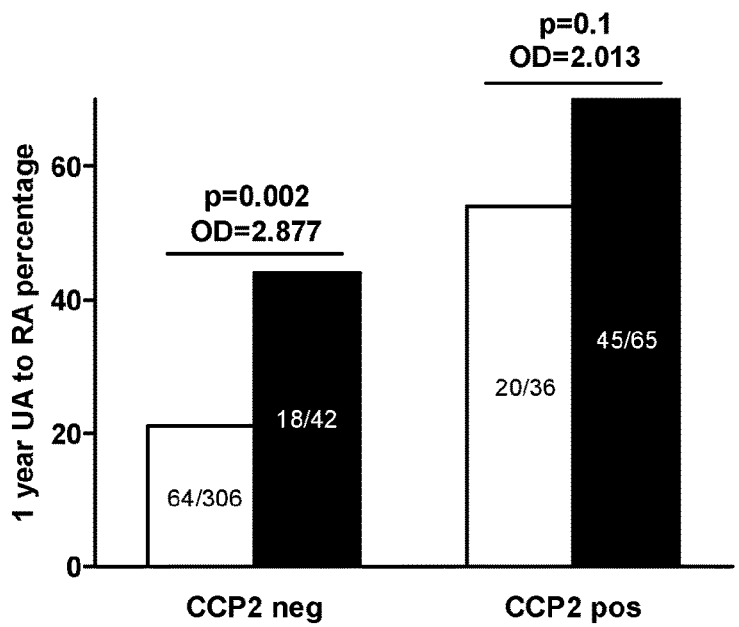
FIGS. 12A through 12C: Anti-CarP IgG antibodies are associated with the conversion of pre-disease to RA.
Figure 12B:
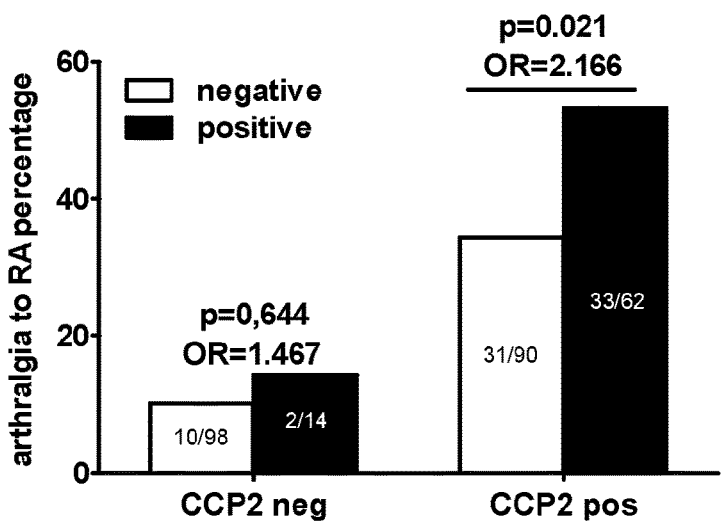
Figure 12C:
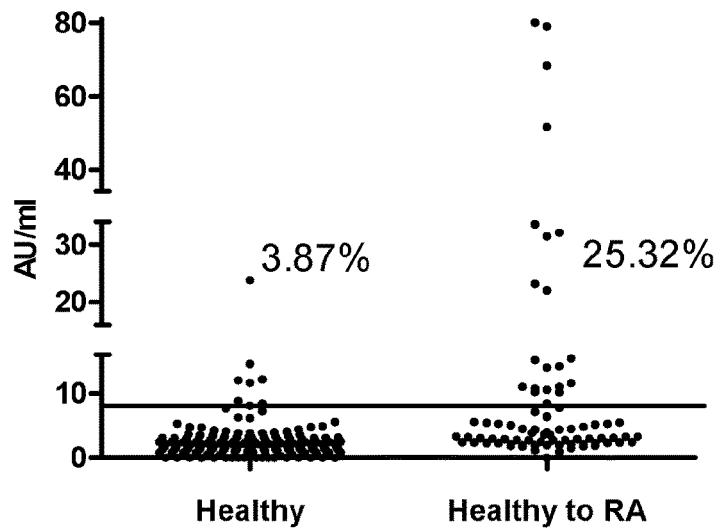
Figure 13:
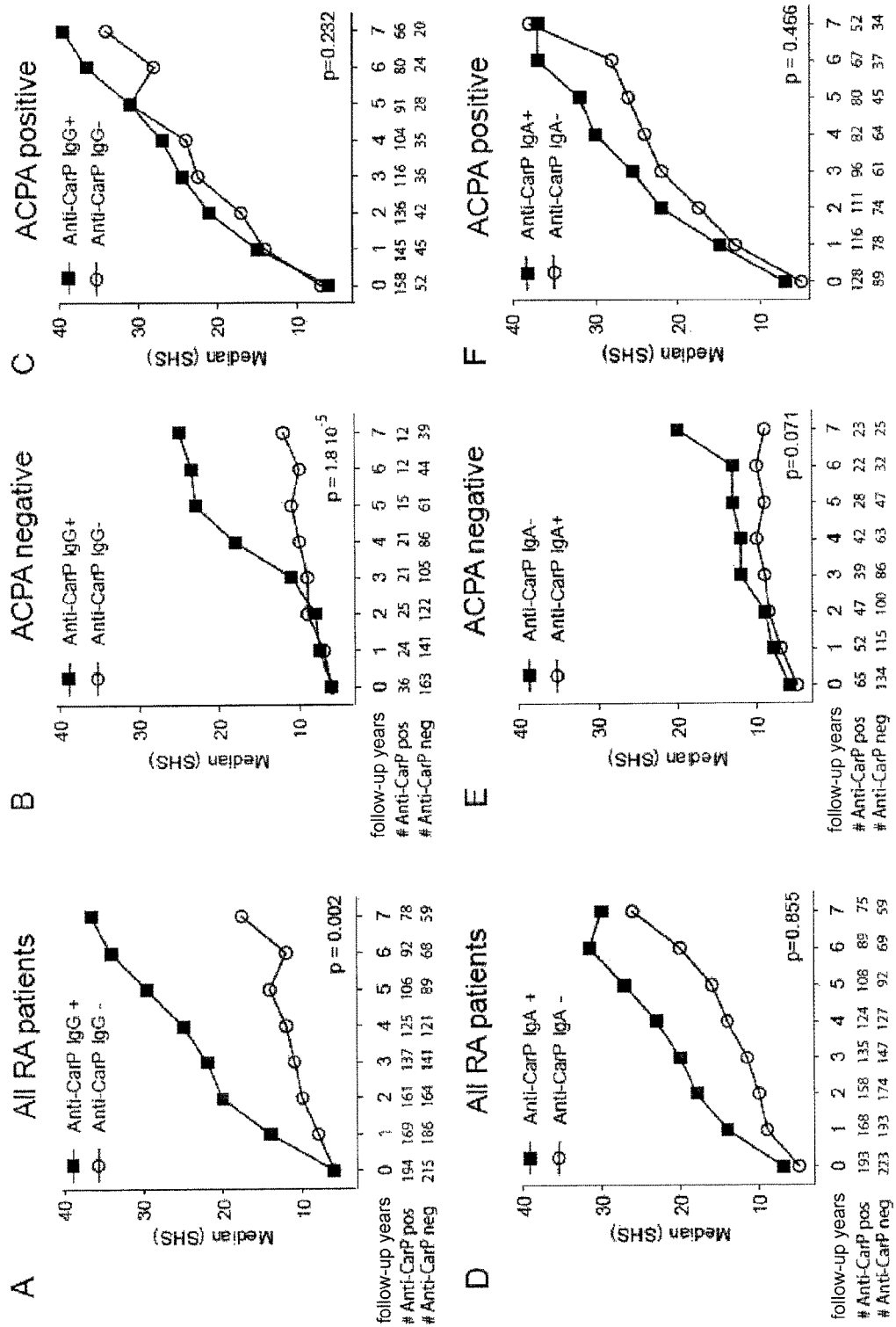
FIG. 13: Anti-CarP IgA antibodies are associated with more severe radiological progression in RA. The extent and rate of joint destruction were analyzed in the RA patients split up on the basis of positivity for ACPA and anti-CarP antibodies. Positivity for anti-CarP IgG antibodies is associated with a more severe radiological damage in ACPA-negative RA patients.
Figure 17:
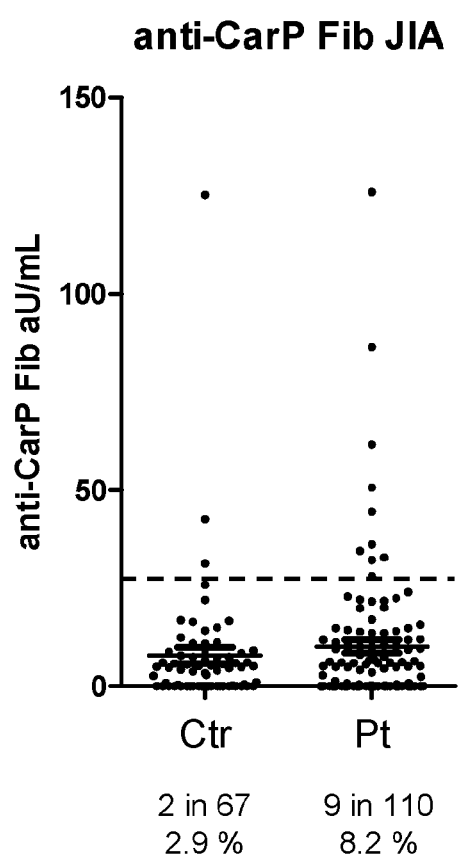
FIG. 17: Anti-CarP antibodies are present in sera of patients suffering from juvenile arthritis. ELISA was performed for the detection of anti-CarP IgG in sera of healthy children (Ctr) and in sera of patients suffering from juvenile arthritis. A cut-off was established using the mean plus two times the standard deviation of the healthy controls as described in the methods. Reactivity is depicted as arbitrary units per mL. The number of samples tested and the % positivity is indicated below the graph.

The presence of ACPA is associated with a more severe clinical disease course as measured by radiological damage. To analyze whether the presence of anti-CarP antibodies are also predictive for a more severe disease course, the extent of joint damage over time between anti-CarP-positive and -negative patients participating in the Leiden EAC cohort was compared. This cohort is an inception cohort of patients with recent-onset arthritis where X-rays of hands and feet are taken of all RA patients at yearly intervals to assess radiological damage using the Sharp/van der Heijde method.[21] It was observed that the presence of anti-CarP IgG strongly associates with a more severe disease progression. Patients positive for anti-CarP IgG had more joint destruction over seven years than IgG-negative patients without ($\beta=2.01$, 95% CI 1.68-2.40, $p=8.68\times10^{-14}$) or with correction of ACPA and RF ($\beta=1.41$, 95% CI 1.13-1.76, $p=0.002$) (FIG. 13). Anti-CarP IgA was associated with more joint destruction over seven years than anti-CarP IgA-negative patients without correction of ACPA and RF ($\beta=1.21$, 95% CI 1.01-1.45, $p=0.041$) but not after correction ($p=0.855$) (FIG. 13). As the analysis described above does not show whether anti-CarP antibodies predict radiological progression in the anti-CCP2-negative, anti-CCP2-positive or both RA subgroups, a stratified analysis was next performed. Importantly, this analysis revealed that the presence of anti-CarP IgG is associated with a more severe joint damage in the anti-CCP2-negative subgroup ($\beta=1.86$, 95% CI 1.41-2.66, $p=1.8\times10^{-5}$) (FIG. 11). Likewise, a similar trend toward more joint damage over time was observed for anti-CCP2-negative patients tested positive for IgA anti-CarP antibodies ($\beta=1.25$, 95% CI 0.98-1.58, $p=0.071$) (FIG. 13). In contrast, in the anti-CCP2-positive subgroup, which is already characterized by severe joint destruction, no additional increase was observed in individuals that also harbored anti-CarP antibodies (FIG. 13). Together, these data indicate that the detection of anti-CarP antibodies at baseline is predictive for a more destructive disease course in anti-CCP2-negative RA as measured by the Sharp/van der Heijde method.

Discussion

A family of autoantibodies that recognize carbamylated proteins, anti-CarP antibodies can be detected in sera of RA patients. Both inhibition studies and cohort studies show that anti-CarP antibodies and ACPA represent two different and independent autoantibody families, one recognizing carbamylated proteins and the other citrullinated proteins. The data show that anti-CarP antibodies and ACPA are, by and large, non-cross-reactive, although no exclusion is made that some cross-reactivity exists at the population level as is also indicated in recent data obtained in rabbits after vaccination with carbamylated proteins.[14] Interestingly, positivity for anti-CarP antibodies is related to clinical outcome as individuals positive for anti-CarP IgG, but negative for anti-CCP2 antibodies, have a more destructive disease course as compared to anti-CarP IgG-negative RA patients.

It is currently unknown which proteins undergo post-translational modifications like carbamylation. Carbamylation is mediated by cyanate, which is in equilibrium with urea. Increased urea concentrations, smoking and inflammation have been reported to shift this equilibrium toward cyanate and, hence, enhanced carbamylation.[13] Since currently no in vivo-relevant targets for anti-CarP antibodies are known, a complex protein mixture was used as an initial source of carbamylated protein antigens for the detection of anti-CarP antibodies. Western blot analyses indicate the recognition by anti-CarP antibodies of at least one dominant protein present in FCS after carbamylation employing cyanate (representing high urea concentrations) (FIG. 8, Panel D). However, these data are likely not to represent the in vivo situation where carbamylation is a more gradual, but constantly occurring process.[22] In this respect, it is likely that especially long-lived proteins acquire homocitrulline residues over time as carbamylation is nearly irreversible and, thus, will lead to the accumulation of homocitrulline residues on proteins with a long half-life. Intriguingly, the joint is known for the presence of long-lived proteins such as collagens and other cartilage-expressed proteins. Therefore, it is conceivable that such matrix-proteins will accumulate homocitrulline residues during life, especially under conditions of inflammation. Indeed, it has been shown that homocitrulline is present in the joint,[11] possibly representing the long-lived nature of many joint-derived proteins. It will be interesting to know the identity of these proteins and whether these can serve as a target for anti-CarP antibodies.

The molecular nature of the antigens recognized by ACPA was identified more than 15 years ago by describing that citrulline is an essential constituent of antigens recognized by these RA-specific antibodies.[23, 24] This finding has made considerable impact as it has opened up the way to relevant and novel insights into RA diagnosis and etiopathology.[1] For example, ACPA are now part of the new ACR/EULAR criteria for RA,[25] and have been implicated in RA pathogenesis, both in animal models[26, 27, 28] and in ex vivo human studies.[29, 30, 31, 32] Importantly, the description of ACPA has led to the realization that RA constitutes at least two clinical syndromes that share many clinical features, but differ with respect to genetic background, predisposing environmental factors and clinical progression/remission.[33, 3, 4, 34, 35] Although it is clearly too early to allow any firm conclusions, it is tempting to speculate that anti-CarP antibodies also contribute to disease pathogenesis and/or display diagnostic value, given the similar nature of the antigens recognized and their presence in ACPA-negative disease.

The presence of anti-CarP antibodies in anti-CCP2-negative disease is highly intriguing as it could potentially represent a novel biomarker that positively identifies at least part of this manifestation of RA. To gain further insight into this possibility, it is important to establish whether the presence of anti-CarP antibodies is specific for RA or also found in other rheumatic diseases, as well as whether their presence predict the development of (ACPA-negative) RA in patients suffering from early unclassified RA and/or joint complaints such as arthralgia.

To establish a cut-off to define a positive sample, the presence of IgG and IgA directed against Ca-FCS and FCS in sera of healthy controls was analyzed. All samples were tested for reactivity toward Ca-FCS and FCS, and absorbance values were converted into aU/mL using an anti-CarP antibody-positive standard present on the same plate. Since sera from several individual subjects also displayed reactivity toward non-modified FCS, the "FCS reactivity" was subtracted from the reactivity toward Ca-FCS using aU/mL as defined by the standard curve. Subsequently, the cut-off was calculated as the mean plus two times standard deviation and applied the cut-off to the data of the RA patients following a similar strategy. The disadvantage of this method is that a standard is used on Ca-FCS for the determination of aU/mL toward FCS, another antigenic entity. However, this method did allow the calculation of a specific response to the post-translational modification.

Every method of establishing a cut-off has advantages and limitations. Therefore, the observations were subsequently confirmed using another strategy as well, by calculating the cut-off as the mean plus two times standard deviation of the anti-Ca-FCS response in controls. This cut-off was applied to the data of the RA patients as was also employed before.[36] The association with radiological progression of IgG in ACPA-negative RA remains significant, albeit with a lower level of significance ($p=0.001$).

From a clinical perspective, the detection of anti-CarP antibodies in early arthritis could be highly rewarding since they predict a more severe disease course. Since early aggressive treatment in RA has been shown to prevent future damage,[37, 38] the detection of anti-CarP antibodies might be beneficial to identify anti-CCP2-negative patients at risk to develop severe disease. The identification of such patients might be important to guide treatment decisions early after onset of symptoms, especially in early arthritis patients that are difficult to classify.

In conclusion, in addition to the autoantibody system that recognizes citrullinated proteins (ACPA), an autoantibody system against carbamylated proteins (anti-CarP) is present in sera of RA patients. Detection of anti-CarP antibodies could offer new possibilities to identify patients at risk for a severe disease course.

REFERENCES

1. Klareskog L., J. Ronnelid, K. Lundberg, L. Padyukov, and L. Alfredsson. Immunity to citrullinated proteins in rheumatoid arthritis. *Annu. Rev. Immunol.* 2008; 26:651-75.

2. Kallberg H., L. Padyukov, R. M. Plenge, J. Ronnelid, P. K. Gregersen, A. H. van der Helm-van Mil et al. Gene-gene and gene-environment interactions involving HLA-DRB1, PTPN22, and smoking in two subsets of rheumatoid arthritis. *Am. J. Hum. Genet.* 2007; 80(5):867-75.

3. van der Helm-van Mil A. H., K. N. Verpoort, F. C. Breedveld, R. E. Toes, and T. W. Huizinga. Antibodies to citrullinated proteins and differences in clinical progression of rheumatoid arthritis. *Arthritis Res. Ther.* 2005; 7(5):R949-R958.

4. van der Woude D., A. Young, K. Jayakumar, B. J. Mertens, R. E. Toes, D. van der Heijde et al. Prevalence of and predictive factors for sustained disease-modifying antirheumatic drug-free remission in rheumatoid arthritis: results from two large early arthritis cohorts. *Arthritis Rheum.* 2009; 60(8):2262-71.

5. Visser K., K. N. Verpoort, H. van Dongen, S. M. van der Kooij, C. F. Allaart, R. E. Toes et al. Pretreatment serum levels of anti-cyclic citrullinated peptide antibodies are associated with the response to methotrexate in recent-onset arthritis. *Ann. Rheum. Dis.* 2008; 67(8):1194-5.

6. Cohen S. B., P. Emery, M. W. Greenwald, M. Dougados, R. A. Furie, M. C. Genovese et al. Rituximab for rheumatoid arthritis refractory to anti-tumor necrosis factor therapy: Results of a multicenter, randomized, double-blind, placebo-controlled, phase III trial evaluating primary efficacy and safety at twenty-four weeks. *Arthritis Rheum.* 2006; 54(9):2793-806.

7. Quartuccio L., M. Fabris, S. Salvin, F. Atzeni, M. Saracco, M. Benucci et al. Rheumatoid factor positivity rather than anti-CCP positivity, a lower disability and a lower number of anti-TNF agents failed are associated with response to rituximab in rheumatoid arthritis. *Rheumatology* (Oxford) 2009; 48(12):1557-9.

8. Gyorgy B., E. Toth, E. Tarcsa, A. Falus, and E. I. Buzas. Citrullination: a post-translational modification in health and disease. *Int. J. Biochem. Cell Biol.* 2006; 38(10):1662-77.

9. Wang Y., J. Wysocka, J. Sayegh, Y. H. Lee, J. R. Perlin, L. Leonelli et al. Human PAD4 regulates histone arginine methylation levels via demethylimination. *Science* 2004; 306(5694):279-83.

10. Li P., M. Li, M. R. Lindberg, M. J. Kennett, N. Xiong, and Y. Wang. PAD4 is essential for antibacterial innate immunity mediated by neutrophil extracellular traps. *J. Exp. Med.* 2010; 207(9):1853-62.

11. Mydel P., Z. Wang, M. Brisslert, A. Hellvard, L. E. Dahlberg, S. L. Hazen et al. Carbamylation-dependent activation of T cells: a novel mechanism in the pathogenesis of autoimmune arthritis. *J. Immunol.* 2010; 184(12):6882-90.

12. Sirpal S. Myeloperoxidase-mediated lipoprotein carbamylation as a mechanistic pathway for atherosclerotic vascular disease. *Clin. Sci.* (Lond) 2009; 116(9):681-95.

13. Wang Z., S. J. Nicholls, E. R. Rodriguez, O. Kummu, S. Horkko, J. Barnard et al. Protein carbamylation links inflammation, smoking, uremia and atherogenesis. *Nat. Med.* 2007; 13(10):1176-84.

14. Turunen S., M. K. Koivula, L. Risteli, and J. Risteli. Anticitrulline antibodies can be caused by homocitrulline-containing proteins in rabbits. *Arthritis Rheum.* 2010; 62(11):3345-52.

15. van Aken J., J. H. van Bilsen, C. F. Allaart, T. W. Huizinga, and F. C. Breedveld. The Leiden Early Arthritis Clinic. *Clin. Exp. Rheumatol.* 2003; 21(5 Suppl 31):S100-S105.

16. Arnett F. C., S. M. Edworthy, D. A. Bloch, D. J. McShane, J. F. Fries, N. S. Cooper et al. The American Rheumatism Association 1987 revised criteria for the classification of rheumatoid arthritis. *Arthritis Rheum.* 1988; 31(3):315-24.

17. Verpoort K. N., K. Cheung, A. Ioan-Facsinay, A. H. van der Helm-van Mil, J. K. de Vries-Bouwstra, C. F. Allaart et al. Fine specificity of the anti-citrullinated protein antibody response is influenced by the shared epitope alleles. *Arthritis Rheum.* 2007; 56(12):3949-52.

18. van der Helm-van Mil A. H., C. S. le, H. van Dongen, F. C. Breedveld, R. E. Toes, and T. W. Huizinga. A prediction rule for disease outcome in patients with recent-onset undifferentiated arthritis: how to guide individual treatment decisions. *Arthritis Rheum.* 2007; 56(2):433-40.

19. van Dongen H., J. van Aken, L. R. Lard, K. Visser, H. K. Ronday, H. M. Hulsmans et al. Efficacy of methotrexate treatment in patients with probable rheumatoid arthritis: a double-blind, randomized, placebo-controlled trial. *Arthritis Rheum.* 2007; 56(5):1424-32.

20. Willemze A., et al. (2011) The interaction between HLA shared epitope alleles and smoking and its contribution to autoimmunity against several citrullinated antigens. *Arthritis Rheum.* 63:1823-1832.

21. van der Linden M. P., et al. (2009) Association of a single-nucleotide polymorphism in CD40 with the rate of joint destruction in rheumatoid arthritis. *Arthritis Rheum.* 60:2242-2247.

22. Berlyne G. M. (1998) Carbamylated proteins and peptides in health and in uremia. *Nephron.* 79:125-130.

23. Masson-Bessiere C., et al. (2001) The major synovial targets of the rheumatoid arthritis-specific antifilaggrin autoantibodies are deiminated forms of the alpha- and beta-chains of fibrin. *J. Immunol.* 166:4177-4184.

24. Schellekens G. A., et al. (1998) Citrulline is an essential constituent of antigenic determinants recognized by rheumatoid arthritis-specific autoantibodies. *J. Clin. Invest.* 101:273-281.

25. Aletaha D., et al. (2010) The 2010 American College of Rheumatology/European League Against Rheumatism Classification Criteria for Rheumatoid Arthritis. *Arthritis and Rheumatism*.

26. Hill J. A., et al. (2008) Arthritis induced by post-translationally modified (citrullinated) fibrinogen in DR4-IE transgenic mice. *The Journal of Experimental Medicine* 205:967-979.

27. Kuhn K. A., et al. (2006) Antibodies against citrullinated proteins enhance tissue injury in experimental autoimmune arthritis. *J. Clin. Invest.* 116:961-973.

28. Uysal H., et al. (2009) Structure and pathogenicity of antibodies specific for citrullinated collagen type II in experimental arthritis. *J. Exp. Med.*

29. Clavel C., et al. (2008) Induction of macrophage secretion of tumor necrosis factor alpha through Fcgamma receptor IIa engagement by rheumatoid arthritis-specific autoantibodies to citrullinated proteins complexed with fibrinogen. *Arthritis Rheum.* 58:678-688.

30. Lu M. C., et al. (2010) Anti-citrullinated protein antibodies bind surface-expressed citrullinated Grp78 on monocyte/macrophages and stimulate tumor necrosis factor alpha production. *Arthritis Rheum.* 62:1213-1223.

31. Schuerwegh A. J. M., et al. (2010) Evidence for a functional role of IgE anti-citrullinated protein antibodies in rheumatoid arthritis. *Proceedings of the National Academy of Sciences* 107:2586-2591.

32. Trouw L. A., et al. (2009) Anti-cyclic citrullinated peptide antibodies from rheumatoid arthritis patients activate complement via both the classical and alternative pathways. *Arthritis Rheum.* 60:1923-1931.

33. Linn-Rasker S. P., et al. (2006) Smoking is a risk factor for anti-CCP antibodies only in rheumatoid arthritis patients who carry HLA-DRB1 shared epitope alleles. *Ann. Rheum. Dis.* 65:366-371.

34. van Gaalen F. A., et al. (2004) Association between HLA class II genes and autoantibodies to cyclic citrullinated peptides (CCPs) influences the severity of rheumatoid arthritis. *Arthritis Rheum.* 50:2113-2121.

35. Verpoort K. N., et al. (2005) Association of HLA-DR3 with anti-cyclic citrullinated peptide antibody-negative rheumatoid arthritis. *Arthritis Rheum.* 52:3058-3062.

36. Verpoort K. N., et al. (2007) Fine specificity of the anti-citrullinated protein antibody response is influenced by the shared epitope alleles. *Arthritis Rheum.* 56:3949-3952.

37. van der Helm-van Mil A. H., et al. (2007) A prediction rule for disease outcome in patients with recent-onset undifferentiated arthritis: how to guide individual treatment decisions. *Arthritis Rheum.* 56:433-440.

38. van Dongen H., et al. (2007) Efficacy of methotrexate treatment in patients with probable rheumatoid arthritis: a double-blind, randomized, placebo-controlled trial. *Arthritis Rheum.* 56:1424-1432.

39. de Rooy D. P. C., et al. (2011) Predicting arthritis outcomes; what can be learned from the Leiden Early Arthritis Clinic? *Rheumatology* 50:93-100.

40. Arnett F. C., et al. (1988) The American Rheumatism Association 1987 revised criteria for the classification of rheumatoid arthritis. *Arthritis Rheum.* 31:315-324.

41. Suwannalai P., et al. (2011) Anti-citrullinated protein antibodies have a low avidity compared with antibodies against recall antigens. *Annals of the Rheumatic Diseases* 70:373-379.

42. Verpoort K. N., et al. (2007) Fine specificity of the anti-citrullinated protein antibody response is influenced by the shared epitope alleles. *Arthritis and Rheumatism* 56:3949-3952.

43. Schellekens G. A., et al. (1998) Citrulline is an essential constituent of antigenic determinants recognized by rheumatoid arthritis-specific autoantibodies. *J. Clin. Invest.* 101:273-281.

44. van der Heijde D. (2000) How to read radiographs according to the Sharp/van der Heijde method. *Journal of Rheumatology* 27:261-263.

TABLE I

List of lysine-containing peptides of fibrinogen alpha and their homocitrulline-containing counterparts

| Lysine-containing peptides of fibrinogen alpha | | Homocitrulline-containing peptides of fibrinogen alpha | |
|---|---|---|---|
| | SEQ ID NO: | | SEQ ID NO: |
| 1 | 4 | RVVERHQSACKDSDWPFCSDE | 1 | 5 | RVVERHQSAChomocitDSDWPFCSDE |
| 2 | 6 | PFCSDEDWNYKCPSGCRMKGL | 2 | 7 | PFCSDEDWNYhomocitCPSGCRMhomocitGL |
| 3 | 8 | NYKCPSGCRMKGLIDEVNQDF | 3 | 9 | NYhomocitCPSGCRMhomocitGLIDEVNQDF |
| 4 | 10 | VNQDFTNRINKLKNSLFEYQK | 4 | 11 | VNQDFTNRINhomocitLhomocitNSLFEYQhomocit |
| 5 | 12 | QDFTNRINKLKNSLFEYQKNN | 5 | 13 | QDFTNRINhomocitLhomocitNSLFEYQhomocitNN |
| 6 | 14 | KLKNSLFEYQKNNKDSHSLTT | 6 | 15 | homocitLhomocitNSLFEYQhomocitNNhomocitDSHSLTT |
| 7 | 16 | NSLFEYQKNNKDSHSLTTNIM | 7 | 17 | NSLFEYQhomocitNNhomocitDSHSLTTNIM |
| 8 | 18 | EDLRSRIEVLKRKVIEKVQHI | 8 | 19 | EDLRSRIEVLhomocitRhomocitVIEhomocitVQHI |
| 9 | 20 | LRSRIEVLKRKVIEKVQHIQL | 9 | 21 | LRSRIEVLhomocitRhomocitVIEhomocitVQHIQL |
| 10 | 22 | IEVLKRKVIEKVQHIQLLQKN | 10 | 23 | IEVLhomocitRhomocitVIEhomocitVQHIQLLQhomocitN |
| 11 | 24 | EKVQHIQLLQKNVRAQLVDMK | 11 | 25 | EhomocitVQHIQLLQhomocitNVRAQLVDMhomocit |
| 12 | 26 | KNVRAQLVDMKRLEVDIDIKI | 12 | 27 | homocitNVRAQLVDMhomocitRLEVDIDIhomocitI |
| 13 | 28 | MKRLEVDIDIKIRSCRGSCSR | 13 | 29 | MhomocitRLEVDIDIhomocitIRSCRGSCSR |
| 14 | 30 | SRALAREVDLKDYEDQQKQLE | 14 | 31 | SRALAREVDLhomocitDYEDQQhomocitQLE |
| 15 | 32 | VDLKDYEDQQKQLEQVIAKDL | 15 | 33 | VDLhomocitDYEDQQhomocitQLEQVIAhomocitDL |
| 16 | 34 | QQKQLEQVIAKDLLPSRDRQH | 16 | 35 | QQhomocitQLEQVIAhomocitDLLPSRDRQH |
| 17 | 36 | SRDRQHLPLIKMKPVPDLVPG | 17 | 37 | SRDRQHLPLIhomocitMhomocitPVPDLVPG |
| 18 | 38 | DRQHLPLIKMKPVPDLVPGNF | 18 | 39 | DRQHLPLIhomocitMhomocitPVPDLVPGNF |
| 19 | 40 | PVPDLVPGNFKSQLQKVPPEW | 19 | 41 | PVPDLVPGNFhomocitSQLQhomocitVPPEW |
| 20 | 42 | VPGNFKSQLQKVPPEWKALTD | 20 | 43 | VPGNFhomocitSQLQhomocitVPPEWhomocitALTD |
| 21 | 44 | SQLQKVPPEWKALTDMPQMRM | 21 | 45 | SQLQhomocitVPPEWhomocitALTDMPQMRM |
| 22 | 46 | SSGTGGTATWKPGSSGPGSTG | 22 | 47 | SSGTGGTATWhomocitPGSSGPGSTG |
| 23 | 48 | PGTRREYHTEKLVTSKGDKEL | 23 | 49 | PGTRREYHTEhomocitLVTShomocitGDhomocitEL |
| 24 | 50 | EYHTEKLVTSKGDKELRTGKE | 24 | 51 | EYHTEhomocitLVTShomocitGDhomocitELRTGhomocitE |

TABLE I-continued

List of lysine-containing peptides of fibrinogen alpha and their homocitrulline-containing counterparts

| | Lysine-containing peptides of fibrinogen alpha | | | Homocitrulline-containing peptides of fibrinogen alpha |
|---|---|---|---|---|
| | SEQ ID NO: | | | SEQ ID NO: |
| 25 | 52 | TEKLVTSKGDKELRTGKEKVT | 25 | 53 | TEhomocitLVTShomocitGDhomocitELRTGhomocitEhomocitVT |
| 26 | 54 | SKGDKELRTGKEKVTSGSTTT | 26 | 55 | ShomocitGDhomocitELRTGhomocitEhomocitVTSGSTTT |
| 27 | 56 | GDKELRTGKEKVTSGSTTTTR | 27 | 57 | GDhomocitELRTGhomocitEhomocitVTSGSTTTTR |
| 28 | 58 | STTTTRRSCSKTVTKTVIGPD | 28 | 59 | STTTTRRSCShomocitTVThomocitTVIGPD |
| 29 | 60 | TRRSCSKTVTKTVIGPDGHKE | 29 | 61 | TRRSCShomocitTVThomocitTVIGPDGHhomocitE |
| 30 | 62 | TKTVIGPDGHKEVTKEVVTSE | 30 | 63 | ThomocitTVIGPDGHhomocitEVThomocitEVVTSE |
| 31 | 64 | IGPDGHKEVTKEVVTSEDGSD | 31 | 65 | IGPDGHhomocitEVThomocitEVVTSEDGSD |
| 32 | 66 | AAFFDTASTGKTFPGFFSPML | 32 | 67 | AAFFDTASTGhomocitTFPGFFSPML |
| 33 | 68 | GSESGIFTNTKESSSHHPGIA | 33 | 69 | GSESGIFTNThomocitESSSHHPGIA |
| 34 | 70 | PGIAEFPSRGKSSSYSKQFTS | 34 | 71 | PGIAEFPSRGhomocitSSSYShomocitQFTS |
| 35 | 72 | PSRGKSSSYSKQFTSSTSYNR | 35 | 73 | PSRGhomocitSSSYShomocitQFTSSTSYNR |
| 36 | 74 | YNRGDSTFESKSYKMADEAGS | 36 | 75 | YNRGDSTFEShomocitSYhomocitMADEAGS |
| 37 | 76 | GDSTFESKSYKMADEAGSEAD | 37 | 77 | GDSTFEShomocitSYhomocitMADEAGSEAD |
| 38 | 78 | EADHEGTHSTKRGHAKSRPVR | 38 | 79 | EADHEGTHSThomocitRGHAhomocitSRPVR |
| 39 | 80 | GTHSTKRGHAKSRPVRDCDDV | 39 | 81 | GTHSThomocitRGHAhomocitSRPVRDCDDV |
| 40 | 82 | SGTQSGIFNIKLPGSSKIFSV | 40 | 83 | SGTQSGIFNIhomocitLPGSShomocitIFSV |
| 41 | 84 | IFNIKLPGSSKIFSVYCDQET | 41 | 85 | IFNIhomocitLPGSShomocitIFSVYCDQET |
| 42 | 86 | LNFNRTWQDYKRGFGSLNDEG | 42 | 87 | LNFNRTWQDYhomocitRGFGSLNDEG |
| 43 | 88 | VRGIHTSPLGKPSLSP | 43 | 89 | VRGIHTSPLGhomocitPSLSP |

TABLE II

List of lysine-containing peptides of fibrinogen beta and their homocitrulline-containing counterparts

| | Lysine-containing peptides of fibrinogen beta | | | Homocitrulline-containing peptides of fibrinogen beta |
|---|---|---|---|---|
| | SEQ ID NO: | | | SEQ ID NO: |
| 1 | 90 | MKRMVSWSFHKL | 1 | 91 | MhomocitRMVSWSFHhomocitL |
| 2 | 92 | MKRMVSWSFHKLKTMKHLLLL | 2 | 93 | MhomocitRMVSWSFHhomocitLhomocitTMhomocitHLLLL |
| 3 | 94 | RMVSWSFHKLKTMKHLLLLLL | 3 | 95 | RMVSWSFHhomocitLhomocitTMhomocitHLLLLLL |
| 4 | 96 | SWSFHKLKTMKHLLLLLLCVF | 4 | 97 | SWSFHhomocitLhomocitTMhomocitHLLLLLLCVF |
| 5 | 98 | LLLLLCVFLVKSQGVNDNEEG | 5 | 99 | LLLLLCVFLVhomocitSQGVNDNEEG |
| 6 | 100 | FSARGHRPLDKKREEAPSLRP | 6 | 101 | FSARGHRPLDhomocithomocitREEAPSLRP |
| 7 | 102 | SARGHRPLDKKREEAPSLRPA | 7 | 103 | SARGHRPLDhomocithomocitREEAPSLRPA |
| 8 | 104 | SGGGYRARPAKAAATQKKVER | 8 | 105 | SGGGYRARPAhomocitAAATQhomocithomocitVER |
| 9 | 106 | ARPAKAAATQKKVERKAPDAG | 9 | 107 | ARPAhomocitAAATQhomocithomocitVERhomocitAPDAG |

TABLE II-continued

List of lysine-containing peptides of fibrinogen beta and their homocitrulline-containing counterparts

| Lysine-containing peptides of fibrinogen beta | | | Homocitrulline-containing peptides of fibrinogen beta | | |
|---|---|---|---|---|---|
| | SEQ ID NO: | | | SEQ ID NO: | |
| 10 | 108 | RPAKAAATQKKVERKAPDAGG | 10 | 109 | RPAhomocitAAATQhomocithomocitVERhomocitAPDAGG |
| 11 | 110 | AAATQKKVERKAPDAGGCLHA | 11 | 111 | AAATQhomocithomocitVERhomocitAPDAGGCLHA |
| 12 | 112 | SSSFQYMYLLKDLWQKRQKQV | 12 | 113 | SSSFQYMYLLhomocitDLWQhomocitRQhomocitQV |
| 13 | 114 | YMYLLKDLWQKRQKQVKDNEN | 13 | 115 | YMYLLhomocitDLWQhomocitRQhomocitQVhomocitDNEN |
| 14 | 116 | LLKDLWQKRQKQVKDNENVVN | 14 | 117 | LLhomocitDLWQhomocitRQhomocitQVhomocitDNENVVN |
| 15 | 118 | DLWQKRQKQVKDNENVVNEYS | 15 | 119 | DLWQhomocitRQhomocitQVhomocitDNENVVNEYS |
| 20 | 120 | PVVSCEEIIRKGGETSEMYLI | 20 | 121 | PVVSCEEIIRhomocitGGETSEMYLI |
| 21 | 122 | MYLIQPDSSVKPYRVYCDMNT | 21 | 123 | MYLIQPDSSVhomocitPYRVYCDMNT |
| 22 | 124 | VDFGRKWDPYKQGFGNVATNT | 22 | 125 | VDFGRhomocitWDPYhomocitQGFGNVATNT |
| 23 | 126 | FGNVATNTDGKNYCGLPGEYW | 23 | 127 | FGNVATNTDGhomocitNYCGLPGEYW |
| 24 | 128 | LPGEYWLGNDKISQLTRMGPT | 24 | 129 | LPGEYWLGNDhomocitISQLTRMGPT |
| 25 | 130 | TELLIEMEDWKGDKVKAHYGG | 25 | 131 | TELLIEMEDWhomocitGDhomocitVhomocitAHYGG |
| 26 | 132 | LIEMEDWKGDKVKAHYGGFTV | 26 | 133 | LIEMEDWhomocitGDhomocitVhomocitAHYGGFTV |
| 27 | 134 | EMEDWKGDKVKAHYGGFTVQN | 27 | 135 | EMEDWhomocitGDhomocitVhomocitAHYGGFTVQN |
| 28 | 136 | GGFTVQNEANKYQISVNKYRG | 28 | 137 | GGFTVQNEANhomocitYQISVNhomocitYRG |
| 29 | 138 | EANKYQISVNKYRGTAGNALM | 29 | 139 | EANhomocitYQISVNhomocitYRGTAGNALM |
| 30 | 140 | NDGWLTSDPRKQCSKEDGGGW | 30 | 141 | NDGWLTSDPRhomocitQCShomocitEDGGGW |
| 31 | 142 | LTSDPRKQCSKEDGGGWWYNR | 31 | 143 | LTSDPRhomocitQCShomocitEDGGGWWYNR |
| 32 | 144 | WGGQYTWDMAKHGTDDGVVWM | 32 | 145 | WGGQYTWDMAhomocitHGTDDGVVWM |
| 33 | 146 | TDDGVVWMNWKGSWYSMRKMS | 33 | 147 | TDDGVVWMNWhomocitGSWYSMRhomocitMS |
| 34 | 148 | NWKGSWYSMRKMSMKIRPFFQ | 34 | 149 | NWhomocitGSWYSMRhomocitMSMhomocitIRPFFQ |
| 35 | 150 | SWYSMRKMSMKIRPFFPQQ | 35 | 151 | SWYSMRhomocitMSMhomocitIRPFFPQQ |

TABLE III

List of lysine-containing peptides of fibrinogen gamma and their homocitrulline-containing counterparts

| Lysine-containing peptides of fibrinogen gamma | | | Homocitrulline-containing peptides of fibrinogen gamma | | |
|---|---|---|---|---|---|
| | SEQ ID NO: | | | SEQ ID NO: | |
| 1 | 152 | IADFLSTYQTKVDKDLQSLED | 1 | 153 | IADFLSTYQThomocitVDhomocitDLQSLED |
| 2 | 154 | FLSTYQTKVDKDLQSLEDILH | 2 | 155 | FLSTYQThomocitVDhomocitDLQSLEDILH |
| 3 | 156 | LEDILHQVENKTSEVKQLIKA | 3 | 157 | LEDILHQVENhomocitTSEVhomocitQLIhomocitA |
| 4 | 158 | HQVENKTSEVKQLIKAIQLTY | 4 | 159 | HQVENhomocitTSEVhomocitQLIhomocitAIQLTY |
| 5 | 160 | NKTSEVKQLIKAIQLTYNPDE | 5 | 161 | NhomocitTSEVhomocitQLIhomocitAIQLTYNPDE |
| 6 | 162 | QLTYNPDESSKPNMIDAATLK | 6 | 163 | QLTYNPDESShomocitPNMIDAATLhomocit |
| 7 | 164 | KPNMIDAATLKSRKMLEEIMK | 7 | 165 | homocitPNMIDAATLhomocitSRhomocitMLEEIMhomocit |

TABLE III-continued

List of lysine-containing peptides of fibrinogen gamma and their homocitrulline-containing counterparts

| | Lysine-containing peptides of fibrinogen gamma | | | Homocitrulline-containing peptides of fibrinogen gamma | |
|---|---|---|---|---|---|
| | SEQ ID NO: | | | SEQ ID NO: | |
| 8 | 166 | MIDAATLKSRKMLEEIMKYEA | 8 | 167 | MIDAATLhomocitSRhomocitMLEEIMhomocitYEA |
| 9 | 168 | KSRKMLEEIMKYEASILTHDS | 9 | 169 | homocitSRhomocitMLEEIMhomocitYEASILTHDS |
| 10 | 170 | LQEIYNSNNQKIVNLKEKVAQ | 10 | 171 | LQEIYNSNNQhomocitIVNLhomocitEhomocitVAQ |
| 11 | 172 | NSNNQKIVNLKEKVAQLEAQC | 11 | 173 | NSNNQhomocitIVNLhomocitEhomocitVAQLEAQC |
| 12 | 174 | NNQKIVNLKEKVAQLEAQCQE | 12 | 175 | NNQhomocitIVNLhomocitEhomocitVAQLEAQCQE |
| 13 | 176 | QLEAQCQEPCKDTVQIHDITG | 13 | 177 | QLEAQCQEPChomocitDTVQIHDITG |
| 14 | 178 | DTVQIHDITGKDCQDIANKGA | 14 | 179 | DTVQIHDITGhomocitDCQDIANhomocitGA |
| 15 | 180 | TGKDCQDIANKGAKQSGLYFI | 15 | 181 | TGhomocitDCQDIANhomocitGAhomocitQSGLYFI |
| 16 | 182 | DCQDIANKGAKQSGLYFIKPL | 16 | 183 | DCQDIANhomocitGAhomocitQSGLYFIhomocitPL |
| 17 | 184 | GAKQSGLYFIKPLKANQQFLV | 17 | 185 | GAhomocitQSGLYFIhomocitPLhomocitANQQFLV |
| 18 | 186 | GSGNGWTVFQKRLDGSVDFKK | 18 | 187 | GSGNGWTVFQhomocitRLDGSVDFhomocithomocit |
| 19 | 188 | QKRLDGSVDFKKNWIQYKEGF | 19 | 189 | QhomocitRLDGSVDFhomocithomocitNWIQYhomocitEGF |
| 20 | 190 | KRLDGSVDFKKNWIQYKEGFG | 20 | 191 | homocitRLDGSVDFhomocithomocitNWIQYhomocitEGFG |
| 21 | 192 | VDFKKNWIQYKEGFGHLSPTG | 21 | 193 | VDFhomocithomocitNWIQYhomocitEGFGHLSPTG |
| 22 | 194 | GTTEFWLGNEKIHLISTQSAI | 22 | 195 | GTTEFWLGNEhomocitIHLISTQSAI |
| 23 | 196 | RTSTADYAMFKVGPEADKYRL | 23 | 197 | RTSTADYAMFhomocitVGPEADhomocitYRL |
| 24 | 198 | AMFKVGPEADKYRLTYAYFAG | 24 | 199 | AMFhomocitVGPEADhomocitYRLTYAYFAG |
| 25 | 200 | GFDFGDDPSDKFFTSHNGMQF | 25 | 201 | GFDFGDDPSDhomocitFFTSHNGMQF |
| 26 | 202 | QFSTWDNDNDKFEGNCAEQDG | 26 | 203 | QFSTWDNDNDhomocitFEGNCAEQDG |
| 27 | 204 | EQDGSGWWMNKCHAGHLNGVY | 27 | 205 | EQDGSGWWMNhomocitCHAGHLNGVY |
| 28 | 206 | GVYYQGGTYSKASTPNGYDNG | 28 | 207 | GVYYQGGTYShomocitASTPNGYDNG |
| 29 | 208 | YDNGIIWATWKTRWYSMKKTT | 29 | 209 | YDNGIIWATWhomocitTRWYSMhomocithomocitTT |
| 30 | 210 | ATWKTRWYSMKKTTMKIIPFN | 30 | 211 | ATWhomocitTRWYSMhomocithomocitTTMhomocitIIPFN |
| 31 | 212 | TWKTRWYSMKKTTMKIIPFNR | 31 | 213 | TWhomocitTRWYSMhomocithomocitTTMhomocitIIPFNR |
| 32 | 214 | RWYSMKKTTMKIIPFNRLTIG | 32 | 215 | RWYSMhomocithomocitTTMhomocitIIPFNRLTIG |

The invention claimed is:

1. A kit for the detection of anti-Ca-Fib antibodies, in a body fluid of an individual, the kit comprising:
    an in vitro carbamylated fibrinogen peptide comprising a peptide selected from the group consisting of the odd numbered SEQ ID NOs:5-215,
    a solid support, and
    an anti-human immunoglobulin antibody.

2. A kit for detecting anti-CarP antibodies in a body fluid of an individual, the kit comprising:
    an in vitro carbamylated fetal calf serum (FCS),
    a solid support, and
    an anti-human immunoglobulin antibody.

3. The kit of claim 2, wherein the anti-human immunoglobulin antibody comprises an anti-human IgG antibody.

4. The kit of claim 2, wherein the anti-human immunoglobulin antibody comprises an anti-human IgA antibody.

5. The kit of claim 2 further comprising:
    a citrullinated protein or peptide.

6. The kit of claim 1 comprising two carbamylated fibrinogen proteins or peptides.

7. The kit of claim 6 comprising three carbamylated proteins or peptides.

8. The kit of claim 1, further comprising a fibrinogen peptide having a sequence selected from the group consisting of the even numbered SEQ ID NOS:4-214.

9. The kit of claim 2, further comprising a non-modified FCS or a citrullinated FCS.

* * * * *

UNITED STATES PATENT AND TRADEMARK OFFICE
CERTIFICATE OF CORRECTION

PATENT NO. : 9,632,084 B2
APPLICATION NO. : 13/983374
DATED : April 25, 2017
INVENTOR(S) : Leendert Adrianus Trouw et al.

It is certified that error appears in the above-identified patent and that said Letters Patent is hereby corrected as shown below:

In the Specification

| | | |
|---|---|---|
| Column 3, | Line 33, | change "a faun of" to --a form of-- |
| Column 11, | Line 29, | change "(Fig. 1 B) to --(FIG. 1B)-- |
| Column 13, | Line 51, | change "(24 mg/me" to --(24 mg/ml)-- |
| Column 15, | Lines 40-41, | change "IgG 4bb ABTS.$^{(41)}$" to --IgG antibody (Dako). Following the last washings, HRP enzyme activity was visualized using ABTS.$^{(41)}$-- |

Signed and Sealed this
Fifth Day of December, 2017

Joseph Matal
*Performing the Functions and Duties of the
Under Secretary of Commerce for Intellectual Property and
Director of the United States Patent and Trademark Office*